US009090909B2

(12) United States Patent
Ban et al.

(10) Patent No.: US 9,090,909 B2
(45) Date of Patent: Jul. 28, 2015

(54) COMPOSITION FOR INDUCING PLURIPOTENT STEM CELL, AND USE THEREOF

(75) Inventors: Hiroshi Ban, Tsukuba (JP); Yasuji Ueda, Tsukuba (JP); Noemi Fusaki, Tsukuba (JP); Koichi Saeki, Tsukuba (JP); Mamoru Hasegawa, Tsukuba (JP)

(73) Assignee: DNAVEC CORPORATION, Ibaraki (JP)

( * ) Notice: Subject to any disclaimer, the term of this patent is extended or adjusted under 35 U.S.C. 154(b) by 106 days.

(21) Appl. No.: 13/819,235

(22) PCT Filed: Aug. 30, 2011

(86) PCT No.: PCT/JP2011/069588
§ 371 (c)(1),
(2), (4) Date: Apr. 29, 2013

(87) PCT Pub. No.: WO2012/029770
PCT Pub. Date: Mar. 8, 2012

(65) Prior Publication Data
US 2013/0210150 A1      Aug. 15, 2013

(30) Foreign Application Priority Data

Aug. 30, 2010   (JP) ................................. 2010-192752

(51) Int. Cl.
| | | |
|---|---|---|
| C12N 5/00 | (2006.01) | |
| C12N 5/02 | (2006.01) | |
| C12N 15/86 | (2006.01) | |
| C12N 5/074 | (2010.01) | |
| C12N 15/63 | (2006.01) | |

(52) U.S. Cl.
CPC .............. *C12N 15/86* (2013.01); *C12N 5/0696* (2013.01); *C12N 15/63* (2013.01); *C12N 2501/602* (2013.01); *C12N 2501/603* (2013.01); *C12N 2501/604* (2013.01); *C12N 2506/13* (2013.01); *C12N 2510/00* (2013.01); *C12N 2760/18843* (2013.01)

(58) Field of Classification Search
CPC .............. C12N 5/0696; C12N 2501/60; C12N 2501/602; C12N 2501/603; C12N 2501/304; C12N 15/68
See application file for complete search history.

(56) References Cited

U.S. PATENT DOCUMENTS

| | | |
|---|---|---|
| 2011/0287538 A1 | 11/2011 | Fusaki et al. |
| 2013/0065311 A1 | 3/2013 | Yamanaka et al. |

FOREIGN PATENT DOCUMENTS

| | | |
|---|---|---|
| CN | 1355851 A | 6/2002 |
| CN | 101617043 A | 12/2009 |
| EP | 1186667 A1 | 3/2002 |
| EP | 2096169 A1 | 9/2009 |
| EP | 2322611 A1 | 5/2011 |
| EP | 2434012 A1 | 3/2012 |
| EP | 2559757 A1 | 2/2013 |
| WO | WO-00/70070 A1 | 11/2000 |
| WO | WO-2009/057831 A1 | 5/2009 |
| WO | WO-2009/133971 A1 | 11/2009 |
| WO | WO-2010/008054 A1 | 1/2010 |
| WO | WO-2010/030003 A1 | 3/2010 |
| WO | WO-2010/038904 A1 | 4/2010 |
| WO | WO-2011/129446 A1 | 10/2011 |

OTHER PUBLICATIONS

Ban et al., "Efficient Generation of Transgene-Free Human Induced Pluripotent Stem Cells (iPSCs) by Temperature-Sensitive Sendai Virus Vectors," *Proc. Natl. Acad. Sci. USA* 108:14234-14239 (2011) (Supplemental Pages Included).
Carey et al., "Reprogramming of Murine and Human Somatic Cells Using a Single Polycistronic Vector," *Proc. Natl. Acad. Sci. USA* 106:157-162 (2009).
Fusaki et al., "Efficient Induction of Transgene-Free Human Pluripotent Stem Cells Using a Vector Based on Sendai Virus, an RNA Virus that Does Not Integrate Into the Host Genome," *Proc. Jpn. Acad. Ser. B. Phys. Biol. Sci.* 85:348-362 (2009).
Gonzalez et al., "Generation of Mouse-Induced Pluripotent Stem Cells by Transient Expression of a Single Nonviral Polycistronic Vector," *Proc. Natl. Acad. Sci. USA* 106:8918-8922 (2009).
Lowry et al., "Generation of Human Induced Pluripotent Stem Cells from Dermal Fibroblasts," *Proc. Natl. Acad. Sci. USA* 105:2883-2888 (2008).
Maekawa et al., "Direct Reprogramming of Somatic Cells Is Promoted by Maternal Transcription Factor Glis1," *Nature* 474:225-229 (2011).
Maherali et al., "Directly Reprogrammed Fibroblasts Show Global Epigenetic Remodeling and Widespread Tissue Contribution," *Cell Stem Cell* 1:55-70 (2007) (Supplemental Pages Included).
Masaki et al., "Heterogeneity of Pluripotent Marker Gene Expression in Colonies Generated in Human iPS Cell Induction Culture," *Stem Cell Res.* 1:105-115 (2008) (Supplementary Pages Included).
Okita et al., "Generation of Germline-Competent Induced Pluripotent Stem Cells," *Nature* 448:313-317 (2007).
Okita et al., "Generation of Mouse Induced Pluripotent Stem Cells Without Viral Vectors," *Science* 322:949-953 (2008).
Park et al., "Reprogramming of Human Somatic Cells to Pluripotency with Defined Factors," *Nature* 451:141-146 (2008) (Supplementary Pages Included).

(Continued)

*Primary Examiner* — Valarie Bertoglio
(74) *Attorney, Agent, or Firm* — Clark & Elbing LLP

(57) ABSTRACT

The present invention provides Sendai virus vectors in which genes that encode reprograming factors for inducing pluripotent stem cells are incorporated in a specific order, compositions comprising these vectors for gene delivery to be used in the induction of pluripotent stem cells, and uses thereof. Incorporation of the KLF gene, OCT gene, and SOX gene in a specific order into a single Sendai virus vector successfully and significantly increased the efficiency of pluripotent stem cell induction. Loading multiple reprogramming factors into a single vector can further increase the induction efficiency of pluripotent stem cells while reducing the number of necessary vectors.

16 Claims, 22 Drawing Sheets

(56) References Cited

OTHER PUBLICATIONS

Seki et al., "Generation of Induced Pluripotent Stem Cells from Human Terminally Differentiated Circulating T Cells," *Cell Stem Cell* 7:11-14 (2010) (Supplemental Pages Included).

Stadtfeld et al., "Induced Pluripotent Stem Cells Generated Without Viral Integration," *Science* 322:945-949 (2008).

Takahashi and Yamanaka, "Induction of Pluripotent Stem Cells from Mouse Embryonic and Adult Fibroblast Cultures by Defined Factors," *Cell* 126:663-676 (2006) (Supplemental Pages Included).

Takahashi et al., "Induction of Pluripotent Stem Cells from Adult Human Fibroblasts by Defined Factors," *Cell* 131:861-872 (2007) (Supplemental Pages Included).

Wernig et al., "In vitro Reprogramming of Fibroblasts into a Pluripotent ES-Cell-Like State," *Nature* 448:318-324 (2007) (Supplementary Pages Included).

Yu et al., "Human Induced Pluripotent Stem Cells Free of Vector and Transgene Sequences," *Science* 324:797-801 (2009).

Yu et al., "Induced Pluripotent Stem Cell Lines Derived from Human Somatic Cells," *Science* 318:1917-1920 (2007).

Zhou and Freed, "Adenoviral Gene Delivery Can Reprogram Human Fibroblasts to Induced Pluripotent Stem Cells," *Stem Cells* 27:2667-2674 (2009).

International Search Report for International Application No. PCT/JP2011/069588, mailed Nov. 29, 2011 (2 pages).

Supplementary European Search Report for European Patent Application No. 11821786.8, dated Feb. 10, 2014 (9 pages).

Nishimura et al., "Development of defective and persistent Sendai virus vector: a unique gene delivery/expression system ideal for cell programming," *J Biol Chem.* 286:4760-4771 (2011).

Tokusumi et al., "Recombinant Sendai viruses expressing different levels of a foreign reporter gene," *Virus Res.* 86:33-38 (2002).

Supporting Information for Carey et al., "Reprogramming of Murine and Human Somatic Cells Using a Single Polycistronic Vector," *Proc. Natl. Acad. Sci. USA* 106:157-162 (2009). (5 pages).

Supporting Online Material for Okita et al., "Generation of Mouse Induced Pluripotent Stem Cells Without Viral Vectors," *Science* 322:949-953 (2008). (19 pages).

COMPOSITION FOR INDUCING PLURIPOTENT STEM CELL, AND USE THEREOF

CROSS-REFERENCE TO RELATED APPLICATIONS

This application is the U.S. National Stage of the International Patent Application No. PCT/JP2011/069588, filed Aug. 30, 2011, which claims the benefit of Japanese Patent Application No. 2010-192752, filed Aug. 30, 2010.

TECHNICAL FIELD

The present invention relates to compositions for gene delivery used in the induction of pluripotent stem cells and uses thereof. Furthermore, the present invention relates to gene delivery vectors used in the induction of pluripotent stem cells. Specifically, the present invention relates to Sendai virus vectors incorporated in a specific order with genes encoding reprograming factors, compositions comprising these factors for gene delivery to be used in the induction of pluripotent stem cells, and uses thereof.

BACKGROUND ART

Since the reported induction of pluripotent stem cells (induced pluripotent stem (iPS) cells; also called as "artificial pluripotent stem cells" or "induced pluripotent stem cells") from somatic cells (Non-patent Document 1), iPS cells have been produced by introducing reprograming factors into various mammalian cells including human and mouse cells (Non-patent Documents 1 to 9). Many of them use retrovirus vectors to introduce reprograming factors. However, since retrovirus vectors carry the risk of tumorigenesis as a result of integration into the host genome, their use is limited (Non-patent Document 3). To solve this problem, attempts of inducing iPS cells using adenovirus vectors or plasmids have been made, but as long as DNA-type vectors are used, it is impossible to completely remove concerns over integration into the genome. Furthermore, the induction efficiency of iPS cells by these vectors is extremely low (Non-patent Documents 10 to 13).

To solve these problems, the present inventors have previously developed a system for inducing iPS cells using a Sendai virus vector which is an RNA-type virus (Patent Document 1). Induction efficiency of iPS cells using the Sendai virus vector was significantly higher than that in previous cases using other vectors. Since the Sendai virus vectors do not have a DNA phase during their lifecycle, there is no concern that they will become integrated into the host genome, and they are excellent in terms of safety. Also, the vectors can be easily removed after induction of iPS cells. However, techniques that use Sendai virus vectors for further increasing the induction efficiency of iPS cells are not known.

PRIOR ART DOCUMENTS

Patent Documents

[Patent Document 1] International Publication No. WO 2010/008054

Non-Patent Documents

[Non-patent Document 1] Takahashi, K. and Yamanaka, S. (2006) Cell 126, 663-676

[Non-patent Document 2] Maherali, N. et al., (2007) Cell Stem Cell 1, 55-70

[Non-patent Document 3] Okita, K. et al., (2007) Nature 448, 313-317

[Non-patent Document 4] Wernig, M. et al., (2007) Nature 448, 318-324

[Non-patent Document 5] Takahashi, K. et. al., (2007) Cell 131, 861-872

[Non-patent Document 6] Yu, J. et al., (2007) Science 318, 1917-1920

[Non-patent Document 7] Lowry, W. E. et al., (2008) Proc. Natl. Acad. Sci. USA 105, 2883-2888

[Non-patent Document 8] Park, I. H. et al., (2008) Nature 451, 141-146

[Non-patent Document 9] Masaki, H. et al., (2008) Stem Cell Res. 1, 105-115

[Non-patent Document 10] Stadtfeld, M. et al., (2008) Science 322, 945-949

[Non-patent Document 11] Okita, K. et al., (2008) Science 322, 949-953

[Non-patent Document 12] Yu, J. et al., (2009) Science 324, 797-801

[Non-patent Document 13] Zhou, W. et al., (2009) stem cells 27, 2667-2674

SUMMARY OF THE INVENTION

Problems to be Solved by the Invention

An objective of the present invention is to provide novel compositions for gene delivery used in the induction of pluripotent stem cells and uses thereof. Furthermore, an objective of the present invention is to provide novel gene delivery vectors used in the induction of pluripotent stem cells. Specifically, an objective of the present invention is to provide Sendai virus vectors incorporated in a specific order with genes encoding reprograming factors for inducing pluripotent stem cells, compositions comprising these vectors for gene delivery to be used in the induction of pluripotent stem cells, and uses thereof.

Means for Solving the Problems

The present inventors discovered that iPS cells can be induced at a significantly higher efficiency by using a Sendai virus vector in which the KLF gene, OCT gene, and SOX gene (i.e., reprogramming factors) are positioned on the Sendai virus genome, as compared to when these three genes are introduced using separate vectors. Furthermore, it was found that when this vector is used in combination with an MYC gene-expressing vector, iPS cells can be induced at a significantly high efficiency compared to when the KLF gene, OCT gene, and SOX gene are loaded into separate Sendai virus vectors. Alternatively, a vector that expresses the Glis1 gene (Maekawa et al., Nature, 474: 225-229, 2011) may be combined instead of the MYC gene-expressing vector.

In particular, the efficiency of iPS cell induction can be increased significantly by inserting into a single Sendai virus vector the KLF gene, OCT gene, and SOX gene in this order, or the OCT gene, SOX gene, and KLF gene in this order, and using the vector. Furthermore, when another Sendai virus vector that has an MYC gene inserted immediately upstream (immediately 3' side on the minus-strand RNA genome) of the Sendai virus L gene is used in combination, colonies of iPS cells appeared at an extremely high rate as shown in FIG. 1 (Condition 2). Furthermore, when using a vector into which the OCT gene, SOX gene, and KLF gene are inserted into a single Sendai virus vector in this order, a Sendai virus vector carrying the KLF gene can be combined in addition.

This way, the efficiency of iPS cell induction can be increased significantly by using a vector into which the KLF gene, OCT gene, and SOX gene are inserted into a single Sendai virus vector.

Specifically, the present invention relates to novel compositions for gene delivery used in the induction of pluripotent stem cells and uses thereof, as well as gene delivery vectors, and such, and more specifically relates to the inventions described in each of the claims. Inventions consisting of any combination of two or more inventions described in claims that cite the same claim are also inventions intended herein. More specifically, the present invention relates to the following:

[1] a composition for use in gene delivery for induction of a pluripotent stem cell, which comprises a Sendai virus vector into which the KLF gene, OCT gene, and SOX gene in this order, or the OCT gene, SOX gene, and KLF gene in this order are inserted immediately after the Sendai virus P gene;

[2] the composition of [1], which is used in combination with a different Sendai virus vector inserted with the MYC gene or Glis1 gene;

[3] the composition of [2], wherein the MYC gene or Glis1 gene is inserted immediately before the Sendai virus L gene;

[4] a method for producing a transgenic cell in the induction of a pluripotent stem cell, which comprises introducing into a cell a Sendai virus vector into which the KLF gene, OCT gene, and SOX gene in this order, or the OCT gene, SOX gene, and KLF gene in this order are inserted immediately after the Sendai virus P gene;

[5] the method of [4], which further comprises introducing into the cell another Sendai virus vector inserted with the MYC gene or Glis1 gene;

[6] the method of [5], wherein the MYC gene or Glis1 gene is inserted immediately before the Sendai virus L gene;

[7] a Sendai virus vector into which the KLF gene, OCT gene, and SOX gene in this order, or the OCT gene, SOX gene, and KLF gene in this order are inserted immediately after the Sendai virus P gene;

[8] a nucleic acid encoding a genome or an antigenome of the Sendai virus vector of [7];

[9] a kit for use in gene delivery for induction of a pluripotent stem cell, which comprises the Sendai virus vector of [7] and a different Sendai virus vector inserted with the MYC gene or Glis1 gene; and

[10] the kit of [9], wherein the MYC gene or Glis1 gene is inserted immediately before the Sendai virus L gene.

Any matters of the inventions described herein and any combination thereof are intended herein. In these inventions, inventions excluding any matters described herein, or any combinations thereof are also intended herein. Furthermore, certain specific embodiments described herein regarding the present invention not only disclose these embodiments, but also disclose inventions excluding these embodiments from generic inventions disclosed herein which include these embodiments.

Effects of the Invention

There is no concern that Sendai virus vectors will become integrated into a host genome, and thus they are very safe vectors. Therefore, if iPS cells can be induced at a higher efficiency by using these vectors, their practical utility is extremely high. The present invention enables one to further increase the induction efficiency of iPS cells by a Sendai virus vector, and at the same time accomplishes consolidation of multiple reprograming genes into a single Sendai virus vector, thereby contributing to the improvement of reproducibility and simplification of operations of iPS cell induction.

MODE FOR CARRYING OUT THE INVENTION

Figure 1:
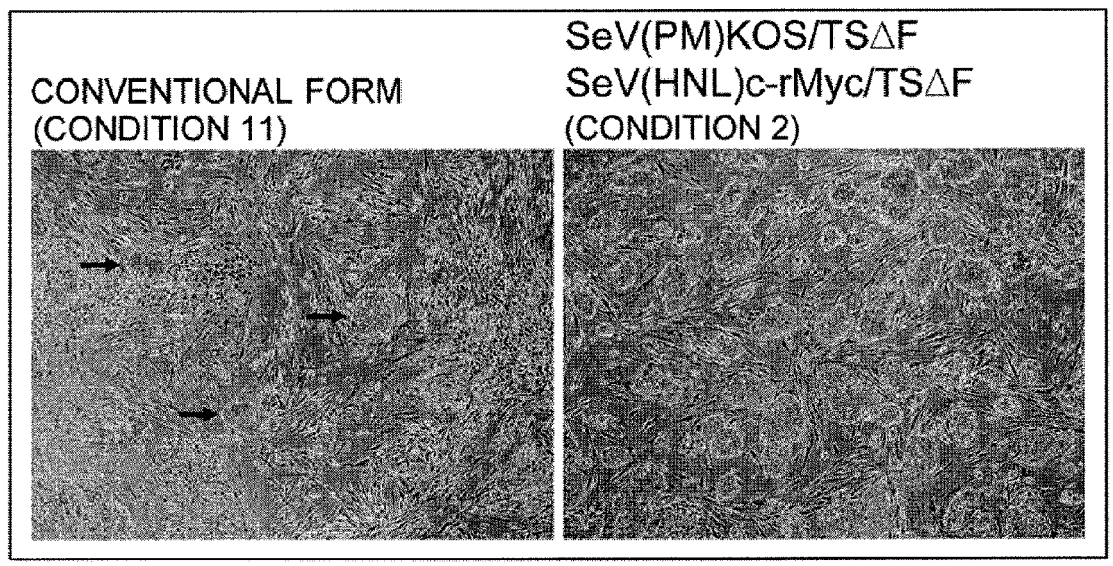
FIG. 1 shows the cell condition 14 days after vector infection. The left panel shows the case when a conventional vector was used (Condition 11), and the right panel shows the case when the vectors of the present invention were used (Condition 2).

Hereinafter, the mode for carrying out the present invention will be described in detail.

The present invention provides Sendai virus vectors incorporated with nuclear reprogramming factor (KLF, OCT, and SOX) genes in a specific order, and methods that use these vectors for delivering the reprogramming factor genes in the induction of reprogramming of differentiated cells, and in particular, methods for delivering the reprogramming factor genes in the production of pluripotent stem cells from somatic cells. Specifically, the methods comprise a step of contacting differentiated cells such as somatic cells with a Sendai virus vector incorporated with at least three genes encoding reprogramming factors, i.e., genes encoding KLF, OCT, and SOX in this order, or a Sendai virus vector incorporated with the OCT gene, SOX gene, and KLF gene in this order. More specifically, the present invention provides methods for delivering the reprogramming factor genes in cellular reprogramming, wherein the method comprises introducing the three reprogramming factor genes into cells in need thereof using the Sendai virus vector, and compositions comprising the Sendai virus vector for use in the method.

In the present invention, "pluripotent stem cells" refer to stem cells produced from the inner cell mass of an embryo of an animal in the blastocyst stage or cells having phenotypes similar to those cells. Specifically, pluripotent stem cells induced in the present invention are cells that express alkaline phosphatase which is an indicator of ES-like cells. Furthermore, preferably, when pluripotent stem cells are cultured, they form flat colonies containing cells with a higher proportion of nucleus volume than cytoplasm. Culturing may be carried out suitably with a feeder. Moreover, while cultured cells such as MEF stop proliferating in a few weeks, pluripotent stem cells can be passaged for a long period of time, and this can be confirmed based on their proliferative character that is not lost even when they are passaged, for example, 15 times or more, preferably 20 times or more, 25 times or more, 30 times or more, 35 times or more, or 40 times or more every three days. Furthermore, pluripotent stem cells preferably express endogenous OCT3/4 or Nanog, or more preferably, they express both of them. Furthermore, pluripotent stem cells preferably express TERT, and show telomerase activity (activity to synthesize telomeric repeat sequences). Moreover, pluripotent stem cells preferably have the ability to differentiate into three germ layers (the endoderm, mesoderm, and ectoderm) (for example, during teratoma formation and/or embryoid body formation). More preferably, pluripotent stem cells produce germline chimera when they are transplanted into blastocysts. Pluripotent stem cells capable of germline transmission are called germline-competent pluripotent stem cells. Confirmation of these phenotypes can be carried out by known methods (WO 2007/69666; Ichisaka T. et al., Nature 448 (7151): 313-7, 2007).

Furthermore, in the present invention, "differentiated" refers to that a differentiation stage of a cell is progressed more than before, and may refers to, for example, be more differentiated as compared to pluripotent stem cells, and includes states still possessing the ability to differentiate into multiple cell lineages (for example, somatic stem cells) and terminally differentiated states. Differentiated cells are cells (other than pluripotent stem cells) derived from pluripotent stem cells. Differentiated cells may be, for example, cells that do not have the ability to differentiate into the three germ layers (the endoderm, mesoderm, and ectoderm). Such cells will not have the ability to form the three germ layers unless they are reprogrammed. Furthermore, differentiated cells may be, for example, cells that cannot produce cells that are not of the germ layer type to which they belong. Differentiated cells may be somatic cells, and for example, they may be cells other than germ cells.

In the present invention, reprogramming refers to converting the differentiation state of a particular cell to a less differentiated state, and includes for example, dedifferentiation of differentiated cells, such as inducing cells with differentiation pluripotency, for example pluripotent stem cells, from cells without differentiation pluripotency. Furthermore, in the present invention, dedifferentiation refers to converting a particular cell into a more premature (for example, undifferentiated) state. Dedifferentiation may be reversion of a cell to its initial state or intermediate state in its path of differentiation. Furthermore, dedifferentiation may be a change from a cell unable to produce cells that are not of the same germ layer type to which the cell belongs, into a cell that can differentiate into other germ layer type cells. Dedifferentiation also includes, for example, cells not having triploblastic differentiation ability acquiring this triploblastic differentiation ability. Additionally, dedifferentiation includes the production of pluripotent stem cells.

Furthermore, in the present invention, somatic cells are, for example, cells other than pluripotent stem cells and germ cells. Somatic cells include, for example, multicellular organism-constituting cells other than pluripotent stem cells, and cultured cells thereof. Somatic cells include for example, somatic stem cells and terminally differentiated cells.

In the present invention, virus vectors are vectors having genomic nucleic acids derived from the virus, and that can express transgenes by incorporating the transgenes into the nucleic acids. Since Sendai virus vectors are chromosomally non-integrating virus vectors and expressed in the cytoplasm, there is no risk that the introduced gene will become integrated into the chromosome (nucleus-derived chromosome) of the host. Therefore, the vectors are safe and can be removed after completion of reprogramming. In the present invention, Sendai virus vectors include infectious virus particles, as well as complexes of the viral core, viral genome, and viral proteins, and complexes comprising non-infectious viral particles and such, which are complexes having the ability to express loaded genes upon introduction into cells. For example, in Sendai viruses, ribonucleoproteins (the viral core portion) consisting of a Sendai virus genome and bound Sendai virus proteins (NP, P, and L proteins) can express transgenes in cells when they are introduced into cells (WO 00/70055). Introduction into cells can be appropriately carried out using transfection reagents and the like. Such ribonucleoproteins (RNPs) are also included in the Sendai virus vectors of the present invention.

Sendai virus is a Mononegavirales virus, belongs to Paramyxoviridae (including the genera Paramyxovirus, Morbillivirus, Rubulavirus, and Pneumovirus), and contains a single-stranded minus-strand (antisense strand of a viral protein-encoding sense strand) RNA as the genome. Minus-strand RNA is also called negative-strand RNA.

Mononegavirales includes viruses belonging to families such as Rhabdoviridae (including the genera Vesiculovirus, Lyssavirus, and Ephemerovirus), and Filoviridae, in addition to Paramyxovirus (Paramyxoviridae virus) (Virus, vol. 57, No. 1: pp 29-36, 2007; Annu. Rev. Genet. 32, 123-162, 1998; Fields virology fourth edition, Philadelphia, Lippincott-Raven, 1305-1340, 2001; Microbiol. Immunol. 43, 613-624, 1999; Field Virology, Third edition pp. 1205-1241, 1996). Other examples of Paramyxoviridae virus other than Sendai virus include Newcastle disease virus, mumps virus, measles virus, respiratory syncytial virus (RS virus), rinderpest virus, distemper virus, simian parainfluenza virus (SV5), and human parainfluenza viruses I, II, and III; influenza virus belonging to the Orthomyxoviridae family; and the vesicular stomatitis virus and Rabies virus belonging to the Rhabdoviridae family. Further examples include Sendai virus (SeV), human parainfluenza virus-1 (HPIV-1), human parainfluenza virus-3 (HPIV-3), phocine distemper virus (PDV), canine distemper virus (CDV), dolphin molbillivirus (DMV), peste-des-petits-ruminants virus (PDPR), measles virus (MV), rinderpest virus (RPV), Hendra virus (Hendra), Nipah virus (Nipah), human parainfluenza virus-2 (HPIV-2), simian parainfluenza virus 5 (SV5), human parainfluenza virus-4a (HPIV-4a), human parainfluenza virus-4b (HPIV-4b), mumps virus (Mumps), and Newcastle disease virus (NDV). More preferably, examples include viruses selected from the group consisting of Sendai virus (SeV), human parainfluenza virus-1 (HPIV-1), human parainfluenza virus-3 (HPIV-3), phocine distemper virus (PDV), canine distemper virus (CDV), dolphin molbillivirus (DMV), peste-des-petits-ruminants virus (PDPR), measles virus (MV), rinderpest virus (RPV), Hendra virus (Hendra), and Nipah virus (Nipah).

For examples of accession numbers in the database for the nucleotide sequences of Sendai virus genes, see M29343, M30202, M30203, M30204, M51331, M55565, M69046, and X17218 for the NP gene; M30202, M30203, M30204, M55565, M69046, X00583, X17007, and X17008 for the P gene; D11446, K02742, M30202, M30203, M30204, M69046, U31956, X00584, and X53056 for the M gene; D00152, D11446, D17334, D17335, M30202, M30203, M30204, M69046, X00152, and X02131 for the F gene; D26475, M12397, M30202, M30203, M30204, M69046, X00586, X02808, and X56131 for the FIN gene; and D00053, M30202, M30203, M30204, M69040, X00587, and X58886 for the L gene. Examples of viral genes encoded by other viruses include CDV, AF014953; DMV, X75961; HPIV-1, D01070; HPIV-2, M55320; HPIV-3, D10025; Mapuera, X85128; Mumps, D86172; MV, K01711; NDV, AF064091; PDPR, X74443; PDV, X75717; RPV, X68311; SeV, X00087; SV5, M81442; and Tupaia, AF079780 for the NP gene (also referred to as the N gene); CDV, X51869; DMV, Z47758; HPIV-1, M74081; HPIV-3, X04721; HPIV-4a, M55975; HPIV-4b, M55976; Mumps, D86173; MV, M89920; NDV, M20302; PDV, X75960; RPV, X68311; SeV, M30202; SV5, AF052755; and Tupaia, AF079780 for the P gene; CDV, AF014953; DMV, Z47758; HPIV-1. M74081; HPIV-3, D00047; MV, AB016162; RPV, X68311; SeV, AB005796; and Tupaia, AF079780 for the C gene; CDV, M12669; DMV 230087; HPIV-1, 538067; HPIV-2, M62734; HPIV-3, D00130; HPIV-4a, D10241; HPIV-4b, D10242; Mumps, D86171; MV, AB012948; NDV, AF089819; PDPR, Z47977; PDV, X75717; RPV, M34018; SeV, U31956; and SV5, M32248 for the M gene; CDV, M21849; DMV, AJ224704; HPN-1, M22347; HPIV-2, M60182; HPIV-3. X05303, HPIV-4a, D49821; HPIV-4b, D49822; Mumps, D86169; MV, AB003178; NDV, AF048763; PDPR, Z37017; PDV, AJ224706; RPV, M21514; SeV, D17334; and SV5, AB021962 for the F gene; and CDV, AF112189; DMV, AJ224705; HPIV-1, U709498; HPIV-2. D000865; HPIV-3, AB012132; HPIV-4A, M34033; HPIV-4B, AB006954; Mumps, X99040; MV, K01711; NDV, AF204872; PDPR, Z81358; PDV, Z36979; RPV, AF132934; SeV, U06433; and SV-5, 576876 for the HN(H or G) gene. However, multiple strains are known for each of the viruses, and genes consisting of a sequence other than those exemplified above may exist due to strain differences. Sendai virus vectors carrying viral genes derived from any of these genes are useful as vectors of the present invention. For example, Sendai virus vectors of the present invention comprise a nucleotide sequence having 90% or higher, preferably 95% or higher, 96% or higher, 97% or higher, 98% or higher, or 99% or higher identity to the coding sequence of any of the above-mentioned viral genes. Furthermore, the Sendai virus vectors of the present invention comprise, for example, a nucleotide sequence encoding an amino acid sequence having 90% or higher, preferably 95% or higher, 96% or higher, 97% or higher, 98% or higher, or 99% or higher identity to an amino acid sequence encoded by the coding sequence of any one of the above-mentioned viral genes. Furthermore, Sendai virus vectors of the present invention comprise, for example, a nucleotide sequence encoding an amino acid sequence with ten or less, preferably nine or less, eight or less, seven or less, six or less, five or less, four or less, three or less, two or less, or one amino acid substitutions, insertions, deletions, and/or additions in an amino acid sequence encoded by the coding sequence of any one of the above-mentioned viral genes.

The sequences referenced by the database accession numbers such as the nucleotide sequences and amino acid sequences described herein refer to sequences on, for example, the filing date and priority date of this application, and can be identified as sequences at the time of either the filing date or priority date of the present application, and are preferably identified as sequences on the filing date of this application. The sequences at the respective time points can be identified by referring to the revision history of the database.

The Sendai virus vectors used in the present invention may be derivatives, and the derivatives comprise viruses with modified viral genes, and chemically modified viruses, and such, so that the ability of the virus to introduce genes is not impaired.

Furthermore, Sendai viruses may be derived from natural strains, wild-type strains, mutant strains, laboratory-passaged strains, and artificially constructed strains and such. An example is the Z strain (Medical Journal of Osaka University Vol. 6, No. 1, March 1955 p 1-15). That is, these viruses may be virus vectors having similar structures as viruses isolated from nature, or viruses artificially modified by genetic recombination, as long as the desired reprogramming can be induced. For example, they may have mutations or deletions in any of the genes of the wild-type virus. Furthermore, incomplete viruses such as DI particles (J. Virol. 68: 8413-8417, 1994) may also be used. For example, viruses having a mutation or deletion in at least one gene encoding a viral envelope protein or a coat protein can be preferably used. Such virus vectors are, for example, virus vectors that can replicate the genome in infected cells but cannot form infectious virus particles. Since there is no worry of spreading the infection to the surroundings, such transmission-defective virus vectors are highly safe. For example, minus-strand RNA viruses that do not contain at least one gene encoding an envelope protein such as F and/or HN or a spike protein, or a combination thereof may be used (WO 00/70055 and WO 00/70070; Li, H.-O. et al., J. Virol. 74(14): 6564-6569 (2000)). If proteins necessary for genome replication (for example, N, P, and L proteins) are encoded in the genomic RNA, the genome can be amplified in infected cells. To produce defective type of viruses, for example, the defective gene product or a protein that can complement it is externally supplied in the virus-producing cell (WO 00/70055 and WO 00/70070; Li, H.-O. et al., J. Virol. 74(14): 6564-6569 (2000)). Furthermore, a method of collecting virus vectors as noninfective virus particles (VLP) without completely complementing the defective viral protein is also known (WO 00/70070). Furthermore, when virus vectors are collected as RNPs (for example, RNPs containing the N, L, and P proteins and genomic RNA), vectors can be produced without complementing the envelope proteins.

Furthermore, the use of virus vectors carrying a mutant viral protein gene is also preferred. The present invention particularly provides methods of gene delivery in reprogramming, methods for producing reprogrammed cells, compositions, and kits using Sendai virus vectors having mutations and/or deletions in the viral gene. For example, in the envelope protein and coat proteins, many mutations including attenuation mutations and temperature-sensitive mutations are known. Sendai viruses having these mutant protein genes can be used favorably in the present invention. In the present invention, vectors with lowered cytotoxicity are desirably used. Cytotoxicity can be measured, for example by quantifying the release of lactic acid dehydrogenase (LDH) from cells. For example, vectors with significantly lowered cytotoxicity compared to the wild type can be used. Regarding the degree of lowering of cytotoxicity, for example, vectors showing a significant decrease of, for example 20% or more, 25% or more, 30% or more, 35% or more, 40% or more, or 50% or more in the LDH release level compared to the wild-type in a culture medium of human-derived HeLa cell (ATCC CCL-2) or simian-derived CV-1 cell (ATCC CCL 70) infected at MOI (multiplicity of infection) 3 and cultured for three days can be used. Furthermore, mutations that decrease cytotoxicity also include temperature-sensitive mutations. Temperature-sensitive mutations refer to mutations which significantly decrease the activity at the viral host's ordinary temperature (for example, 37° C. to 38° C.) when compared to that at a low temperature (for example, 30° C. to 32° C.). Such proteins with temperature-sensitive mutations are useful since the viruses can be produced under permissive temperatures (low temperatures). When infected at 37° C., the virus vectors having useful temperature-sensitive mutations in the present invention show, a growth rate or gene expression level of, for example, ½ or less, preferably ⅓ or less, more preferably ⅕ or less, more preferably ¹/₁₀ or less, and more preferably ¹/₂₀ or less compared to when cultured cells are infected at 32° C.

A Sendai virus vector used in the present invention may be a wild type as long as it does not inhibit reprogramming and can induce reprogramming by reprogramming factors or support induction of reprogramming, and has deletions or mutations in preferably at least one, more preferably at least 2, 3, 4, 5, or more viral genes. Deletions and mutations may be arbitrarily combined and introduced to each of the genes. Herein, a mutation may be a function-impairing mutation or a temperature-sensitive mutation, and is a mutation that decreases the viral proliferation rate or the expression level of any of the carried gene to preferably ½ or less, more preferably ⅓ or less, more preferably ⅕ or less, more preferably ¹/₁₀ or less, and more preferably ¹/₂₀ or less compared to the wild type at least at 37° C. The use of such modified virus vectors can be useful particularly for the induction of pluripotent stem cells. For example, Sendai virus vectors used favorably in the present invention have at least two deleted or mutated viral genes. Such viruses include those with deletions of at least two viral genes, those with mutations in at least two viral genes, and those with a mutation in at least one viral gene and a deletion of at least one viral gene. The at least two mutated or deleted viral genes are preferably genes encoding envelope-constituting proteins. For example, vectors with deletion of the F gene with further deletion of the M and/or the HN gene or further mutation (for example, temperature-sensitive mutation) in the M and/or the FIN gene are used favorably in the present invention. Furthermore, for example, vectors with deletion of the F gene with further deletion of the M or the HN gene and further mutation in the remaining M and/or HN gene (for example, temperature-sensitive mutation) are also used favorably in the present invention. Vectors used in the present invention more preferably have at least three deleted or mutated viral genes (preferably at least three genes encoding envelope-constituting proteins; F, HN, and M). Such virus vectors include those with deletion of at least three genes, those with mutations in at least three genes, those with mutations in at least one gene and deletion of at least two genes, and those with mutations in at least two genes and deletion of at least one gene. As examples of more preferred embodiments, vectors with deletion of the F gene with further deletion of the M and the FIN gene or further mutations (for example, temperature-sensitive mutations) in the M and the HN gene are used favorably in the present invention. Furthermore, for example, vectors with deletion of the F gene with further deletion of the M or the FIN gene and further mutation in the remaining M or HN gene (for example, temperature-sensitive mutation) are used favorably in the present invention. Such mutated-form viruses can be produced according to known methods. For example, a temperature-sensitive mutation of the M gene of Sendai virus includes amino acid substitution of a site arbitrarily selected from the group consisting of position 69 (G69), position 116 (T116), and position 183 (A183) of the M protein (Inoue, M. et al., J. Virol. 2003, 77: 3238-3246). Viruses having a genome encoding a mutant M protein, in which the amino acids of any one site, preferably a combination of any two sites, or more preferably all three sites of the three sites mentioned above are substituted in the Sendai virus M proteins to other amino acids, are used preferably in the present invention.

Preferred amino acid mutations are substitution to other amino acids with a side chain having different chemical properties, and examples are substitution to an amino acid with a BLOSUM62 matrix (Henikoff, S, and Henikoff, J. G. (1992) Proc. Natl. Acad. Sci. USA 89: 10915-10919) score of three or less, preferably two or less, more preferably one or less, and even more preferably 0. Specifically, G69, T116, and A 183 of the Sendai virus M protein can be substituted to Glu (E), Ala (A), and Ser (S), respectively. Alternatively, mutations homologous to mutations in the M protein of the temperature-sensitive P253-505 measles virus strain (Morikawa, Y. et al., Kitasato Arch. Exp. Med. 1991, 64: 15-30) can also be used. Mutations can be introduced according to known mutation methods, for example, using oligonucleotides and such.

Furthermore, examples of temperature-sensitive mutations in the HN gene include amino acid substitution of a site arbitrarily selected from the group consisting of position 262 (A262), position 264 (G264), and position 461 (K461) of the HN protein of a Sendai virus (Inoue, M. et al., J. Virol. 2003, 77: 3238-3246). Viruses having a genome encoding a mutant HN protein in which the amino acids of any one of the three sites, preferably a combination of any two sites, or more preferably all three sites are substituted to other amino acids are used preferably in the present invention. As mentioned above, preferred amino acid substitutions are substitutions to other amino acids with a side chain having different chemical properties. As a preferred example, A262, G264, and K461 of the Sendai virus HN protein are substituted to Thr (T), Arg (R), and Gly (G), respectively. Furthermore, for example, using the temperature-sensitive vaccine strain Urabe AM9 of the mumps virus as a reference, amino acids at positions 464 and 468 of the HN protein can be mutated (Wright, K. E. et al., Virus Res. 2000, 67: 49-57).

Furthermore, Sendai viruses may have mutations in the P gene and/or the L gene. Examples of such mutations are specifically, mutation of Glu at position 86 (E86) in the SeV P protein, and substitution of Leu at position 511 (L511) in the SeV P protein to other amino acids. As mentioned above, preferred amino acid substitutions are substitutions to other amino acids with a side chain having different chemical properties. Specific examples include substitution of the amino acid at position 86 to Lys, and substitution of the amino acid at position 511 to Phe. Furthermore, examples in the L protein include substitution of Asn at position 1197 (N1197) and/or Lys at position 1795 (K1795) in the SeV L protein to other amino acids, and similarly as above, preferred amino acid substitutions are substitutions to other amino acids with a side chain having different chemical properties. Specific examples are substitution of the amino acid at position 1197 to Ser, and substitution of the amino acid at position 1795 to Glu. Mutations of the P gene and L gene can significantly increase the effects of sustained infectivity, suppression of release of secondary particles, or suppression of cytotoxicity. Further, combination of mutations and/or deletions of envelope protein genes can dramatically increase these effects. Furthermore, examples for the L gene include substitution of Tyr at position 1214 (Y1214) and/or substitution of Met at position 1602 (M1602) of the SeV L protein to other amino acids, and similarly as above, preferred amino acid substitutions are substitutions to other amino acids with a side chain having different chemical properties. Specific examples are substitution of the amino acid at position 1214 to Phe, and substitution of the amino acid at position 1602 to Leu. The above-mentioned mutations can be arbitrarily combined.

For example, Sendai virus vectors in which at least G at position 69, T at position 116, and A at position 183 of the SeV M protein, at least A of position 262, G of position 264, and K of position 461 of the SeV HN protein, at least L of position 511 of the SeV P protein, and at least N of position 1197 and K of position 1795 of the SeV L protein are each substituted to other amino acids, and in which the F gene is also deficient or deleted; and F-gene-deleted or -deficient Sendai virus vectors whose cytotoxicity is similar to or lower than those mentioned above and/or whose temperature sensitivity is similar to or higher than those mentioned above are particularly preferred for the expression of nuclear reprogramming factors in the present invention. Specific examples of the substitutions include G69E, T116A, and A183S substitutions for the M protein, A262T, G264R, and K461G substitutions for the HN protein, L511F substitution for the P protein, and N1197S and K1795E substitutions for the L protein.

Examples of mutations of the L protein include substitutions of an amino acids at sites arbitrarily selected from position 942 (Y942), position 1361 (L1361), and position 1558 (L1558) of the SeV L protein to other amino acids. Similarly as above, preferred amino acid substitutions are substitutions to other amino acids with a side chain having different chemical properties. Specific examples include substitution of the amino acid at position 942 to H is, substitution of the amino acid at position 1361 to Cys, and substitution of the amino acid at position 1558 to Ile. In particular, the L protein with substitutions at least at positions 942 or 1558 can be used preferably. For example, mutant L proteins in which, in addition to position 1558, position 1361 is also substituted to another amino acid are preferred as well. Furthermore, mutant L proteins in which, in addition to position 942, position 1558 and/or position 1361 are also substituted to other amino acids are favorable as well. These mutations can increase the temperature sensitivity of the L protein.

Examples of mutations of the P protein include substitutions of amino acids at sites arbitrarily selected from position 433 (D433), position 434 (R434), and position 437 (K437) of the SeV P protein to other amino acids. Similarly as above, preferred amino acid substitutions are substitutions to other amino acids with a side chain having different chemical properties. Specific examples include substitution of the amino acid at position 433 to Ala (A), substitution of the amino acid at position 434 to Ala (A), and substitution of the amino acid at position 437 to Ala (A). In particular, P proteins in which all three of these sites are substituted can be used preferably. These mutations can increase the temperature sensitivity of the P protein.

F-gene-deleted or -deficient Sendai virus vectors encoding a mutant P protein in which at least at the three positions of D at position 433, R at position 434, and K at position 437 of the SeV P protein are substituted to other amino acids, and a mutant L protein in which at least the L at position 1558 of the SeV L protein is substituted (preferably a mutant L protein in which at least the L at position 1361 is also substituted to another amino acid); and F-gene-deleted or -deficient Sendai virus vectors whose cytotoxicity is similar to or lower than those mentioned above and/or whose temperature sensitivity is similar to or higher than those mentioned above are used preferably in the present invention. In addition to the above-mentioned mutations, each of the viral proteins may have mutations on other amino acids (for example, on ten or less, five or less, four or less, three or less, two or less, or one amino acid). Since vectors comprising the above-mentioned mutations show a high temperature sensitivity, after completion of reprogramming, the vectors can be removed easily by culturing the cells at a slightly high temperature (for example, 37.5° C. to 39° C. preferably 38° C. to 39° C., or 38.5° C. to 39° C.).

More specifically, for example, Sendai virus vectors having mutations such as:
TS 7: L (Y942H/L1361C/L15581);
TS 12: P (D433A/R434A/K437A);
TS 13: P (D433A/R434A/K437A), L (L15581);
TS 14: P (D433A/R434A/K437A), L (L1361C); and
TS 15: P (D433A/R434A/K437A), L (L1361C/L15581) can be used favorably (International Publication No. WO 2010/008054).

Specific vectors may be, for example, an F gene-deleted Sendai virus vector in which the M protein has G69E, T116A, and A183S mutations; the HN protein has A262T, G264R, and K461G mutations; the P protein has L511F mutation; and the L protein has N1197S and K1795E mutations (for example, Z strain); and vectors produced by further introducing a TS 7, TS 12, TS 13, TS 14, or TS 15 mutation into this vector are more preferred. Specifically, examples include SeV18+/TSΔF (WO 2010/008054 and WO 2003/025570) and SeV(PM)/TSΔF, and vectors produced by further introducing a TS 7, TS 12, TS 13, TS 14, or TS 15 mutation into these vectors, but are not limited thereto.

"TSΔF" means carrying G69E, T116A, and A183S mutations in the M protein, A262T, G264R, and K461G mutations in the HN protein, L511F mutation in the P protein, and N1197S and K1795E mutations in the L protein, and deletion of the F gene. In particular, examples of preferred vectors include SeV(PM)KOS/TSΔF, SeV(PM)KOS/TS7ΔF, SeV (PM)KOS/TS12ΔF, and SeV(PM)OSK/TSΔF, but are not limited thereto. In this case, the MYC gene can be introduced using SeV(HNL)c-rMYC/TS12ΔF, SeV(HNL)c-rMYC/TS13ΔF, SeV(HNL)c-rMYC/TS15ΔF, or such. Furthermore, a KLF gene-expressing Sendai virus vector may be introduced additionally. Specifically, favorable results can be obtained by combining with a Sendai virus vector carrying the OCT gene, SOX gene, and KLF gene in this order. The KLF gene can be inserted upstream of the Sendai virus vector N gene (3' side of the N gene on the genome). As desired F gene-deleted vector and/or -mutated vector described herein may be used as the vector; and a specific example is SeV18+KLF4/TSΔF, but it is not limited thereto.

Specifically, the present invention also provides:

[1] a composition for use in gene delivery in the induction of a pluripotent stem cell, which comprises a Sendai virus vector with insertion of the OCT gene, SOX gene, and KLF gene in this order immediately after the Sendai virus P gene, which is a composition used in combination with a different Sendai virus vector inserted with the KLF gene;

[2] the composition of [1], which is used in combination with a different Sendai virus vector inserted with the MYC gene or Glis1 gene;

[3] the composition of [2], wherein the MYC gene or Glis1 gene is inserted immediately before the Sendai virus L gene;

[4] a method for producing a transgenic cell in the induction of a pluripotent stem cell, wherein the method comprises introducing into a cell a Sendai virus vector with insertion of the OCT gene, SOX gene, and KLF gene in this order immediately after the Sendai virus P gene, and a different Sendai virus vector inserted with the KLF gene;

[5] the method of [4], which further comprises introducing into the cell a different Sendai virus vector with insertion of the MYC gene or Glis1 gene;

[6] the method of [5], wherein the MYC gene or Glis1 gene is inserted immediately before the Sendai virus L gene;

[7] a kit for use in gene delivery in the induction of a pluripotent stem cell, which comprises a Sendai virus vector inserted with the OCT gene, SOX gene, and KLF gene in this order, immediately after the Sendai virus P gene, and a different Sendai virus vector inserted with the KLF gene;

[8] the kit of [7], which comprises a different Sendai virus vector inserted with the MYC gene or Glis1 gene; and

[9] the kit of [8], wherein the MYC gene or Glis1 gene is inserted immediately before the Sendai virus L gene.

The cytotoxicity of vectors can be measured, for example, by quantifying the release of lactate dehydrogenase (LDH) from cells. Specifically, for example, HeLa (ATCC CCL-2) or simian CV-1 (ATCC CCL70) is infected at MOI 3, and the amount of LDH released into the culture solution after three days of culture is measured. The lower the amount of LDH released, the lower the cytotoxicity. Furthermore, temperature sensitivity can be determined by measuring the speed of viral proliferation or the expression level of the loaded gene at the viral host's ordinary temperature (for example, 37° C. to 38° C.). The lower the speed of viral proliferation and/or expression level of the loaded gene as compared to those without mutations, the higher the temperature sensitivity is judged to be.

Furthermore, when using an envelope virus, a virus containing a protein in the envelope that is different from the envelope protein originally carried by the virus may be used. For example, by expressing a desired exogenous envelope protein in a virus-producing cell when producing the virus, a virus containing this protein can be produced. Such proteins are not particularly limited and desired proteins, such as adhesion factors, ligands, and receptors that confer an ability to infect to mammalian cells are used. Specific examples include the G protein of vesicular stomatitis virus (VSV) (VSV-G). The VSV-G protein may be derived from any VSV strain, and for example, VSV-G protein derived from the Indiana serotype strain (J. Virology 39: 519-528 (1981)) may be used, but it is not limited thereto. Sendai virus vector used in the present invention can include arbitrary combinations of other virus-derived envelope proteins.

Reconstitution of recombinant Sendai viruses carrying nuclear reprogramming factors can be carried out using known methods. As specific procedures, typically, Sendai virus can be produced by the steps of (a) transcribing a cDNA encoding the Sendai virus genomic RNA (minus strand) or a complementary strand thereof (plus strand) in a cell that expresses viral proteins (N, P, and L) necessary for virus particle formation, and (b) collecting a culture supernatant containing the produced viruses. Viral proteins necessary for particle formation may be expressed from the transcribed viral genomic RNA, or they may be provided in trans from sources other than genomic RNA. For example, they can be provided by introducing expression plasmids encoding the N, P, and L proteins into cells. When viral genes necessary for particle formation are lacking in the genomic RNA, those viral genes may be separately expressed in virus-producing cells to complement particle formation. To express the viral proteins or the RNA genome in cells, vectors having a DNA encoding such proteins or genomic RNA linked downstream of a suitable promoter that functions in a host cell is introduced into the host cell. The transcribed genomic RNA is replicated in the presence of viral proteins, and infectious virus particles are formed. When producing a defective type of virus lacking genes such as those of the envelope proteins, the missing protein, other viral proteins that can complement the function of those proteins, or such may be expressed in the virus-producing cells.

For example, production of Sendai virus can be carried out by using the following known methods (WO 97/16539; WO 97/16538; WO 00/70055; WO 00/70070; WO 01/18223; WO 03/025570; WO 2005/071092; WO 2006/137517; WO 2007/083644; WO 2008/007581; Hasan, M. K. et al., J. Gen. Virol. 78: 2813-2820, 1997; Kato, A. et al., 1997, EMBO J. 16: 578-587; and Yu, D. et al., 1997, Genes Cells 2: 457-466; Durbin, A. P. et al., 1997, Virology 235: 323-332; Whelan, S. P. et al., 1995, Proc. Natl. Acad. Sci. USA 92: 8388-8392; Schnell. M. J. et al., 1994, EMBO J. 13: 4195-4203; Radecke, F. et al., 1995, EMBO J. 14: 5773-5784; Lawson, N. D. et al., Proc. Natl. Acad. Sci. USA 92: 4477-4481; Garcin, D. et al., 1995, EMBO J. 14: 6087-6094; Kato, A. et al., 1996, Genes Cells 1: 569-579; Baron, M. D. and Barrett, T., 1997, J. Virol. 71: 1265-1271; Bridgen, A. and Elliott, R. M., 1996, Proc. Natl. Acad. Sci. USA 93: 15400-15404; Tokusumi, T. et al., Virus Res. 2002, 86: 33-38; Li, H.-O. et al., J. Virol. 2000, 74: 6564-6569). Regarding methods for proliferation of viruses and methods for producing recombinant viruses, see also "Uirusu-gaku Jikken-gaku Kakuron (Detailed Virology Experiments)", second revised edition (National Institute of Infectious Diseases Students Institute edition, Maruzen, 1982).

Into the above-mentioned Sendai virus, the KLF gene, OCT gene, and SOX gene are incorporated in this order, or they are incorporated in the order of the OCT gene, SOX gene, and KLF gene. Generally, these foreign genes can be inserted immediately before (3' side on the genome) or immediately after (5' side on the genome of) any of the viral genes (NP, P, M, F, HN, or L). Preferably, the KLF gene, OCT gene, and SOX gene in this order, or the OCT gene, SOX gene, and KLF gene in this order are incorporated immediately after the Sendai virus P gene, i.e., immediately downstream of the P gene (immediately 5' side on the minus-strand RNA genome). For example, in the former order, a transcription initiation signal (S sequence), a transcription termination signal (E sequence), and a spacer sequence (intervening sequence (I sequence) and such) may be included between the P gene and the KLF gene (in the latter case, between the P gene and the OCT gene); however other transcription units (for example, transcription units encoding protein-coding genes) are not included. Since the Sendai virus carries a minus-strand RNA as the genome, opposite to the usual, the 3' side corresponds to the upstream and the 5' side corresponds to the downstream of the genome. When the KLF gene, OCT gene, and SOX gene are positioned in this order in the Sendai virus genome, among the three genes the KLF gene is positioned closest to the 3' side, and the SOX gene is positioned closest to the 5' side. Since the minus-strand RNA encodes genes in the antisense orientation, the KLF gene, OCT gene, and SOX gene are encoded as an antisense strand on the genome and not as a protein-coding strand (sense strand). When the Sendai virus genome enters a cell, it produces an antigenomic RNA using this genome as template. Antigenome is a plus strand, and the KLF gene, OCT gene and SOX gene are loaded as a protein-coding strand (sense strand). In antigenomic RNA, the KLF gene, OCT gene, and SOX gene are positioned so that among the three genes, the KLF gene is positioned closest to the 5' side and the SOX gene is positioned closest to the 3' side.

The three genes are preferably adjacent to each other (i.e., with no other genes interposed among the three genes). Each of the genes may be appropriately sandwiched between the Sendai virus S (Start) sequence and the E (End) sequence. The S sequence is a signal sequence that initiates transcription, and the E sequence terminates the transcription. The region between the S sequence and the E sequence becomes a single transcription unit. Where appropriate, a sequence that serves as a spacer (intervening sequence) can be inserted between the E sequence of a certain gene and the S sequence of the next gene. For example, a Sendai virus vector that contains a nucleic acid having the constitution of S-KLF gene-E-I-S-OCT gene-E-I-S-SOX gene-E (S, I, and E refer to the S sequence, the I (intervening) sequence, and the E sequence, respectively) in its genome can be used favorably. The P gene and KLF gene on the Sendai virus genome will be linked in the following manner: P gene-E-1-S-KLF gene-, and such.

When the OCT gene, SOX gene, and KLF gene are positioned in this order, for example, a Sendai virus vector that contains a nucleic acid having the constitution of S-OCT gene-E-I-S-SOX gene-E-1-S-KLF gene-E (S, I, and E refer to the S sequence, the I (intervening) sequence, and the E sequence, respectively) in its genome can be used favorably. The P gene and SOX gene on the Sendai virus genome will be linked in the following manner: P gene-E-I-S-SOX gene-, and so on.

While a desired S sequence of Sendai virus may be used as the S sequence, for example, the 3'-UCCCWVUUWC-5' (W=A or U; V=A, C, or G) sequence (SEQ ID NO: 1) may be used favorably. In particular, 3'-UCCCAGUUUC-5' (SEQ ID NO: 2), 3'-UCCCACUUAC-5' (SEQ ID NO: 3), and 3'-UCCCACUUUC-5' (SEQ ID NO: 4) are preferred. When these sequences are presented as DNA sequences encoding the plus strand, they are 5'-AGGGTCAAAG-3' (SEQ ID NO: 5), 5'-AGGGTGAATG-3' (SEQ ID NO: 6), and 5'-AGGGTGAAAG-3' (SEQ ID NO: 7), respectively. An E sequence of the Sendai virus vector is preferably, for example, 3'-AUUCUUUUU-5' (SEQ ID NO: 8) (the plus strand-encoding DNA is 5'-TAAGAAAAA-3' (SEQ ID NO: 9)). The I sequence may be, for example, any three bases, and specifically, 3'-GAA-5' (5'-CTT-3' in the plus strand DNA) may be used.

The genome of wild-type Sendai virus includes a short 3' leader region followed by a nucleocapsid (NP) gene, a phospho (P) gene, a matrix (M) gene, a fusion (F) gene, a hemagglutinin-neuraminidase (HN) gene, and a large (L) gene, and then a short 5' trailer region, in this order. Viral genes can be positioned in this order in Sendai virus vectors as well. Production of recombinant vectors comparable to wild-type viruses, and various mutant vectors are already known. Furthermore, it has been shown that gene delivery is possible using the RNP alone without its envelope (WO 00/70055). Therefore, reprogramming can be carried out using Sendai virus RNP as a virus vector.

Sendai viruses are sufficiently functional as vectors if they carry the NP gene, P gene and L gene; and they can replicate genome in cells and express the loaded foreign genes (KLF, OCT, and SOX). In a Sendai virus carrying the three genes, NP gene, P gene and L gene as viral genes, the set of KLF, OCT, and SOX genes is inserted, for example, between the P gene and the L gene. In a vector containing the M gene, the set of KLF, OCT, and SOX genes is inserted, for example, between the P gene and the M gene (WO 97/16539). When the F gene is included in an M gene-deleted Sendai virus vector, the set of KLF, OCT, and SOX genes is inserted between the P gene and the F gene (WO 00/70070). For the M and F gene-deleted Sendai virus vector, the position of insertion is between the P gene and the FIN gene; and for the F, M, and HN gene-deleted Sendai virus vector, the position of insertion is between the P gene and the L gene (WO 2003/025570, WO 2006/137517). Viral gene-deleted vectors are preferable since they are very safe. In the present invention, a vector having at least the F gene deletion can be preferably used.

The above-mentioned Sendai virus containing the KLF, OCT, and SOX genes can be appropriately used alone for gene delivery in reprogramming, but it is more preferably used in reprogramming that further involves introduction of the MYC gene or Glis1 gene. The MYC gene or Glis1 gene can be inserted into the above-mentioned Sendai virus vector containing the KLF, OCT and SOX genes, but it may also be used after insertion into a different vector. When inserting the MYC gene or Glis1 gene into a different vector, desired vectors such as plasmids, virus vectors, and non-virus vectors (for example, liposomes) can be used. Examples of virus vectors include Adenovirus vectors and retrovirus vectors, but are not limited thereto. More preferably, the MYC gene or Glis1 gene is inserted into a Sendai virus vector. In the present invention, the above-mentioned Sendai virus containing the KLF, OCT, and SOX genes is preferably used in combination with a different Sendai virus vector inserted with the MYC gene or Glis1 gene. The above-mentioned Sendai virus vector can be used as the starting Sendai virus vector for insertion of the MYC gene or Glis1 gene.

When inserting the MYC gene or Glis1 gene into a Sendai virus genome, a desirable site can be selected for the position of gene insertion in the vector. For example, the MYC gene or Glis1 gene is preferably positioned toward the rear of the minus-strand RNA genome (5' side), for example, more towards the 5' end than to the center of the minus-strand RNA virus genome (the position is further on the 5' end than that of the gene in the middle). That is, among the multiple protein-coding sequences positioned on the genome, it is preferably positioned at a site closer to the 5' end than the 3' end (see the Examples). The MYC gene or Glis1 gene can be positioned, for example, at the very end of the 5' side (i.e., first position from the 5' end), or at the second or third position from the 5' end. The MYC gene or Glis1 gene may be positioned at the second position from the 5' end of the genome, specifically, between the HN gene and the L gene (between HN-L) when the L gene is at the very end of the 5' side of the genome with the HN gene next to it. In particular, the MYC gene or Glis1 gene is preferably inserted immediately upstream (3' side, for example, between the HN gene and the L gene), or immediately downstream (5' side, for example, between the L gene and the 5' trailer sequence) of the L gene in the Sendai virus genome. The Sendai virus vector may be, for example, an F gene-deleted Sendai virus vector in which the M protein has G69E, T116A, and A183S mutations; the HN protein has A262T, G264R, and K461G mutations; the P protein has L511F mutation; and the L protein has N1197S and K1795E mutations (for example, the Z strain); and vectors produced by further introducing a TS 7, TS 12, TS 13, TS 14, or TS 15 mutation into this vector are more preferable. Examples include SeV(HNL)c-rMYC/TSΔF, SeV(L)c-rMYC/TSΔF, SeV(HNL)c-rMYC/TS15ΔF (WO 2010/008054; Fusaki et al., Proc Jpn Acad Ser B Phys Biol Sci. Vol. 85, p 348-362 (2009)), and preferably SeV(HNL)c-rMYC/TS15ΔF in particular, but are not limited thereto.

MYC genes including not only wild type c-MYC but also the T58A mutant, N-MYC, and L-MYC can induce pluripotent stem cells (WO 2007/69666; Blelloch R. et al., Cell Stem Cell, 1: 245-247, 2007). As such, since the family genes can be selected in various ways and used, reprogramming can be induced by appropriately selecting the MYC family genes. Furthermore, a continuous A or T nucleotide sequence of the MYC gene can be substituted by appropriately introducing silent mutations such that the encoded amino acid sequence is not changed.

For example, the amount of wild-type c-MYC expressed by an RNA virus vector such as a Sendai virus vector was found to be small. However, by introducing one or more, preferably two or more, three or more, or four or more mutations selected from a378g, t1122c, t1125c, a1191g, and a1194g, or all five of these mutations into the wild-type c-MYC, the gene can be highly expressed in a stable manner from a vector. In the present invention, for example, the modified c-MYC gene shown in SEQ ID NO: 45 of WO 2010/008054 can be used suitably.

When appropriate, genes for cellular reprogramming and such can be loaded additionally into the above-mentioned Sendai virus vector carrying the KLF, OCT, and SOX genes and/or the Sendai virus vector carrying the MYC gene. Furthermore, other vectors loaded with genes for cellular reprogramming and such may also be combined with the above-mentioned Sendai virus vectors. The genes to be loaded may be desired genes involved in the induction and such of various stem cells such as pluripotent stem cells from differentiated cells. For example, such genes that increase the efficiency of reprogramming can be loaded.

The present invention provides uses of the Sendai virus vectors of the present invention for introducing genes in cellular reprogramming, and uses of these vectors for expressing reprogramming factors in cells to induce reprogramming of those cells. Furthermore, the present invention provides agents containing the Sendai virus vectors of the present invention for introducing genes in cellular reprogramming (transfer agents, gene transfer agents) and agents containing these vectors for expressing reprogramming factors in cells. Furthermore, the present invention relates to agents containing the Sendai virus vectors of the present invention for expressing reprogramming factors in cells to induce reprogramming of the cells. Furthermore, when carrying out nuclear reprogramming of cells, the vectors of the present invention are also useful for expressing desired genes in these cells. Sendai virus vectors of the present invention can be utilized for cellular reprogramming according to the present invention. The induction of reprogramming may be specifically an induction of pluripotent stem cells. The present invention can be used for medical uses and for non-medical uses, and is useful in medical and non-medical embodiments. For example, the present invention can be used for therapeutic, surgical, and/or diagnostic, or non-therapeutic, non-surgical, and/or non-diagnostic purposes.

In the present invention, a nuclear reprogramming factor refers to a gene used, by itself or together with a number of factors, for inducing a differentiated state of a certain cell to change to a more undifferentiated state, or a product thereof, and includes for example, a gene used for inducing dedifferentiation of differentiated cells, or a product thereof. The nuclear reprogramming factors in the present invention include factors essential for nuclear reprogramming and accessorial factors (auxiliary factors) which increase the efficiency of nuclear reprogramming. In the present invention, desired genes to be used for nuclear reprogramming can be loaded into a vector. For example, genes to be used for the production of pluripotent stem cells can further be loaded. Specifically, as the nuclear reprogramming factors for induction of pluripotent stem cells, for example, genes that are expressed in ES cells or early embryo but are not expressed or whose expression is decreased in many differentiated somatic cells (ES cell-specific genes and such) can be used. Such genes are preferably genes that encode transcription factors, nucleoproteins, or such. Methods for identifying nuclear reprogramming factors are already known (WO 2005/80598), and in fact, genes identified using this method have been shown to be useful in reprogramming into pluripotent stem cells (WO 2007/69666).

Examples of such genes include DPPA5 (developmental pluripotency associated 5, ES cell specific gene 1 (ESG1); accession numbers NM_001025290, NM_025274, XM_236761), F-box protein 15 (Fbx15, NM_152676, NM_015798), Nanog (NM_024865, AB093574), ECAT1 (ES cell associated transcript 1; AB211062, AB211060), ERAS (ES cell expressed Ras; NM_181532, NM_181548), DNMT3L (DNA (cytosine-5-)-methyltransferase 3-like; NM_013369, NM_019448), ECAT8 (AB211063, AB211061), GDF3 (growth differentiation factor 3; NM_020634, NM_008108), SOX15 (SRY (sex determining region Y)-box 15; NM_006942, NM_009235), DPPA4 (developmental pluripotency associated 4; NM_018189, NM_028610), DPPA2 (NM_138815, NM_028615), FTHL17 (ferritin, heavy polypeptide-like 17; NM_031894, NM_031261), SALL4 (sal-like 4; NM_020436, NM_175303), OCT3/4 (also called POU5F1; NM_002701, NM_203289, NM_013633, NM_001009178), SOX2 (NM_003106, NM_011443, XM_574919), Rex-1 (ZFP42

(zinc finger protein 42 homolog); NM_174900, NM_009556), Utf1 (undifferentiated embryonic cell transcription factor 1; NM_003577, NM_009482), TCL1A (T-cell leukemia/lymphoma 1A; NM_021966, NM_009337), DPPA3 (also called Stella, NM_199286, NM_139218, XM_216263), KLF4 (Kruppel-like factor 4; NM_004235, NM_010637), cateninβ1 (cadherin-associated protein beta 1; NM_001904, NM_007614; including the S33Y mutant), c-MYC (NM_002467, NM_010849; including the T58A mutant), STAT3 (signal transducer and activator of transcription 3; NM_139276, NM_213659), GRB2 (growth factor receptor-bound protein 2; NM_002086, NM_008163), Glis1 gene (Maekawa et al., Nature, 474: 225-229, 2011; NM_147193, NM_147221), and other genes which are members of the families to which these genes belong. These genes induce pluripotent stem cells upon introduction into cells (WO 2007/69666). Therefore, from among the above-mentioned genes, a gene that is not yet loaded into the vector can be loaded additionally into a Sendai virus vector of the present invention which contains the KLF gene, OCT gene, and SOX gene in this order, or the OCT gene, SOX gene, and KLF gene in this order. Alternatively, other vectors equipped with these genes can be used in combination with the above-mentioned Sendai virus vector of the present invention which contains the KLF gene, OCT gene, and SOX gene in this order, or the OCT gene, SOX gene, and KLF gene in this order. These genes may be incorporated individually into separate vectors, or multiple genes can be incorporated into a single vector together. Furthermore, the individual genes can be incorporated into a single type of vector, or different types of vectors (including chromosome-integrating viral vector and/or non-viral vector) can be used in combination with the above-mentioned Sendai virus vector of the present invention which contains the KLF gene, OCT gene, and SOX gene in this order, or the OCT gene, SOX gene, and KLF gene in this order. In addition, individual virus vectors are packaged separately, and can be used by combining them at the time of use. Alternatively, multiple virus vectors carrying different genes can be combined in advance as a kit, or they may be mixed to produce a composition. Furthermore, one or more non-integrating virus vectors containing any combination (or all) of these genes, and kits or compositions further containing these vectors can be used favorably for cellular reprogramming, particularly in the production of pluripotent stem cells. In the case of compositions, the vectors may be appropriately combined with a pharmaceutically acceptable carrier and/or a medium, and for example, sterilized water, pH buffers, physiological saline solutions, culture solutions, and such may be mixed in. In these systems, some or most of the nuclear reprogramming genes can be substituted with their expression products that are proteins. More specifically, the compositions and kits of the present invention may include other vectors (chromosome-integrating virus vectors and/or non-viral vectors) that express reprogramming factors and/or compounds, proteins, or such that induce reprogramming as long as they include the above-mentioned Sendai virus vector containing at least the KLF gene, OCT gene, and SOX gene in this order, or the OCT gene, SOX gene, and KLF gene in this order. All of the factors necessary for reprogramming may be expressed from Sendai virus vectors, or some of them may be expressed from Sendai virus vectors, and the remaining factors may be provided from other vectors and/or compounds (for example, proteins or low-molecular-weight compounds). Furthermore, the methods of the present invention for producing reprogrammed cells are not limited to methods that carry out all gene deliveries using Sendai virus vectors. More specifically, the methods of the present invention only need to use the above-mentioned Sendai virus vector containing at least the KLF gene, OCT gene, and SOX gene in this order, or the OCT gene, SOX gene, and KLF gene in this order, and include combined use of other vectors (chromosome-integrating virus vectors and/or non-virus vectors) expressing reprogramming factors and/or compounds and such that induce reprogramming. Preferably, they are used in combination with the above-mentioned Sendai virus vector containing the MYC gene or Glis1 gene.

Furthermore, when using a Sendai virus vector containing the OCT gene, SOX gene, and KLF gene in this order, it is useful to combine with another Sendai virus vector containing the KLF gene.

The present invention relates to compositions for use in cellular reprogramming, which comprise the above-mentioned Sendai virus vectors containing the KLF gene, OCT gene, and SOX gene in this order, or the OCT gene, SOX gene, and KLF gene in this order as an expression vector. Furthermore, the present invention relates to use of the Sendai virus vectors for use in reprogramming of differentiated cells. For example, the present invention provides use of the Sendai virus vectors for introducing reprogramming factor genes (KLF, OCT, and SOX) into cells in need thereof in cellular reprogramming. Furthermore, the present invention relates to methods for introducing these genes in cellular reprogramming, which use the virus vectors to introduce the genes into cells in need thereof. The present invention also relates to compositions to be used for introducing the genes in cellular reprogramming and agents to be used for introducing the genes in cellular reprogramming (transfer agents to be used in introducing the genes in cellular reprogramming and agents for introducing the genes in cellular reprogramming), which comprise the above-mentioned virus vectors. Furthermore, the present invention relates to use of the virus vectors in the production of pharmaceutical agents for introducing the genes into cells in need thereof in cellular reprogramming. The present invention also provides agents which comprise the virus vectors for introducing the genes (gene expression agents or expression vectors) for use in cellular reprogramming. In addition, the present invention provides agents which comprise the virus vectors for introducing the reprogramming genes (gene expression agents or expression vectors). The present invention also provides agents which comprise the virus vectors for expressing nuclear reprogramming factors, the KLF gene, OCT gene, and SOX gene, or in the order of the OCT gene, SOX gene, and KLF gene (i.e., nuclear reprogramming gene-transfer agents, and nuclear reprogramming gene-expression vectors). Furthermore, the present invention provides pluripotent stem cell-inducing agents and pluripotent stem cell-inducing auxiliary agents, which contain the virus vectors encoding the nuclear reprogramming factors. The present invention provides use of the virus vectors for the reprogramming of differentiated cells. The present invention also provides use of the virus vectors in the production of pharmaceutical agents, reagents, and/or pharmaceuticals for the reprogramming of differentiated cells. The present invention also relates to use of the virus vectors in the production of agents for introducing the nuclear reprogramming factors (the KLF gene, OCT gene, and SOX gene) into differentiated cells.

Herein, reprogramming may be, for example, induction of pluripotent stem cells from differentiated cells. Vectors are used by incorporating genes encoding factors for reprogramming (the KLF gene, OCT gene, and SOX gene). Examples of genes encoding reprogramming factors include genes encoding any one of the above-mentioned factors or factors exemplified below.

The factors that are introduced (the KLF gene, OCT gene, SOX gene, and the like) may be selected appropriately according to the origin of the cells to be reprogrammed, and they may be derived from humans or other mammals such as mice, rats, rabbits, pigs, or primates such as monkeys. Furthermore, the genetic and protein sequences do not necessarily have to be wild-type sequences, and as long as they can induce reprogramming, they may have mutations. Examples of producing pluripotent stem cells using mutant genes are known (WO 2007/69666). For example, a gene encoding an amino acid sequence with one or a small number of (for example, a few, not more than three, not more than five, not more than ten, not more than 15, not more than 20, or not more than 25) amino acid additions, deletions, substitutions, and/or insertions, and which can induce reprogramming may be used in the present invention. Furthermore, as long as biological activity (ability to induce reprogramming) is maintained, for example, polypeptides with deletions or additions of one to several residues (for example, 2, 3, 4, 5, 6, 10, 15, or 20 residues) of amino acids of the N terminus and/or the C terminus, polypeptides with substitution of one to several residues (for example, 2, 3, 4, 5, 6, 10, 15, or 20 residues) of amino acids, and such may be used. Variants which may be used include for example, fragments, analogs, and derivatives of natural proteins, and fusion proteins of natural proteins with other polypeptides (for example, those with addition of heterologous signal peptides or antibody fragments). Specifically, polypeptides comprising a sequence with one or more amino acid substitutions, deletions, and/or additions in the wild-type amino acid sequence, and having a biological activity (for example, activity to induce reprogramming) equivalent to that of wild-type proteins are included. When using a fragment of a wild-type protein, normally, the fragment contains a continuous region of 70% or more, preferably 80% or more, 85% or more, more preferably 90% or more, 95% or more, or 98% or more of the wild-type polypeptide (a mature form in the case of a secretory protein).

Variants of amino acid sequences can be prepared, for example, by introducing mutations to the DNAs encoding the natural polypeptide (Walker and Gaastra, eds. Techniques in Molecular Biology (MacMillan Publishing Company, New York, 1983); Kunkel, Proc. Natl. Acad. Sci. USA 82: 488-492, 1985; Kunkel et al., Methods Enzymol. 154: 367-382, 1987; Sambrook et al., Molecular Cloning: A Laboratory Manual (Cold Spring Harbor Laboratory Press, Plainview, N.Y.), 1989; U.S. Pat. No. 4,873,192). An example of guidance for substituting amino acids without affecting biological activity includes the report by Dayhoff et al. (Dayhoff et al., in Atlas of Protein Sequence and Structure (Natl. Biomed. Res. Found., Washington, D.C.), 1978).

The number of amino acids that are modified is not particularly limited, but for example, it is 30% or less, preferably 25% or less, more preferably 20% or less, more preferably 15% or less, more preferably 10% or less, 5% or less, or 3% or less of all amino acids of the natural mature polypeptide, and is, for example, 15 amino acids or less, preferably ten amino acids or less, more preferably eight amino acids or less, more preferably five amino acids or less, or more preferably three amino acids or less. When substituting amino acids, activities of the protein can be expected to be maintained by substitution to an amino acid with similar side chain properties. Such substitutions are called conservative substitutions in the present invention. Examples of conservative substitutions include substitution and such among amino acids within each of the groups such as basic amino acids (such as lysine, arginine, and histidine), acidic amino acids (for example, aspartic acid and glutamic acid), uncharged polar amino acids (for example, glycine, asparagine, glutamine, serine, threonine, tyrosine, and cysteine), nonpolar amino acids (for example, alanine, valine, leucine, isoleucine, proline, phenylalanine, methionine, and tryptophan), β-branched amino acids (for example, threonine, valine, isoleucine), and aromatic amino acids (for example, tyrosine, phenylalanine, tryptophan, and histidine). Furthermore, examples include substitution among amino acids whose relationship in the BLOSUM62 substitution matrix (S. Henikoff and J. G. Henikoff, Proc. Acad. Natl. Sci. USA 89: 10915-10919, 1992) is positive.

The modified proteins exhibit a high homology to the amino acid sequence of the wild-type protein. High homology refers to amino acid sequences having, for example, 70% or higher, 75% or higher, 80% or higher, 85% or higher, 90% or higher, 93% or higher, 95% or higher, or 96% or higher identity. Amino acid sequence identity can be determined using, for example, the BLASTP program (Altschul, S. F. et al., J. Mol. Biol. 215: 403-410, 1990). A search can be carried out using default parameters in the Web page of BLAST at NCBI (National Center for Biotechnology Information) (Altschul S. F. et al., Nature Genet. 3: 266-272, 1993; Madden, T. L. et al., Meth. Enzymol. 266: 131-141, 1996; Altschul S. F. et al., Nucleic Acids Res. 25: 3389-3402, 1997; Zhang J. & Madden T. L., Genome Res. 7: 649-656, 1997). Alignment of two sequences can be produced, for example, by the Blast 2 sequences program which compares two sequences (Tatiana A et al., FEMS Microbiol Lett. 174: 247-250, 1999) and the identity of the sequences can be determined. Gaps and mismatches are treated similarly, and for example, a value of identity with respect to the entire amino acid sequence of a naturally-derived cytokine (mature form after secretion) is calculated. Specifically, the proportion of the number of matching amino acids in the total number of amino acids of the wild-type protein (mature form in the case of a secreted protein) is calculated.

Furthermore, genes can be introduced with a silent mutation such that the encoded amino acid sequence is not changed. Particularly, in AT rich genes, by substituting five or more consecutive A or T nucleotides with G or C such that the encoded amino acid sequence is not changed, high expression of genes can be stably obtained.

Examples of modified proteins or proteins used for reprogramming are proteins encoded by nucleic acids that hybridize under stringent conditions with a part or all of the coding region of a gene encoding the wild-type protein and having an activity (activity to induce reprogramming) equivalent to that of the wild-type protein. In hybridization, for example, a probe is prepared either from a nucleic acid comprising a sequence of the coding region of the wild-type protein gene or a complementary sequence thereof or from a nucleic acid which is the object of hybridization, and identification can be carried out by detecting whether or not the probe hybridizes to the other nucleic acid. Stringent hybridization conditions are, for example, conditions of performing hybridization in a solution containing 5×SSC, 7% (W/V) SDS, 100 µg/mL denatured salmon sperm DNA, 5×Denhardt's solution (1×Denhardt's solution includes 0.2% polyvinyl pyrrolidone, 0.2% bovine serum albumin, and 0.2% Ficoll) at 60° C., preferably 65° C., and more preferably 68° C., and then washing by shaking for two hours in 2×SSC, preferably in 1×SSC, more preferably in 0.5×SSC, and more preferably in 0.1×SSC at the same temperature as hybridization.

Examples of genes particularly preferable for inducing cellular reprogramming typically include F-box protein 15 (Fbx15, NM_152676, NM_015798), Nanog (NM_024865, AB093574), ERAS (ES cell expressed Ras; NM_181532, NM_181548), DPPA2 (NM_138815, NM_028615), OCT3/4 (also called POU5F1; NM_002701, NM_203289, NM_013633, NM_001009178), SOX2 (NM_003106, NM_011443, XM_574919), TCL1A (T-cell leukemia/lymphoma 1A; NM_021966, NM_009337), KLF4 (Kruppel-like factor 4; NM_004235, NM_010637), catenin β1 (cadherin-associated protein beta 1; NM_001904, NM_007614; including the S33Y mutant), c-MYC (NM_002467, NM_010849; including the T58A mutant), and Glis1 gene (Maekawa et al., Nature, 474: 225-229, 2011; NM_147193, NM_147221), as well as other genes which are members of the families to which these genes belong. When these genes are introduced, the proportion of colonies showing the morphology of pluripotent stem cells has been reported to be higher than when the four types of genes (OCT3/4, SOX2, KLF4, and c-MYC) are introduced (WO 2007/69666). Therefore, Sendai virus vectors further carrying any one of the above-mentioned genes or a combination thereof in addition to the KLF gene, OCT gene, and SOX gene, or combinations of a Sendai virus vector of the present invention carrying the KLF gene, OCT gene, and SOX gene with a Sendai virus vector or vectors carrying any one of the above-mentioned genes or a combination thereof are useful for use in the induction of cellular reprogramming in the present invention, and in particular, they can be used favorably for the induction of pluripotent stem cells. Individual virus vectors can be used by combining them at the time of use. Furthermore, they can be combined in advance as a kit, or they may be mixed to form a composition. Furthermore, one or more Sendai virus vectors containing any combination of any (or all) of the above-mentioned genes in addition to the KLF gene, OCT gene, and SOX gene, and kits or compositions containing these vectors are also included in the present invention.

It is preferable to combine the vectors of the present invention for expressing the KLF gene, OCT gene, and SOX gene, particularly with vectors for expressing the MYC gene and/or the Glis1 gene (Takahashi, K. and Yamanaka S., Cell 126: 663-676, 2006; Lowry W E et al., Proc Natl Acad Sci USA, 105(8): 2883-8, 2008; Masaki, H. et al., Stem Cell Res. 1: 105-115, 2008; Maekawa et al., Nature, 474: 225-229, 2011; WO 2007/69666). Herein, the SOX protein, the KLF protein, the MYC protein, and the OCT protein, and their genes refer to proteins and genes which are members belonging to the SOX family, the KLF family, the MYC family, and the OCT family, respectively. There are reports that by making adjustments so that one or more members from each of these four families are expressed, pluripotent stem cells can be induced from various differentiated cells. For example, regarding the SOX family genes, the use of any of the SOX1, SOX2, SOX3, SOX15, and SOX17 genes has been reported to be able to induce pluripotent stem cells (WO 2007/69666). Regarding the KLF family as well, pluripotent stem cells could be induced with KLF4 or KLF2 (WO 2007/69666). Regarding the MYC family as well, not only the wild-type c-MYC but the T58A mutant, N-MYC, and L-MYC could also induce pluripotent stem cells (WO 2007/69666; Blelloch R. et al., Cell Stem Cell, 1: 245-247, 2007). This way, since genes of the families can be selected in various ways and then used, reprogramming can be induced by appropriately selecting genes from the four families mentioned above.

Specifically, the KLF family includes KLF1 (NM_006563, NM_010635), KLF2 (NM_016270, NM_008452), KLF4 (NM_004235, NM_010637), and KLF5 (NM_001730, NM_009769); the MYC family includes c-MYC (NM_002467, NM_010849, including the T58A mutant), N-MYC (NM_005378, NM_008709), and L-MYC (NM_005376, NM_005806); the OCT family includes OCT1A (NM_002697, NM_198934), OCT3/4 (NM_002701, NM_203289, NM_013633, NM_001009178), and OCT6 (NM_002699, NM_011141); and the SOX family includes SOX1 (NM_005986, NM_009233), SOX2 (NM_003106, NM_011443, XM_574919), SOX3 (NM_005634, NM_009237), SOX7 (NM_031439, NM_011446), SOX15 (NM_006942, NM_009235), SOX17 (NM_022454, NM_011441), and SOX18 (NM_018419, NM_009236). Sendai virus vectors carrying any one of these genes according to the order of the present invention are useful for use in inducing dedifferentiation of cells in the present invention, and can be used favorably for induction of pluripotent stem cells in particular. MYC family genes are not essential for induction of pluripotent stem cells, and pluripotent stem cells can be induced using only the genes of the three families excluding the MYC family genes (Nakagawa M. et al., Nat. Biotechnol. 26(1): 101-6, 2008; Wering M. et al., Cell Stem Cell 2(1): 10-2, 2008). When the MYC gene is not expressed, for example, p53 siRNA and UTF1 can be used to significantly increase the induction efficiency of pluripotent stem cells (Y. Zhao et al., Cell Stem Cell, 3 (5): 475-479, 2008; N. Maherali, and K. Hochedlinger, Cell Stem Cell, 3 (6): 595-605, 2008). Furthermore, induction of pluripotent stem cells has been also reported to be possible using only the genes of the three families excluding the KLF family genes (Park I H et al., Nature, 451(7175): 141-6, 2008). In addition, by combined use of the G9a histone methyltransferase inhibitor (BIX-01294; Kubicek, S. et al., Mol. Cell. 25: 473-481, 2007), induction of pluripotent stem cells has been reported to be possible from fetal NPC using only three genes, i.e., the KLF gene, SOX gene, and MYC gene (Shi Y et al., Cell Stem Cell, 2(6): 525-8, 2008). Virus vectors that encode the respective genes can be separately prepared individually. They can be used by combining them at the time of use. Any combination or all of them may be combined to form a kit or mixed to form a composition. In addition to the Sendai virus vector of the present invention carrying the KLF gene, OCT gene, and SOX gene, the present invention also relates to one or more chromosomally non-integrating virus vectors comprising any combination (or all) of genes other than these three genes and compounds, and a kit or a composition for reprogramming which comprise these vectors. Furthermore, a portion of the recombinant vectors included in this kit can be substituted with proteins, synthetic compounds, or such having corresponding functions.

Other genes can be further combined to the above-described combination of genes to increase the efficiency of induction of reprogramming. Examples of such genes include TERT (NM_198253, NM_009354) and/or SV40 large T antigen (NC_001669.1, Fiers, W. (5 Nov. 1978) Nature 273 (5658): 113-120) (Park I H. et al., Nature, 451 (7175): 141-6, 2008). One or more genes selected from the group consisting of HPV16 E6, HPV16 E7, and Bmil (NM_005180, NM_007552) may also be further combined. Furthermore, one or any combination of genes selected from the group consisting of Fbx15 (Mol Cell Biol. 23(8): 2699-708, 2003), Nanog (Cell 113: 631-642, 2003), ERas (Nature 423: 541-545, 2003), DPPA2 (Development 130: 1673-1680, 2003), TCL1A (Development 130: 1673-1680, 2003), and β-Catenin (Nat Med 10(1): 55-63, 2004) may be expressed. In addition, one or more genes selected from the group consisting of ECAT1 (AB211062, AB211060), DPPA5 (NM_001025290, NM_025274, XM_236761), DNMT3L (NM_013369, NM_019448), ECAT8 (AB211063, AB211061), GDF3 (NM_020634, NM_008108), SOX15 (NM_006942, NM_009235), DPPA4 (NM_018189, NM_028610), FTHL17 (NM_031894, NM_031261), SALL4 (NM_020436, NM_175303), Rex-1 (NM_174900, NM_009556), Utf1 (NM_003577, NM_009482), DPPA3 (NM_199286, NM_139218, XM_216263), STAT3 (NM_139276, NM_213659), and GRB2 (NM_002086, NM_008163) may be combined. Combinations comprising each NANOG gene (NM_024865, AB093574) and LIN28 gene (NM_024674) in addition to the KLF gene, the OCT gene, and the SOX gene are useful for inducing pluripotent stem cells (Yu J. et al., Science, 318(5858): 1917-20, 2007). In addition, further combining with MYC gene is preferred (Liao J et al., Cell Res. 18(5): 600-3, 2008). By additionally expressing these genes, induction of pluripotent stem cells may be promoted (WO 2007/69666). When mature B cells are the subjects, for example, the myelocytic transcription factor C/EBPα (CCAAT/enhancer-binding-protein a) (NM_004364) can be ectopically expressed, or expression of the B cell transcription factor Pax5 (paired box 5; NM_016734) can be suppressed to promote reprogramming (Hanna J, Cell. 133(2): 250-64, 2008). These factors can also be expressed using the Sendai virus vectors of the present invention. Furthermore, a portion of the recombinant vectors included in this kit can be substituted with proteins, synthetic compounds, and such which have corresponding functions.

Furthermore, besides expressing the above-mentioned factors, for example, by combining the addition of compounds, the efficiency of reprogramming can be increased. For example, bFGF (basic fibroblast growth factor) and/or SCF (stem cell factor) can promote the induction of pluripotent stem cells, and moreover can replace the function of c-MYC in the induction of pluripotent stem cells (WO 2007/69666). Furthermore, MAP kinase inhibitor (PD98056) is also useful for establishing pluripotent stem cells that are closer to ES cells, and such (WO 2007/69666). Furthermore, DNA methylase (Dnmt) inhibitors and/or histone deacetylase (HDAC) inhibitors are reported to improve the efficiency of induction of pluripotent stem cells (Huangfu D et al., Nat. Biotechnol. (Published online: 22 Jun. 2008, doi:10.1038/nbt1418); Nat. Biotechnol. 26: 795-797 (2008)). For example, combined use of HDAC(VPA) enables induction of pluripotent stem cells by introduction of only two genes, OCT4 and SOX2 (Huangfu, D. et al., Nat. Biotechnol. 2008 26(11): 1269-75). Vectors of the present invention are useful as agents used in combination with administration of these compounds. As Dnmt inhibitors, for example, 5-azacytidine and such are useful, and as HDAC inhibitors, for example, suberoylanilide hydroxamic acid (SAHA), trichostatin A (TSA), valproic acid (VPA) and such are useful. Furthermore, when using 5-azacytidine, combined use of glucocorticoid (dexamethasone) can increase the efficiency.

To reprogram cells, for example, (1) a vector of the present invention for expressing the KLF gene, OCT gene, and SOX gene, (2) a combination of the vector of (1) with a Sendai virus vector for expressing the MYC gene or Glis1 gene, (3) a combination produced by further adding to (2) a Sendai virus vector for expressing the NANOG gene, and a Sendai virus vector for expressing LIN28, (4) a combination produced by further adding to the combination of (2), one or two types of Sendai virus vectors individually expressing each of the KLF gene, OCT gene, and SOX gene (for example, a combination of an SeV vector carrying the OCT3/4-SOX2-KLF4 gene, a vector carrying the MYC gene, and a vector carrying the KLF gene, and such), or (5) a combination of the vector of (1) with vectors carrying other desired reprogramming factors mentioned above, and/or desired reprogramming-inducing compounds, and such may be introduced into cells. The vector of (1) includes the Sendai virus vectors of the present invention, which contains the KLF gene, OCT gene, and SOX gene in this order, or the OCT gene, SOX gene, and KLF gene in this order. When a number of vectors and/or compounds are combined and introduced, the introduction is preferably carried out simultaneously, and specifically, it is preferable to complete the addition of all vectors encoding the reprogramming factors and/or compounds within 48 hours or less, preferably 36 hours or less, more preferably 24 hours or less, 18 hours or less, twelve hours or less, ten hours or less, eight hours or less, six hours or less, three hours or less, two hours or less, or one hour or less of the addition of the first vector, compound, or such. The dose of the vectors can be prepared appropriately and the MOI is, for example, 0.1 or more, preferably 0.3 or more, 0.5 or more, 1 or more, 2 or more, or 3 or more, and 100 or less, preferably 90 or less, 80 or less, 70 or less, 60 or less, 50 or less, 40 or less, 30 or less, 20 or less, 10 or less, or 5 or less. Preferably, infection is carried out, for example, at MOI of 0.3 to 100, more preferably at MOI of 0.5 to 50, more preferably at MOI of 1 to 40, more preferably at MOI of 1 to 30, more preferably at MOI of 2 to 30, and for example at MOI of 3 to 30. The induced pluripotent stem cells form flat colonies very similar to those of ES cells, and express alkaline phosphatase. Furthermore, the induced pluripotent stem cells may express the undifferentiated-cell markers Nanog, OCT4, and/or SOX2, and the like. The induced pluripotent stem cells preferably express TERT and/or show telomerase activity. The present invention also relates to methods for producing cells that express alkaline phosphatase and preferably further express Nanog and/or TERT which are undifferentiated-cell markers, and to a use of Sendai virus vectors in the production of these cells and in the production of pharmaceutical agents for inducing these cells.

According to the present invention, colonies of pluripotent stem cells can be induced from desired cells including adult skin cells and neonatal foreskin cells, for example, for at least certain cells at an incidence rate of $0.03 \times 10^{-5}$ or more, $0.1 \times 10^{-5}$ or more, $0.3 \times 10^{-5}$ or more, $0.5 \times 10^{-5}$ or more, $0.8 \times 10^{-5}$ or more, or $1 \times 10^{-5}$ or more (for example, $1 \times 10^{-5}$ to $1 \times 10^{-3}$), and preferably at an incidence rate of $1.5 \times 10^{-5}$ or more, $1.7 \times 10^{-5}$ or more, $2.0 \times 10^{-5}$ or more, $2.5 \times 10^{-5}$ or more, $3 \times 10^{-5}$ or more, $4 \times 10^{-5}$ or more, $5 \times 10^{-5}$ or more, $8 \times 10^{-5}$ or more, $1 \times 10^{-4}$ or more, $2 \times 10^{-4}$ or more, $3 \times 10^{-4}$ or more, $5 \times 10^{-4}$ or more, $8 \times 10^{-4}$ or more, $1 \times 10^{-3}$ or more, $1.5 \times 10^{-3}$ or more, $2 \times 10^{-3}$ or more, $5 \times 10^{-3}$, $1 \times 10^{-2}$ or more, $1.5 \times 10^{-2}$ or more, $2 \times 10^{-2}$ or more, $2.5 \times 10^{-2}$ or more, $3 \times 10^{-2}$ or more, $4 \times 10^{-2}$ or more, or $5 \times 10^{-2}$ or more. Furthermore, for at least certain cells, the efficiency of appearance of pluripotent stem cell colonies by the vectors of the present invention is, for example, 1.5 times or more, preferably twice or more, 2.5 times or more, three times or more, 3.5 times or more, four times or more, 4.5 times or more, or five times or more compared to the control, in which the KLF gene, OCT gene, and SOX gene are individually loaded into separate Sendai virus vectors. Furthermore, for at least certain cells, the efficiency of appearance of pluripotent stem cell colonies by the vectors of the present invention containing the KLF gene, OCT gene, and SOX gene in this order is, for example, 1.5 times or more, preferably twice or more, 2.5 times or more, three times or more, 3.5 times or more, four times or more, 4.5 times or more, or five times or more compared to the control in which the KLF gene, OCT gene, and SOX gene are loaded into a single Sendai virus vector in a different order, for example, in the order of the OCT gene, SOX gene, and KLF gene. When vectors of the present invention with insertion of the OCT gene, SOX gene, and KLF gene in this order are used, a characteristic advantage is the fast growth of iPS cells (fast growth of the colonies).

Differentiated cells which become the object of induction of reprogramming are not particularly limited, and desired somatic cells and such may be used. Production of pluripotent stem cells from somatic cells has been shown to be possible not only from cells derived from fetal mice but also from differentiated cells collected from the tail portion of adult mice, and from liver cells, and gastric mucosal cells, and this suggests that the production is not dependent on the cell type or the state of differentiation (WO 2007/069666; Aoi T. et al., Science [Published Online Feb. 14, 2008]; Science. 2008; 321(5889): 699-702). Induction of pluripotent stem cells has been confirmed to be possible in humans as well, from various cells such as adult facial skin-derived fibroblasts, adult synoviocytes, neonatal foreskin-derived fibroblasts, adult mesenchymal stem cells, skin cells from the palm of an adult, and embryonic cells (Takahashi K et al. (2007) Cell 131: 861-872; Park I H et al., Nature, 451(7175): 141-6, 2008). Furthermore, induction of pluripotent stem cells has been reported similarly from terminally differentiated cells such as pancreatic p cells and B lymphocytes as well (Stadtfeld M et al., Curr Biol. 2008 May 21. [PubMed, PMID: 18501604]; Curr Biol. 2008, 18(12): 890-4; Hanna J. et al., Cell. 133(2): 250-64, 2008). These findings suggest that induction of pluripotent stem cells do not depend on the cells serving as the origin. Methods of the present invention can be applied in the induction of pluripotent stem cells from these desired somatic cells. Specifically, differentiated cells which are the object of reprogramming include fibroblasts, synoviocytes, mucosal cells of the oral cavity, stomach, or such, liver cells, bone marrow cells, tooth germ cells, blood cells (for example, lymphocytes and leukocytes), and other desired cells. Furthermore, cells may be derived, for example, from cells of embryos, fetuses, newborns, children, adults, or the aged. The origin of the animals is not particularly limited, and includes mammals such as humans and non-human primates (monkeys and such), rodents such as mice and rats, and non-rodents such as bovine, pigs, and goats.

From the colonies of cells which have completed reprogramming, cells from which the vectors have been removed can be selected appropriately. For example, cells from which the vectors have been naturally removed may be selected. To this end, for example, negative selection can be carried out using antibodies specific to the virus vectors (for example, anti-HN antibodies). Furthermore, when using temperature-sensitive vectors, the vectors can be removed easily by culturing at high temperatures (for example, 37.5° C. to 39° C., preferably 38° C. to 39° C., or 38.5° C. to 39° C.). When SeV(PM)/TSΔF, or vectors with further introduction of mutations such as TS 7, TS 12, TS 13, TS 14, or TS 15 into SeV(PM)/TSΔF are used, passaging leads to natural loss of the vector. Examples of preferred vectors include SeV(PM) KOS/TS12ΔF, but are not limited thereto. Furthermore, in this case, the MYC gene can be introduced using SeV(HNL) c-rMYC/TS12ΔF, SeV(HNL)c-rMYC/TS13ΔF, SeV(HNL) c-rMYC/TS15ΔF, or such. Furthermore, by not loading the MYC gene into the Sendai virus vectors carrying the KLF gene, OCT gene, and SOX gene, reprogramming can be advantageously done without use of the carcinogenesis-related MYC gene. This is also advantageous because it is possible to freely select the fourth factor for use from c-MYC, L-MYC, Glis1, or such in addition to the KLF gene, OCT gene, and SOX gene.

Cells produced by the methods of the present invention are useful for causing differentiation into a variety of tissues and cells, and can be used in desired examinations, research, diagnosis, tests, treatments, and such. For example, induced stem cells are expected to be utilized in stem cell therapy. For example, reprogramming is induced by using somatic cells collected from patients, and then somatic stem cells and other somatic cells that are obtained by induction of differentiation can be transplanted into patients. Methods for inducing cellular differentiation are not particularly limited, and for example, differentiation can be induced by retinoic acid treatment, treatment with a variety of growth factors/cytokines, and treatment with hormones. Furthermore, the obtained cells can be used for detecting effects of the desired pharmaceutical agents and compounds, and this enables screening of pharmaceutical agents and compounds to be carried out.

EXAMPLES

Hereinbelow, the present invention is specifically described with reference to the Examples; however, it is not to be construed as being limited thereto. All documents and other references cited herein are incorporated as part of this description.

Example 1

Construction of pSeV(PM)/TSΔF

The methods for producing Sendai virus vectors carrying a foreign gene used in the present invention are shown below. Unless otherwise specified, foreign genes were introduced using these vectors in all of the Examples. In the present invention, "(PM)" refers to inserting a reprogramming gene between the P gene and the M gene, and "(HNL)" refers to inserting a reprogramming gene between the HN gene and the L gene. Furthermore, in the present invention, "TS" refers to having G69E, T116A, and A183S mutations in the M protein, A262T, G264R, and K461G mutations in the HN protein, L511F mutation in the P protein, and N1197S and K1795E mutations in the L protein; and "ΔF" shows that the F gene is deleted. Hereinbelow, "SeV(PM)/TSΔF" refers to an F gene-deleted Sendai virus vector having G69E, T116A, and A183S mutations in the M protein; A262T, G264R, and K461G mutations in the HN protein; L511F mutation in the P protein; and N1197S and K1795E mutations in the L protein (Z strain). This vector has an insertion site (NotI site) for gene introduction immediately downstream of the P gene (between the P gene and M gene). However, these are exemplary, and the present invention is not limited to these examples.

pSeV(PM)/TSΔF was constructed as follows. PCR was carried out (94° C. for three minutes, and 25 cycles of [98° C. for ten seconds, 55° C. for 15 seconds, and 72° C. for 12 minutes], followed by 72° C. for seven minutes) using Litmus SalINheIfrg PmutMtsHNts ΔF-GFP deTGFβ (International Publication No. WO 2010/008054) as template, together with PMNOTI-F (5'-GAAATTTCACCTAAGCGGCCGCAATG-GCAGATATCTATAG-3') (SEQ ID NO: 10) and PMNOTI-R (5'-CTATAGATATCTGCCATTGCGGCCGCT-TAGGTGAAATTTC-3') (SEQ ID NO: 11). The approximately 11-kb PCR product obtained was treated with DpnI, and then *Escherichia coli* DH5a (ToYoBo Code No. DNA-903) was transformed with 20 μL of this reaction solution. Six *E. coli* colonies were picked up and mini-prep was performed. A plasmid having the NotI sequence was selected by NotI digestion. Then, a clone that has the correct sequence was selected by sequencing. Thus, Litmus SalINheIfrg PmutMtsHNts(PM)-dF was obtained. Then, Litmus SalINheIfrg PmutMtsHNts(PM)-dF was digested with SalI and NheI, and the collected fragment (approximately 8 kbp) was ligated to a fragment (approximately 8 kbp) collected upon SalI/NheI digestion of the pSeV/ΔSalINheIfrg Lmut plasmid (International Publication No. WO 2003/025570) having two mutations in the L gene. Thus, pSeV (PM)/TSΔF was obtained. This vector has an insertion site (NotI site) for gene introduction between the P and M genes.

Example 2

Preparation of Plasmids for Production of SeV Vectors Carrying the KLF-OCT3/4-SOX2 Genes The KLF4 gene was amplified by PCR (95° C. for three minutes, and 30 cycles of [98° C. for ten seconds, 55° C. for 15 seconds, and 72° C. for 2 minutes], followed by 72° C. for seven minutes) using PrimeStar HS DNA Polymerase (Takara Bio, catalog No. R010A); pSeV18+KLF4/TSΔF (WO 2010/008054) as template; and primers NotI-KIF-4F (5'-ATTGCGGCCGCGACATGGCTGTCAGC-GACGCGCTG-3') (SEQ ID NO: 12) and KOS-KO-R (5'-TCCGAAGCCAGGTGTCCCGCCATGGCG-GCTGTTAGGTGGATGAACTTTCACCCTAAG TTTTTCTTACTACGGTTAAAAATGCCTC-3') (SEQ ID NO: 13). The PCR product was purified using the Qiaquick PCR Purification Kit (QIAGEN, catalog No. 28106), and eluted with 100 μl of an elution solution attached to the kit.

The OCT3/4 gene was amplified by PCR (95° C. for three minutes, and 30 cycles of [98° C. for ten seconds, 55° C. for 15 seconds, and 72° C. for 2 minutes], followed by 72° C. for seven minutes) using PrimeStar HS DNA Polymerase (Takara Bio, catalog No. R010A); pSeV18+OCT3/4/TSΔF (WO 2010/008054) as template; and primers KOS-KO-F (5'-GAGGCATTTTTAACCGTAGTAA-GAAAAACTTAGGGTGAAAGTTCATCCACCTAACA GCCGCCATGGCGGGACACCTGGCTTCGGA-3') (SEQ ID NO: 14) and KOS-OS-R (5'-CCGTCTCCATCATGTTG-TACATGGCGGCGTGTTAGGT-GAAATCTTTCACCCTAAGTTT TTCTTATTCTACGGT-CAGTTTGAATGCATGGG-3') (SEQ ID NO: 15). The PCR product was purified using the Qiaquick PCR Purification Kit (QIAGEN, catalog No. 28106) and eluted with 100 μl of an elution solution attached to the kit. The SOX2 gene was amplified by PCR (95° C. for three minutes, and 30 cycles of [98° C. for ten seconds, 55° C. for 15 seconds, and 72° C. for 2 minutes], followed by 72° C. for seven minutes) using PrimeStar HS DNA Polymerase (Takara Bio, catalog No. R010A); pSeV18+SOX2/TSΔF (WO 2010/008054) as template; and primers KOS-OS-F (5'-CCCATGCATTCAAACT-GACCGTAGAATAAGAAAAACTTAGGGT-GAAAGATTTCACC TAACACGCCGCCATGTACAACATGATGGAGACGG-3') (SEQ ID NO: 16) and Not I SOX-2R (5'-ATTGCGGC-CGCGATGAACTTTCAC-CCTAAGTTTTTCTTACTACGGTCACATGTGTGA GAGGGGCAGTGTGCCGTTAATGGCCGTG-3') (SEQ ID NO: 17). The PCR product was purified using the Qiaquick PCR Purification Kit (QIAGEN, catalog No. 28106) and eluted with 100 μl of an elution solution attached to the kit.

A second PCR was performed using these purified PCR products. PrimeStar HS DNA Polymerase (Takara Bio, catalog No. R010A) was used, and 1 μL each of the above-mentioned purified KLF4 gene PCR product, the OCT3/4 gene PCR product, and the SOX2 gene PCR product were added. NotI-KIF-4F (5'-ATTGCGGCCGCGACATGGCT-GTCAGCGACGCGCTG-3') (SEQ ID NO: 12) and Not I SOX-2R (5'-ATTGCGGCCGCGATGAACTTTCAC-CCTAAGTTTTTCTTACTACGGTCACATGTGTGAG AGGGGCAGTGTGCCGTTAATGGCCGTG-3') (SEQ ID NO: 17) were used as primers, and PCR was carried out (95° C. for three minutes, and 30 cycles of [98° C. for ten seconds, 55° C. for 15 seconds, and 72° C. for 2 minutes], followed by 72° C. for seven minutes) for amplification.

Furthermore, as another condition, the above-mentioned purified KLF4 gene PCR product, OCT3/4 gene PCR product, and SOX2 gene PCR product were diluted ten-fold with $H_2O$, and 1 μL each of the diluted solutions was added; and NotI-KIF-4F (5'-ATTGCGGCCGCGACATGGCTGT-CAGCGACGCGCTG-3') (SEQ ID NO: 12) and Not I SOX-2R (5'-ATTGCGGCCGCGATGAACTTTCAC-CCTAAGTTTTTCTTACTACGGTCACATGTGTGAG AGGGGCAGTGTGCCGTTAATGGCCGTG-3') (SEQ ID NO: 17) were used as primers. PCR was carried out (95° C. for three minutes, and 30 cycles of [98° C. for ten seconds, 55° C. for 15 seconds, and 72° C. for 2 minutes], followed by 72° C. for seven minutes) for amplification.

The PCR product was purified using the Qiaquick PCR Purification Kit (QIAGEN, catalog No. 28106), and eluted with 50 μL of an elution solution attached to the kit. This purified product was digested with NotI, and separated by 1% agarose gel electrophoresis. After electrophoresis, a band of about 3.6 kbp was excised, and purification was carried out using the Qiaquick Gel Extraction Kit (QIAGEN, catalog No. 28706). 100 μL of an elution solution attached to the kit was used for elution. The NotI fragment containing the KLF4 gene, OCT3/4 gene, and SOX2 gene was cloned into the NotI site of the pSeV(PM)/TSΔF vector, and a clone that has the correct sequence was selected by sequencing to obtain pSeV (PM)KOS/TSΔF.

Example 3

Production of SeV Vectors Carrying the Human KLF4-OCT3/4-SOX2 Genes

One day before transfection, $10^6$ 293T/17 cells were seeded into each well of a 6-well plate, and cultured in a $CO_2$ incubator (under 5% $CO_2$ condition) at 37° C. Using 15 μl of TransIT-LT1 (Mirus), the 293T/17 cells were transfected with a mixture of:
0.5 μg of pCAGGS-NP, 0.5 μg of pCAGGS-P4C (−), 2 μg of pCAGGS-L (TDK), 0.5 μg of pCAGGS-T7, 0.5 μg of pCAGGS-F5R (WO 2005/071085), and 5.0 μg of the above-described Sendai virus vector plasmid pSeV(PM)KOS/ TSΔF. The cells were cultured in a $CO_2$ incubator at 37° C. for two days. Then, $10^6$ cells of LLC-MK2/F/A which express the fusion protein (F protein) of Sendai virus (Li, H.-O. et al., J. Virology 74. 6564-6569 (2000); WO 00/70070) were overlaid onto the transfected 293T/17 cells in each well. Then, the cells were cultured in a $CO_2$ incubator at 37° C. for one day. On the following day, the cell culture medium was removed, and the cells were washed once with 1 ml of MEM supplemented with penicillin-streptomycin (hereinafter abbreviated as PS/MEM). 1 ml of PS/MEM containing 2.5 μg/ml trypsin (hereinafter abbreviated as Try/PS/MEM) was added to each well. The cells were cultured in a $CO_2$ incubator at 32° C. for two days. The cells were continuously cultured while exchanging the medium every three to four days, and in some cases, passaging with LLC-MK2/F/A cells. An aliquot of the culture supernatant was assessed for vector collection by hemagglutination assay. The culture supernatant was harvested after sufficient hemagglutination was observed. RNA was extracted from the harvested culture supernatant using the QIAamp Viral RNA Mini Kit (QIAGEN, catalog No. 52906), and then subjected to RT-PCR that targets a region of the inserted KLF4-OCT3/4-SOX2 genes. Whether the obtained RT-PCR product has the correct nucleotide sequence was confirmed by sequencing. Thus, the SeV(PM) KOS/TSΔF vector was obtained.

Example 4

Preparation of Plasmids for Production of SeV Vectors Carrying the OCT3/4-SOX2-KLF4 Genes The OCT3/4 gene was amplified by PCR (95° C. for three minutes, and 30 cycles of [98° C. for ten seconds, 55° C. for 15 seconds, and 72° C. for 2 minutes], followed by 72° C. for seven minutes) using PrimeStar HS DNA Polymerase (Takara Bio, catalog No. R010A); pSeV18+OCT3/4/TSΔF (WO 2010/008054) as template; and primers F6 (5'-ACAA-GAGAAAAAACATGTATGG-3') (SEQ ID NO: 18) and OSK-OS-R (5'-GGCGGCGTGTTAGGTGGAT-GACTTTCACCCTAAGTTTTTCTTAC-TACGGTCAGTTTGA ATGC-3') (SEQ ID NO: 19). The PCR product was purified using the Qiaquick PCR Purification Kit (QIAGEN, catalog No. 28106) and eluted with 100 μl of an elution solution attached to the kit.

The SOX2 gene was amplified by PCR (95° C. for three minutes, and 30 cycles of [98° C. for ten seconds, 55° C. for 15 seconds, and 72° C. for 2 minutes], followed by 72° C. for seven minutes) using PrimeStar HS DNA Polymerase (Takara Bio, catalog No. R010A); pSeV18+SOX2/TSΔF (WO 2010/008054) as template; and primers OSK-OS-F (5'-TAGTAAGAAAAACTTAGGGTGAAAGT-CATCCACCTAACACGCCGCCATGTACAACA TGATG-GAG-3') (SEQ ID NO: 20) and OSK-SK-R (5'-TGTTAGGTGGATGAACTTTCACCCTAAGTTTTTCTT-ACTACGGTCACATGTGTGAGA GGG-3') (SEQ ID NO: 21). The PCR product was purified using the Qiaquick PCR Purification Kit (QIAGEN, catalog No. 28106) and eluted with 100 μl of an elution solution attached to the kit.

The KLF4 gene was amplified by PCR (95° C. for three minutes, and 30 cycles of [98° C. for ten seconds, 55° C. for 15 seconds, and 72° C. for 2 minutes], followed by 72° C. for seven minutes) using PrimeStar HS DNA Polymerase (Takara Bio, catalog No. R010A); pSeV18+KLF4/TSΔF (WO 2010/008054) as template; and primers OSK-SK-F (5'-TAGTAAGAAAAACTTAGGGTGAAAGT-TCATCCACCTAACACGCCGCCATGGCTGTC AGC-GACGC-3') (SEQ ID NO: 22) and R199 (5'-GATAACAGCACCTCCTCCCGACT-3') (SEQ ID NO: 23). The PCR product was purified using the Qiaquick PCR Purification Kit (QIAGEN, catalog No. 28106) and eluted with 100 μl of an elution solution attached to the kit.

A second PCR was performed using these purified PCR products. PrimeStar HS DNA Polymerase (Takara Bio, catalog No. R010A) was used, and 1 μL each of the above-mentioned purified OCT3/4 gene PCR product, the SOX2 gene PCR product, and the KLF4 gene PCR product were added. F6 (5'-ACAAGAGAAAAACATGTATGG-3') (SEQ ID NO: 18), SOX2-R470 (5'-ATGCGCTGGT-TCACGCCCGCGCCCAGG-3') (SEQ ID NO: 24), or primers SOX2-F294 (5'-AGCGCTGCACATGAAGGAGCACC-3') (SEQ ID NO: 25) and KLF4-R405 (5'-CGCGCTGGCAGGGCCGCTGCTCGAC-3') (SEQ ID NO: 26) were used as primers, and PCR was carried out (95° C. for three minutes, and 30 cycles of [98° C. for ten seconds, 55° C. for 30 seconds, and 72° C. for 4 minutes], followed by 72° C. for seven minutes) for amplification.

These PCR products and the above-mentioned purified KLF4 gene PCR product (0.5 μL each) were used, and with F6 (5'-ACAAGAGAAAAACATGTATGG-3') (SEQ ID NO: 18) and R150 (5'-AATGTATCGAAGGTGCTCAA-3') (SEQ ID NO: 26) as primers, PCR was carried out using PrimeStar HS DNA polymerase (Takara Bio, catalog No. R010A). The amplified band of about 3.6 kbp was excised, and purification was carried out using the Qiaquick Gel Extraction Kit (QIAGEN, catalog No. 28706). 100 μl of the elution solution attached to the kit was used for elution. This PCR product which contains the OCT3/4 gene, SOX2 gene, and KLF4 gene was digested with NotI, and purified using the Qiaquick PCR Purification Kit (QIAGEN, catalog No. 28106). This NotI fragment was cloned into the NotI site of the pSeV(PM)/TSΔF vector, and a clone that has the correct sequence was selected by sequencing to obtain pSeV(PM) OSK/TSΔF.

Example 5

Production of SeV Vectors Carrying the Human OCT3/4-SOX2-KLF4 Genes

One day before transfection, $10^6$ 293T/17 cells were seeded into each well of a 6-well plate, and cultured in a $CO_2$ incubator (under 5% $CO_2$ condition) at 37° C. Using 15 μl of TransIT-LT1 (Mirus), the 293T/17 cells were transfected with a mixture of:
0.5 μg of pCAGGS-NP, 0.5 μg of pCAGGS-P4C(−), 2 μg of pCAGGS-L (TDK), 0.5 μg of pCAGGS-T7, 0.5 μg of pCAGGS-F5R (WO 2005/071085), and 5.0 μg of the above-described Sendai virus vector plasmid pSeV(PM)OSK/TSΔF. The cells were cultured in a $CO_2$ incubator at 37° C. for two days. Then, $10^6$ cells of LLC-MK2/F/A which express the fusion protein (F protein) of Sendai virus (Li, H.-O. et al., J. Virology 74. 6564-6569 (2000); WO 00/70070) were overlaid onto the transfected 293T/17 cells in each well. Then, the cells were cultured in a $CO_2$ incubator at 37° C. for one day. On the following day, the cell culture medium was removed, and the cells were washed once with 1 ml of MEM supplemented with penicillin-streptomycin (hereinafter abbreviated as PS/MEM). 1 ml of PS/MEM containing 2.5 μg/ml trypsin (hereinafter abbreviated as Try/PS/MEM) was added to each well. The cells were cultured in a $CO_2$ incubator at 32° C. for two days. The cells were continuously cultured while exchanging the medium every three to four days, and in some cases, passaging with LLC-MK2/F/A cells. An aliquot of the culture supernatant was assessed for vector collection by hemagglutination assay. The culture supernatant was harvested after sufficient hemagglutination was observed. RNA was extracted from the harvested culture supernatant using the QIAamp Viral RNA Mini Kit (QIAGEN, catalog No. 52906), and then subjected to RT-PCR that targets a region of the inserted OCT3/4-SOX2-KLF4 genes. Whether the obtained RT-PCR product has the correct nucleotide sequence was confirmed by sequencing. Thus, the SeV(PM) OSK/TSΔF vector was obtained.

Example 6

Production of ES-Like Cells Using Sendai Virus Vectors Carrying Foreign Genes $1.5 \times 10^5$ human newborn foreskin-derived fibroblasts (BJ) (ATCC (www.atcc.org), CRL-2522) were cultured overnight in DMEM (GIBCO-BRL, 11995) containing 10% FBS (Cell Culture Bioscience Cat. No. 171012), and penicillin (100 u/mL)-streptomycin (100 μg/mL) (Nacalai Tesque, Code No. 26253 84) (hereinafter referred to as 10% FBS/PS/DMEM) in a 5% $CO_2$ incubator at 37° C.

After culturing, the vectors indicated below were administered at a concentration of MOI=3 to the cultured cells mentioned above.
Condition 1
SeV(PM)KOS/TSΔF vector
SeV18+c-rMYC/TSΔF vector (International Publication No. WO 2010/008054)
Condition 2
SeV(PM)KOS/TSΔF vector
SeV(HNL)c-rMYC/TSΔF vector (International Publication No. WO 2010/008054)
Condition 3
SeV(PM)KOS/TSΔF vector
SeV(L)c-rMYC/TSΔF vector (Fusaki et al., Proc Jpn Acad Ser B Phys Biol Sci. Vol. 85, p 348-362 (2009))
Condition 4
SeV(PM)KOS/TSΔF vector
SeV(HNL)c-rMYC/TS15ΔF vector (International Publication No. WO 2010/008054)
Condition 5
SeV(PM)KOS/TSΔF vector
Condition 6
SeV(PM)OSK/TSΔF vector
SeV18+c-rMYC/TSΔF vector
Condition 7
SeV(PM)OSK/TSΔF vector
SeV(HNL)c-rMYC/TSΔF vector
Condition 8
SeV(PM)OSK/TSΔF vector
SeV(L)c-rMYC/TSΔF vector
Condition 9
SeV(PM)OSK/TSΔF vector
SeV(HNL)c-rMYC/TS15ΔF vector
Condition 10
SeV(PM)OSK/TSΔF vector
Condition 11
SeV18+OCT3/4/TSΔF vector (International Publication No. WO 2010/008054)
SeV18+SOX2/TSΔF vector (International Publication No. WO 2010/008054)
SeV18+KLF4/TSΔF vector (International Publication No. WO 2010/008054)
SeV(HNL) c-MYC/TS15ΔF vector
Condition 12
No vector After administration of the above-mentioned vectors, the medium was exchanged every day using 10% FBS/PS/DMEM, and cells were cultured in a 5% $CO_2$ incubator at 37° C. Then, $1.0 \times 10^5$ transfected cells mentioned above were detached with 0.25% trypsin, and added to and cultured on $1.25 \times 10^5$ mitomycin-treated feeder cells (for example, MEF) prepared in gelatin-coated six-well plates. On the following day, the 10% FBS/PS/DMEM was exchanged with Primate ES Cell Culture Medium (ReproCell; RCHEMD001) (supplemented with bFGF at 4 ng/ml), and the cells were cultured in a 5% $CO_2$ incubator. The medium was exchanged every day or every two days. The medium may be a feeder cell-conditioned medium.

14 days after infection, i.e., 7 days after the cells were passaged on MEF, human ES cell-like colonies appeared at a remarkably higher efficiency under conditions when the three genes were loaded (Conditions 2, 3, and 4) in comparison to the conventional method (Condition 11). The cell conditions are shown in FIG. 1 for the conventional type and Condition 2. As seen from the photographs shown in FIG. 1, flat colonies, which were similar to those observed for human ES cells and obviously distinct from those of fibroblasts (BJ) before induction, were observed (Jikken Igaku (Experimental Medicine) Vol. 26, No. 5 (suppl.) pp. 35-40, 2008).

Figure 2:
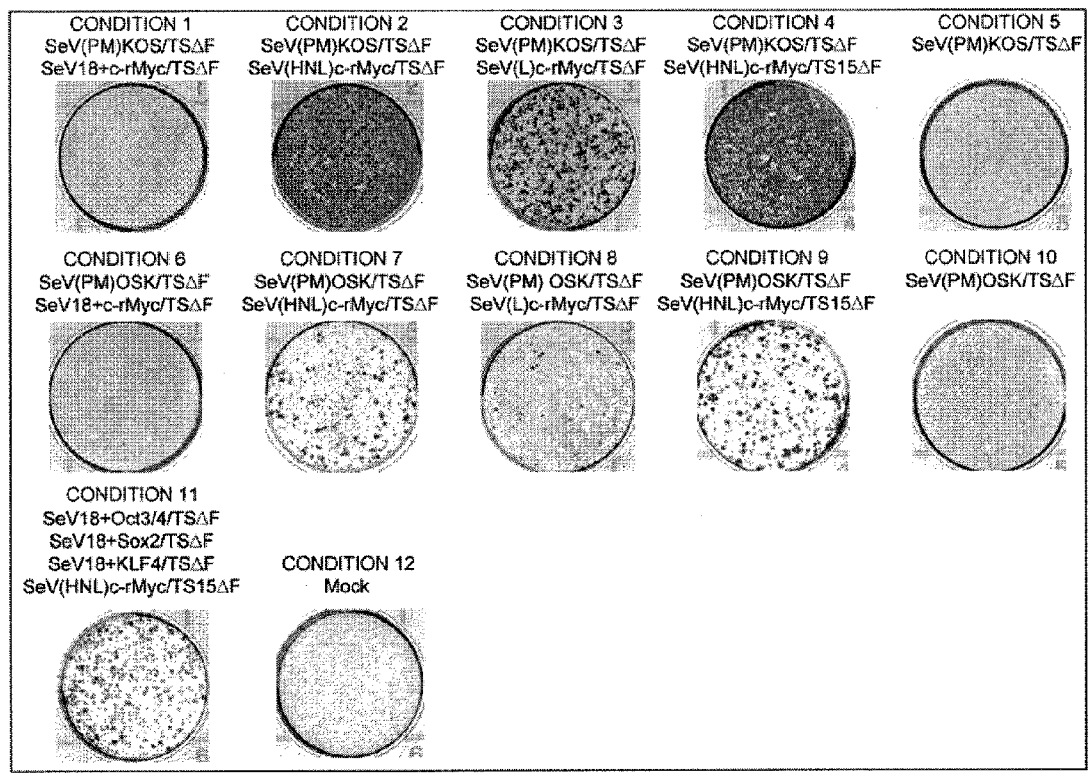
FIG. 2 shows the results when cells (BJ cells) 21 days after vector infection were stained for alkaline phosphatase. When a Sendai virus vector having the KLF4 gene, OCT3/4 gene, and SOX2 gene inserted in this order was used, alkaline phosphatase-positive colonies were detected under all test conditions (Conditions 1 to 5). Furthermore, compared to when a Sendai virus vector with insertion of the genes in a different order was used (Conditions 6 to 10) and when each of the genes were introduced using separate Sendai virus vectors (Condition 11), the frequency of appearance of alkaline phosphatase-positive colonies was remarkably high. In particular, when a different Sendai virus vector having the c-MYC gene inserted immediately before or after the Sendai virus L gene was used in combination (Conditions 2 to 4), the frequency of appearance of alkaline phosphatase-positive colonies was significantly high.
Figure 3:
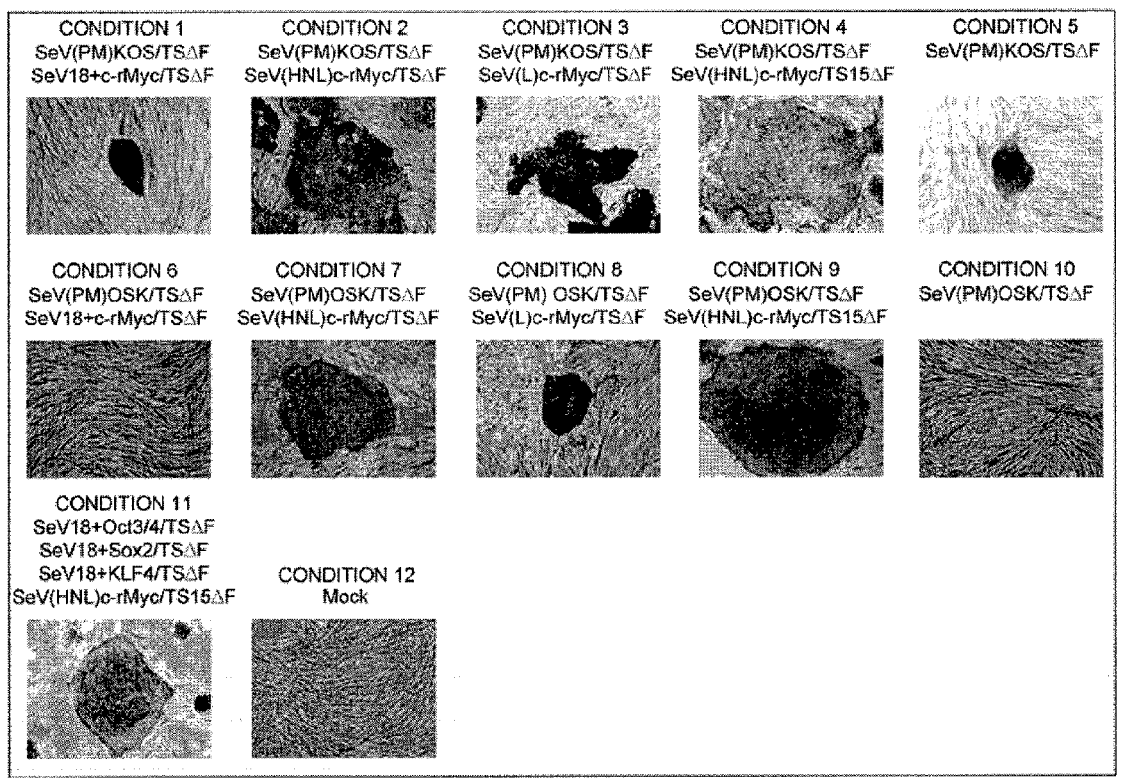
FIG. 3 shows alkaline phosphatase-stained colonies. Alkaline phosphatase-positive colonies were not detected under Conditions 6, 10, and 12.
Figure 4:
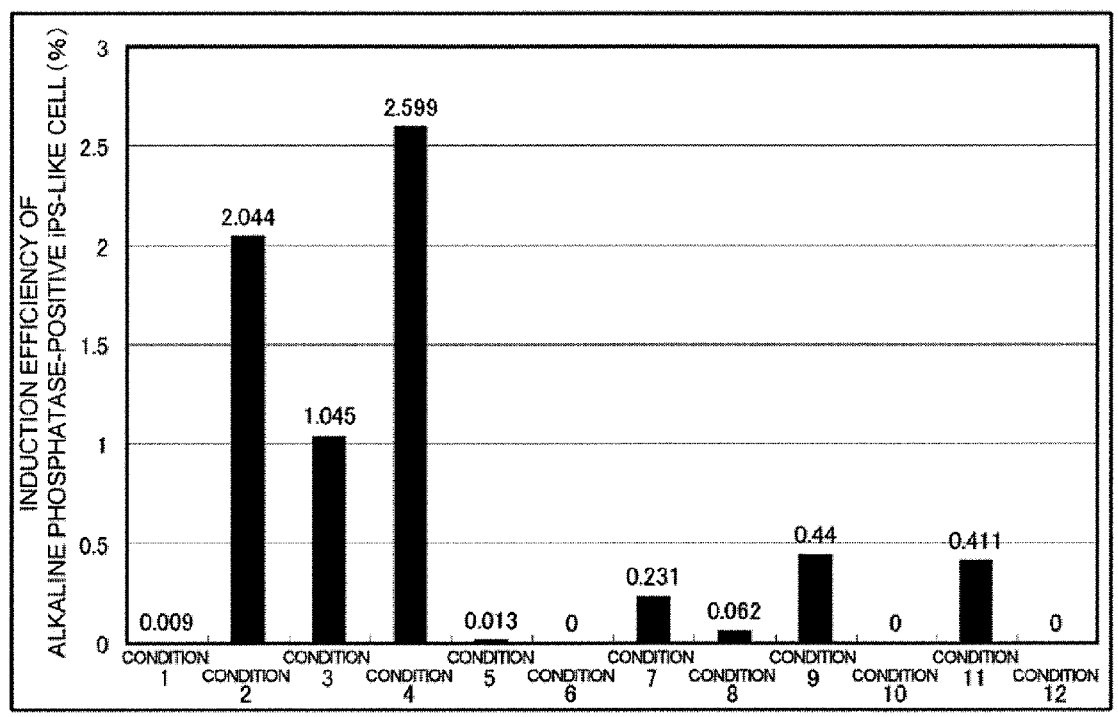
FIG. 4 presents a graph showing the induction efficiency of alkaline phosphatase-positive colonies. Efficiency of inducing pluripotent stem cells from BJ cells is shown. The conditions were the same as those in FIG. 3.

The activity of alkaline phosphatase which is an ES cell undifferentiation marker was visualized by staining with NBCT/BCIP (PIERCE; NBT/BCIP, 1-Step, #34042) on day 21 of infection. In comparison with the conventional condition (Condition 11 described above) and the OSK gene alignment (OCT-SOX-KLF), a great number of alkaline phosphatase-positive blue-stained colonies were observed in Conditions 2, 3, and 4 which used vectors with the KOS gene alignment (KLF-OCT-SOX) (FIGS. 2 and 3). This way, the induction efficiency of alkaline phosphatase-positive iPS-like cells was found to be specifically high in vectors having the KOS gene alignment (KLF-OCT-SOX) (FIG. 4).

Example 7

$1.5 \times 10^5$ human fetus-derived fibroblasts (MRC-5) (ATCC (www.atcc.org), CCL-171) were cultured overnight in DMEM (GIBCO-BRL, 11995) containing 10% FBS (Cell Culture Bioscience Cat. No. 171012), and penicillin (100 u/mL)-streptomycin (100 μg/mL) (Nacalai Tesque, Code No. 26253-84) (hereinafter referred to as 10% FBS/PS/DMEM) in a 5% $CO_2$ incubator at 37° C.

After culturing, the vectors were administered to the cultured cells mentioned above under the conditions indicated below.
Condition 1
SeV(PM)KOS/TSΔF vector Moi=3
SeV(HNL)c-rMYC/TS15ΔF vector Moi=3
Condition 2
SeV(PM)KOS/TSΔF vector Moi=3
SeV(HNL)c-rMYC/TS15ΔF vector Moi=9
Condition 3
SeV(PM)KOS/TSΔF vector Moi=3
SeV(HNL)c-rMYC/TS15ΔF vector Moi=30
Condition 4
SeV(PM)KOS/TSΔF vector Moi=3
SeV(HNL)c-rMYC/TS15ΔF vector Moi=90
Condition 5
SeV(PM)OSK/TSΔF vector Moi=3
SeV(HNL)c-rMYC/TS15ΔF vector Moi=3
Condition 6
SeV(PM)OSK/TSΔF vector Moi=3
SeV(HNL)c-rMYC/TS15ΔF vector Moi=9
Condition 7
SeV(PM)OSK/TSΔF vector Moi=3
SeV(HNL)c-rMYC/TS15ΔF vector Moi=30
Condition 8
SeV(PM)OSK/TSΔF vector Moi=3 SeV(HNL)c-rMYC/TS15ΔF vector Moi=90
Condition 9
SeV18+OCT3/4/TSΔF vector Moi=3
SeV18+SOX2/TS15ΔF vector Moi=3
SeV18+KLF4/TSΔF vector Moi=3
SeV(HNL) c-rMYC/TS15ΔF vector Moi=3
Condition 10
SeV18+OCT3/4/TSΔF vector Moi=3
SeV18+SOX2/TSΔF vector Moi=3
SeV18+KLF4/TSΔF vector Moi=3
SeV(HNL) c-rMYC/TS15ΔF vector Moi=9

Condition 11
SeV18+OCT3/4/TSΔF vector Moi=3
SeV18+SOX2/TSΔF vector Moi=3
SeV18+KLF4/TSΔF vector Moi=3
SeV(HNL) c-rMYC/TS15ΔF vector Moi=30
Condition 12
SeV18+OCT3/4/TSΔF vector Moi=3
SeV18+SOX2/TSΔF vector Moi=3
SeV18+KLF4/TSΔF vector Moi=3
SeV(HNL) c-rMYC/TS15ΔF vector Moi=90
Condition 13
No vector After administration of the above-mentioned vectors, the medium was exchanged every day using 10% FBS/PS/DMEM, and cells were cultured in a 5% $CO_2$ incubator at 37° C. Then, $1.0×10^5$ transfected cells mentioned above that were detached with 0.25% trypsin were added to and cultured on $1.25×10^5$ mitomycin-treated feeder cells (for example, MEF) prepared in gelatin-coated six-well plates. On the following day, the 10% FBS/PS/DMEM was exchanged with Primate ES Cell Culture Medium (ReproCell; RCHEMD001) (supplemented with bFGF at 4 ng/ml) and the cells were cultured in a 5% $CO_2$ incubator. The medium was exchanged every day or every two days. The medium may be a feeder cell-conditioned medium.

Figure 5:
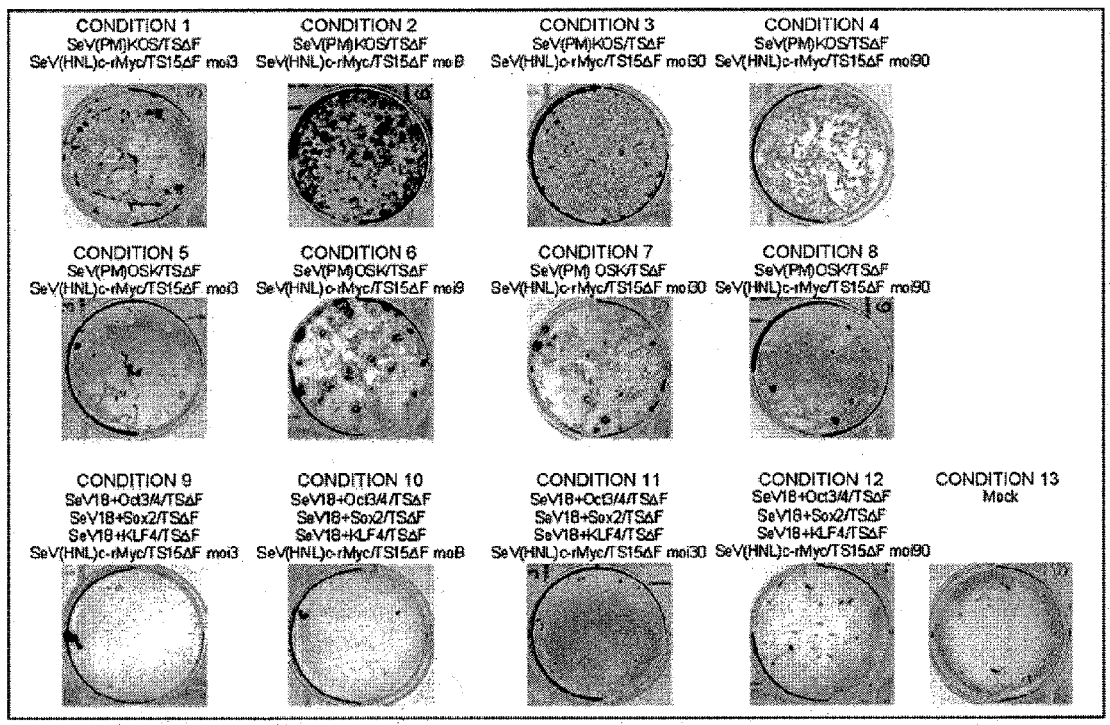
FIG. 5 shows the results when cells (MRC-5 cells) 27 days after vector infection were stained for alkaline phosphatase. Compared to the conventional method (Condition 9), human ES cell-like colonies appeared at a significantly high efficiency under conditions when the three genes were loaded (Conditions 1 to 8), in particular under a condition when the MOI was less than 90 (Conditions 1 to 3 and 5 to 7). Furthermore, when a Sendai virus vector with insertion of the KLF4 gene, OCT3/4 gene, and SOX2 gene in this order was used, alkaline phosphatase-positive colonies were induced at a significantly high efficiency. Furthermore, when a Sendai virus vector with insertion of the OCT3/4 gene, SOX2 gene, and KLF4 gene in this order was used, alkaline phosphatase-positive colonies were induced at a clearly higher efficiency than that when these genes were introduced using separate Sendai virus vectors.
Figure 6:
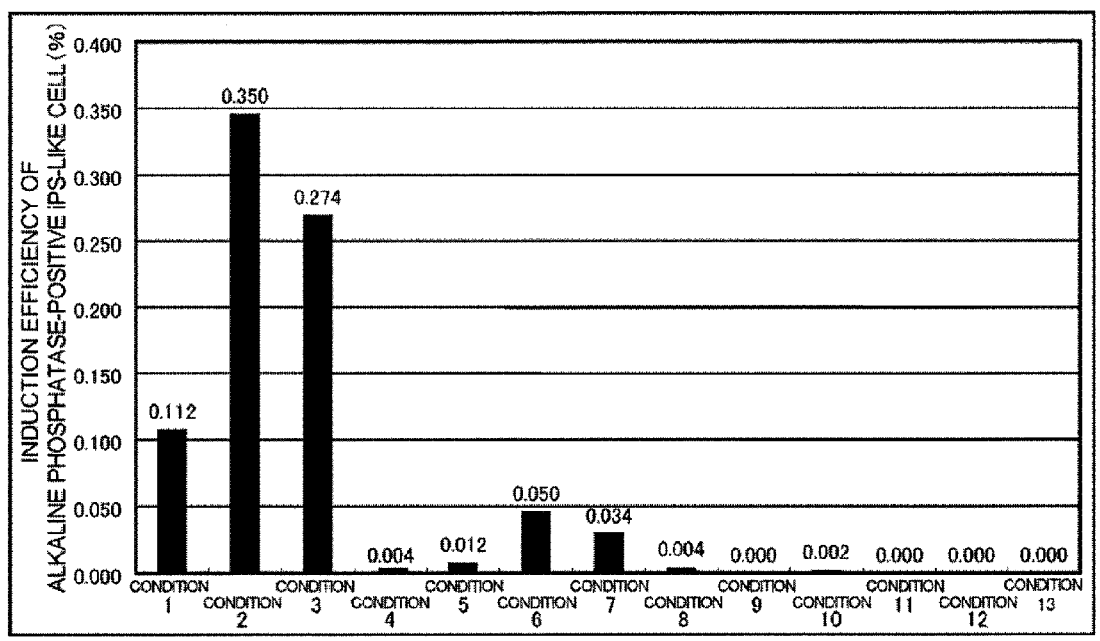
FIG. 6 presents a graph showing the induction efficiency of alkaline phosphatase-positive colonies. Efficiency of inducing pluripotent stem cells from MRC-5 cells is shown. The conditions were the same as those in FIG. 5.

27 days after infection, i.e., 21 days after the cells were passaged on MEF, the rate of human ES cell-like visible colonies was significantly increased under conditions in which three genes were loaded (Conditions 1 to 8) than under the conventional method (Conditions 9 to 12), and in particular, human ES cell-like colonies became visible with high efficiency under conditions of less than MIO=90 (Conditions 1 to 3 and 5 to 7). When the activity of alkaline phosphatase which is an ES cell undifferentiation marker was visualized by staining with NBCT/BCIP (PIERCE; NBT/BCIP, 1-Step, #34042), colonies stained blue, which were positive for alkaline phosphatase, were efficiently observed under Conditions 1 to 8, in particular 1 to 3 and 5 to 7 which used vectors with genes lined up in the order of KOS (KLF-OCT-SOX) or OSK (OCT-SOX-KLF) compared to the conventional condition (Conditions 9 to 12 described above) (FIG. 5). The efficiency of induction of alkaline phosphatase-positive iPS-like cells was more efficient as compared to the conventional conditions (FIG. 6). The induction efficiency was significantly high when vectors in which the genes are positioned in the order of KOS (KLF-OCT-SOX) compared to when vectors in which the genes are positioned in the order of OSK (OCT-SOX-KLF).

Example 8

Construction of pSeV(PM)/TS7ΔF pSeV(PM)/TSΔF was digested with PmlI and XhoI, a band of about 12.7 kbp was excised, and this was purified using the QIAquick Gel Extraction Kit. pSeV18+Oct3/4/TS7ΔF (International Publication No. WO 2010/008054) was digested with NotI, and separated by agarose gel electrophoresis. Then, a band of about 16.4 Kbp was excised, and this was purified using the QIAquick Gel Extraction Kit. Then, self-ligation was carried out, and a clone containing the Oct3/4 gene but not the NotI fragment was selected to obtain pSeV18+/TS7ΔF. pSeV18+/TS7ΔF was digested with PmlI and XhoI, a band of about 3.6 kbp was excised, and this was purified using the QIAquick Gel Extraction Kit. These two purified products were used and ligated, and a clone that has the correct sequence was selected by sequencing to obtain pSeV(PM)/TS7ΔF. This vector has an insertion site (NotI site) for gene introduction between the P gene and M gene.

Example 9

Production of Plasmids for Generation of SeV/TS7ΔF Vectors Carrying the KLF4-OCT3/4-SOX2 Genes pSeV(PM)/TS7ΔF was digested with NotI, then purified using the QIAquick PCR Purification Kit, and then subjected to BAP treatment. Then, this was purified using the QIAquick PCR Purification Kit. pSeV(PM)KOS/TSΔF was digested with NotI, separated by 1% agarose gel electrophoresis, a band of about 3.6 kbp was excised, and purification was carried out using the Qiaquick Gel Extraction Kit (QIAGEN, catalog No. 28706). 100 µl of an elution solution attached to the kit was used for elution. The NotI fragment containing the KLF4 gene, the OCT3/4 gene, and the SOX2 gene was cloned into the NotI site of the pSeV(PM)/TS7ΔF vector. Then, a clone that has the correct sequence was selected by sequencing. Thus, pSeV(PM)KOS/TS7ΔF was obtained.

Example 10

Production of SeV/TS7ΔF Vectors Carrying the Human KLF4-OCT3/4-SOX2 Genes

Using 15 µl of TransIT-LT1 (Mirus), the 293T/17 cells (Human embryonic kidney subclone 17, ATCC CRL-11286, Pear, W. S. et al., 1993, Proc. Natl. Acad. Sci. USA 90: 8392-8396) were transfected with a mixture of:
0.5 µg of pCAGGS-NP, 0.5 µg of pCAGGS-P4C (−), 2 µg of pCAGGS-L (TDK), 0.5 µg of pCAGGS-T7, 0.5 µg of pCAGGS-F5R (WO 2005/071085), and 5.0 µg of an above-described Sendai virus vector plasmid pSeV(PM)KOS/TS7ΔF. The cells were cultured in a $CO_2$ incubator at 37° C. for three days. Then, $10^6$ cells of LLC-MK2/F/A which express the fusion protein (F protein) of Sendai virus were overlaid onto the transfected 293T/17 cells in each well. Then, the cells were cultured in a $CO_2$ incubator at 37° C. for one day. On the following day, the cell culture medium was removed, and the cells were washed once with 1 ml of MEM supplemented with penicillin-streptomycin (hereinafter abbreviated as PS/MEM). 1 ml of PS/MEM containing 2.5 µg/ml trypsin (hereinafter abbreviated as Try/PS/MEM) was added to each well. The cells were cultured in a $CO_2$ incubator at 32° C. for two days. Thereafter, the cells were continuously cultured while appropriately exchanging the medium, and in some cases, passaging with LLC-MK2/F/A cells. An aliquot of the culture supernatant was assessed for vector collection by hemagglutination assay. The culture supernatant was harvested after sufficient hemagglutination was observed. RNA was extracted from the harvested culture supernatant using the QIAamp Viral RNA Mini Kit (QIAGEN, catalog No. 52906), and then subjected to RT-PCR that targets a region of the inserted KLF4-OCT3/4-SOX2 genes. Whether the obtained RT-PCR product has the correct nucleotide sequence was confirmed by sequencing. Thus, the SeV(PM) KOS/TS7ΔF vector was obtained.

Example 11

Construction of pSeV(PM)/TS12ΔF

PCR (94° C. for three minutes, and 30 cycles of [98° C. for 10 seconds, 55° C. for 15 seconds, and 72° C. for 1.5 minutes], followed by 72° C. for five minutes, and cc at 4° C.) was carried out using PrimeSter, with pSeV(PM)/TSΔF as template, and primers F3208 (5'-AGAGAACAAGACTAAGGCTACC-3' (SEQ ID NO: 27)) and R3787 (5'-ACCTTGACAATCCTGATGTGG-3' (SEQ ID NO: 28)). The amplified band of about 600 bp was purified using the QIAquick PCR Purification Kit. PCR (94° C. for three minutes, and 30 cycles of [98° C. for 10 seconds, 55° C. for 15 seconds, and 72° C. for 1.5 minutes], followed by 72° C. for five minutes, and ∞ at 4° C.) was carried out using PrimeSter, with pSeV18+Oct3/4/TS12ΔF (WO 2010/008054) as template, and primers F2001 (5'-CCATCAACACTCCCCAAGGACC-3' (SEQ ID NO: 29)) and R3390 (5'-AGACGTGATGCGTTTGAGGCCC-3' (SEQ ID NO: 30)). The amplified band of about 1.4 kbp was purified using the QIAquick PCR Purification Kit. These PCR products were mixed, and PCR (94° C. for three minutes, and 30 cycles of [98° C. for 10 seconds, 55° C. for 15 seconds, and 72° C. for two minutes], followed by 72° C. for five minutes, and cc at 4° C.) was carried out using PrimeSter, and the F2001 and R3787 primers. The PCR products were purified using the QIAquick PCR Purification Kit, digested with SalI and NotI, and then separated by agarose gel electrophoresis. Then, a band of about 1.6 kbp was excised, and purified using the QIAquick Gel Extraction Kit. pSeV(PM)/TSΔF was digested with SalI and NotI, and then separated by agarose gel electrophoresis. Then, a band of about 14.8 kbp was excised, and purified using the QIAquick Gel Extraction Kit. These two SalI and NotI-digested and purified products were used for ligation, and a clone that has the correct sequence was selected by sequencing to obtain pSeV(PM)/TS12ΔF. This vector has an insertion site (NotI site) for gene introduction between the P gene and M gene.

Example 12

Production of Plasmids for Production of SeV/TS12ΔF Vectors Carrying the KLF4-OCT3/4-SOX2 Genes pSeV(PM)/TSΔF was digested with NotI, then purified using the QIA quick PCR Purification Kit (QIAGEN catalogue No. 28106), and then subjected to BAP treatment. Then, this was purified using the QIAquick PCR Purification Kit. pSeV(PM)KOS/TSΔF was digested with NotI, separated by 1% agarose gel electrophoresis, a band of about 3.6 kbp was excised, and purification was carried out using the Qiaquick Gel Extraction Kit (QIAGEN, catalog No. 28706). 100 ul of an elution solution attached to the kit was used for elution. The NotI fragment containing the KLF4 gene, the OCT3/4 gene, and the SOX2 gene was cloned into the NotI site of the pSeV(PM)/TS12ΔF vector, and a clone that has the correct sequence was selected by sequencing. Thus, pSeV(PM)KOS/TS12ΔF was obtained.

Example 13

Production of SeV/TS12ΔF Vectors Carrying the Human KLF4-OCT3/4-SOX2 Genes

Using 15 µl of TransIT-LT1 (Mirus), the 293T/17 cells (Human embryonic kidney subclone 17, ATCC CRL-11286, Pear, W. S. et al., 1993, Proc. Natl. Acad. Sci. USA 90: 8392-8396) were transfected with a mixture of:
0.5 µg of pCAGGS-NP, 0.5 µg of pCAGGS-P4C (−), 2 µg of pCAGGS-L (TDK), 0.5 µg of pCAGGS-T7, 0.5 µg of pCAGGS-F5R (WO 2005/071085), and 5.0 µg of an above-described Sendai virus vector plasmid pSeV(PM)KOS/TS12ΔF. The cells were cultured in a $CO_2$ incubator at 37° C. for three days. Then, $10^6$ cells of LLC-MK2/F/A which express the fusion protein (F protein) of Sendai virus were overlaid onto the transfected 293T/17 cells in each well. Then, the cells were cultured in a $CO_2$ incubator at 37° C. for one day. On the following day, the cell culture medium was removed, and the cells were washed once with 1 ml of MEM supplemented with penicillin-streptomycin (hereinafter abbreviated as PS/MEM). 1 ml of PS/MEM containing 2.5 µg/ml trypsin (hereinafter abbreviated as Try/PS/MEM) was added to each well. The cells were cultured in a $CO_2$ incubator at 32° C. for two days. Thereafter, the cells were continuously cultured while appropriately exchanging the medium, and in some cases, passaging with LLC-MK2/F/A cells. An aliquot of the culture supernatant was assessed for vector collection by hemagglutination assay. The culture supernatant was harvested after sufficient hemagglutination was observed. RNA was extracted from the harvested culture supernatant using the QIAamp Viral RNA Mini Kit (QIAGEN, catalog No. 52906), and then subjected to RT-PCR that targets a region of the inserted KLF4-OCT3/4-SOX2 genes. Whether the obtained RT-PCR product has the correct nucleotide sequence was confirmed by sequencing. Thus, the SeV(PM) KOS/TS12ΔF vector was obtained.

Example 14

Induction of iPS Cells from Human Newborn Foreskin-Derived Fibroblast (BJ) by Temperature-Sensitive Sendai Virus Vectors Carrying Foreign Genes $2.0 \times 10^5$ human newborn foreskin-derived fibroblasts (BJ) (ATCC (www.atcc.org), CRL-2522) were plated onto 12-well plates using DMEM (GIBCO-BRL, 11995) supplemented with 10% FBS (Cell Culture Bioscience Cat. No. 171012), and penicillin (100 u/mL)-streptomycin (100 µg/mL) (Nacalai Tesque, Code No. 26253-84) (hereinafter referred to as 10% FBS/PS/DMEM), and the cells were cultured overnight in a 5% $CO_2$ incubator at 37° C.

After culturing, the vectors were administered to the cultured cells mentioned above under the conditions indicated below.
Condition 1: Conventional type
SeV18+OCT3/4/TSΔF vector Moi=3
SeV18+SOX2/TSΔF vector Moi=3
SeV18+KLF4/TSΔF vector Moi=3
SeV(HNL) c-rMYC/TS15ΔF vector Moi=3
Condition 2
SeV(PM) OSK/TSΔF vector Moi=3
SeV18+KLF4/TSΔF vector Moi=3
SeV(HNL)c-rMYC/TS15ΔF vector Moi=3
Condition 3
SeV(PM)KOS/TSΔF vector Moi=3
SeV(HNL)c-rMYC/TS15ΔF vector Moi=3
Condition 4
SeV(PM)KOS/TS7ΔF vector Moi=30
SeV(HNL)c-rMYC/TS15ΔF vector Moi=30
Condition 5
SeV(PM)KOS/TS12ΔF vector Moi=30
SeV(HNL)c-rMYC/TS15ΔF vector Moi=30
Condition 6
No vector
After administration of the above-mentioned vectors, the medium was exchanged every day using 10% FBS/PS/DMEM, and cells were cultured in a 5% $CO_2$ incubator at 36° C. or 37° C. Then, $1.0 \times 10^5$ transfected cells mentioned above were detached with 0.25% trypsin, and added to and cultured on 1.25×10⁵ mitomycin-treated feeder cells (for example, MEF) prepared in gelatin-coated six-well plates. On the following day, the 10% FBS/PS/DMEM medium was exchanged with Primate ES Cell Culture Medium (Repro-Cell; RCHEMD001) (supplemented with bFGF at 4 ng/ml), and the cells were cultured in a 5% $CO_2$ incubator at 36° C. or 37° C. The medium was exchanged every day or every two days. The medium may be a feeder cell-conditioned medium.

Figure 7:
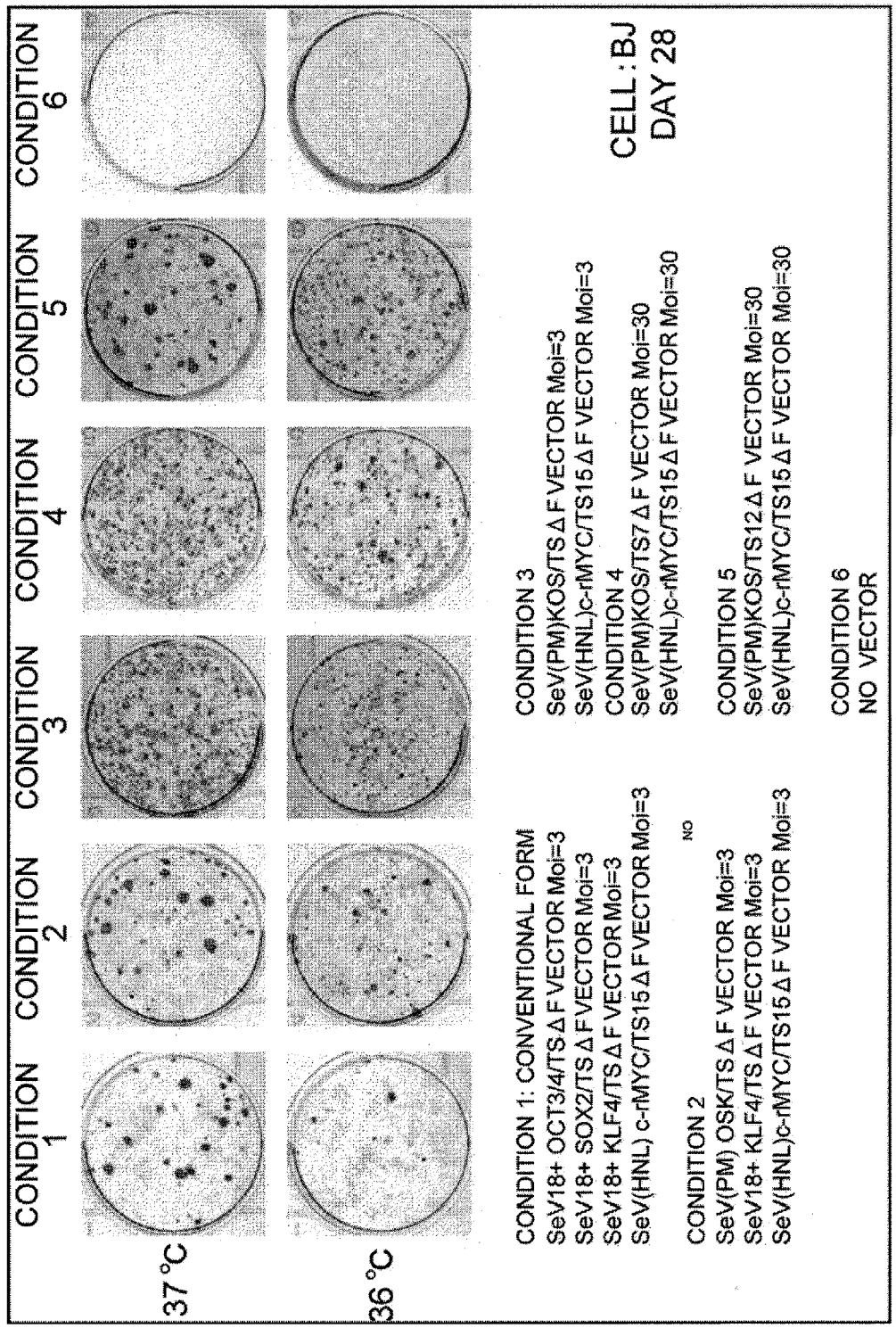
FIG. 7 shows the result when cells after vector infection were stained for alkaline phosphatase.
Figure 8:
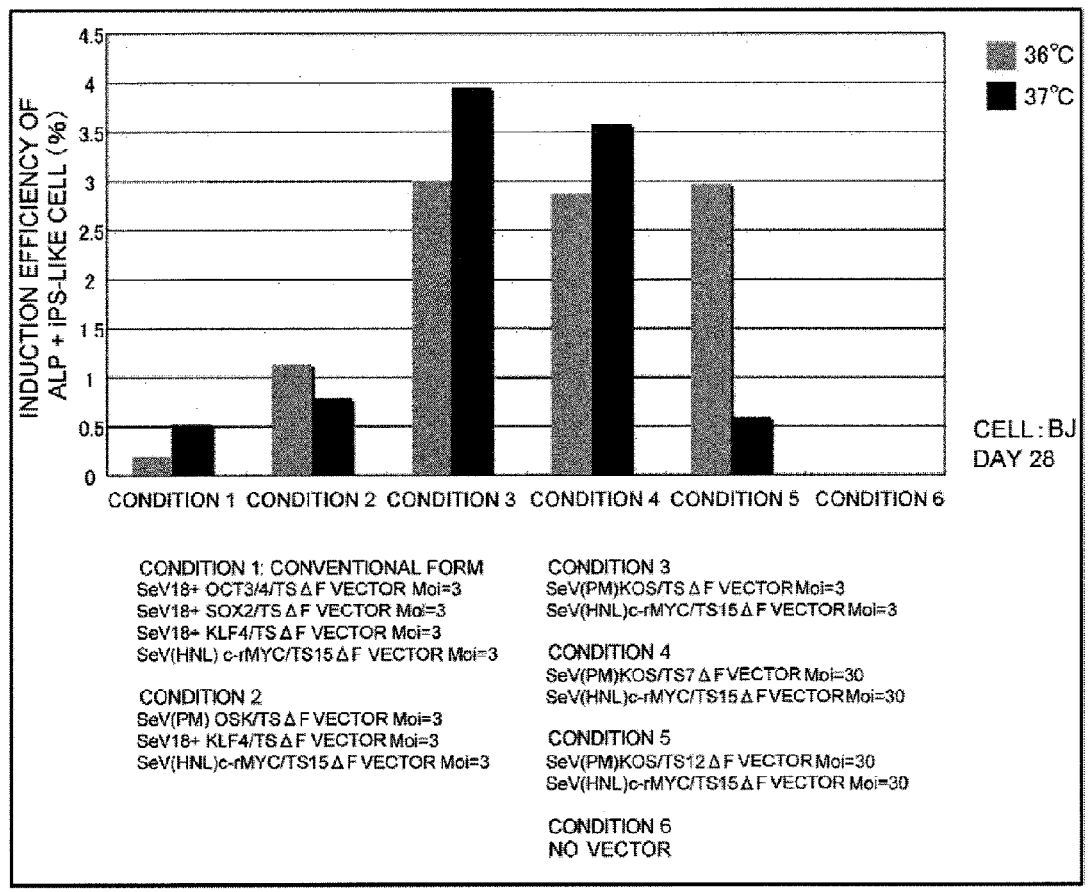
FIG. 8 shows the induction efficiency of alkaline phosphatase-positive colonies.

The activity of alkaline phosphatase which is an ES cell undifferentiation marker was visualized by staining with NBCT/BCIP (PIERCE; NBT/BCIP, 1-Step, #34042) on day 28 of infection. Alkaline phosphatase-positive, blue-stained colonies were observed under conditions that used vectors carrying KOS (KLF-OCT-SOX) in comparison with the conventional condition (Condition 1 described above) (FIG. 7). When temperature-sensitive vectors were used, alkaline phosphatase-positive iPS-like cells were induced more efficiently at 36° C. The induction efficiencies of alkaline phosphatase-positive iPS-like cells under the respective conditions are shown in FIG. 8. Even when temperature-sensitive Sendai virus vectors simultaneously loaded with three reprogramming factors were used, the induction efficiencies of alkaline phosphatase-positive iPS-like cells were shown to be higher than those under conventional conditions. In addition to the conditions indicated herein, use of the SeV(PM)KOS/TS12ΔF vector and the SeV(HNL)c-rMYC/TS12ΔF vector (a vector carrying the TS12 mutation and loaded with c-rMYC between HN and L, which was produced by using pSeV18+c-rMyc/TS12ΔF described in WO 2010/008054), and use of the SeV(PM)KOS/TS12ΔF vector and the SeV(HNL)c-rMYC/TS13ΔF vector (a vector carrying the TS13 mutation and loaded with c-rMYC between HN and L, which was produced by using pSeV18+c-rMyc/TS13ΔF described in WO 2010/008054) were also successful in efficiently inducing alkaline phosphatase-positive iPS-like cells. In addition, iPS cells were successfully induced from cells besides BJ cells, such as human adult skin-derived fibroblasts HDF (Applications, Inc. 106-05A-1388; derived from the cheek of a 36-year-old white adult female) and human fetal lung cell-derived fibroblasts (MRC5; ATCC CCL-171).

Example 15

ES Marker Expression in iPS Cells by RT-PCR

Figure 9:
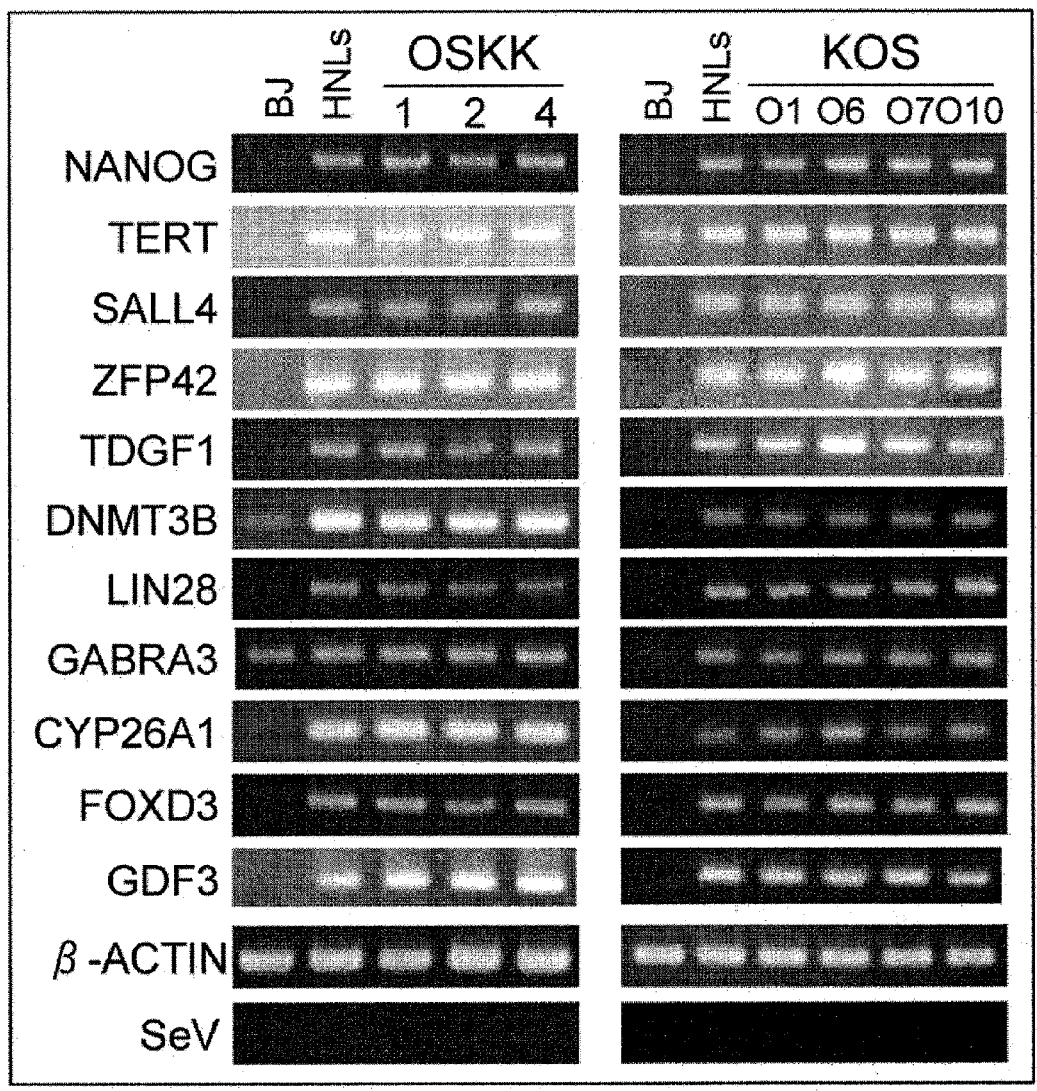
FIG. 9 shows the results of analyzing the expression of ES marker genes.

To confirm whether the iPS cells induced by Sendai virus vectors simultaneously carrying the three reprogramming factors express the ES marker genes, total RNAs were extracted from strains of iPS clones KOS-O1, KOS-O6, KOS-O7, and KOS-O10 (derived from BJ cells) established by induction using SeV(PM)KOS/TSΔF and SeV(HNL)c-rMYC/TS15ΔF, and iPS clones OSKK1, OSKK2, and OSKK4 (derived from BJ cells) established by induction using SeV(PM)OSK/TSΔF, SeV(HNL)c-rMYC/TS15ΔF, and SeV18+KLF4/TSΔF. RT reactions were carried out using random primers; and PCR was performed using primers for detecting the respective genes. The ES cell markers evaluated were NANOG, TERT, SALL4, ZFP42, TDGF1, DNMT3B, LIN28, GABRA3, CYP26A1, FOXD3, and GDF3. As an internal control, β-ACTIN was used. Furthermore, PCR was performed to detect Sendai virus vectors. As shown in FIG. 9, expression of all ES marker genes evaluated was confirmed in the iPS cells induced by the Sendai virus vectors simultaneously carrying three reprogramming factors. Meanwhile, Sendai virus vector RNAs were not detected.

Figure 10:
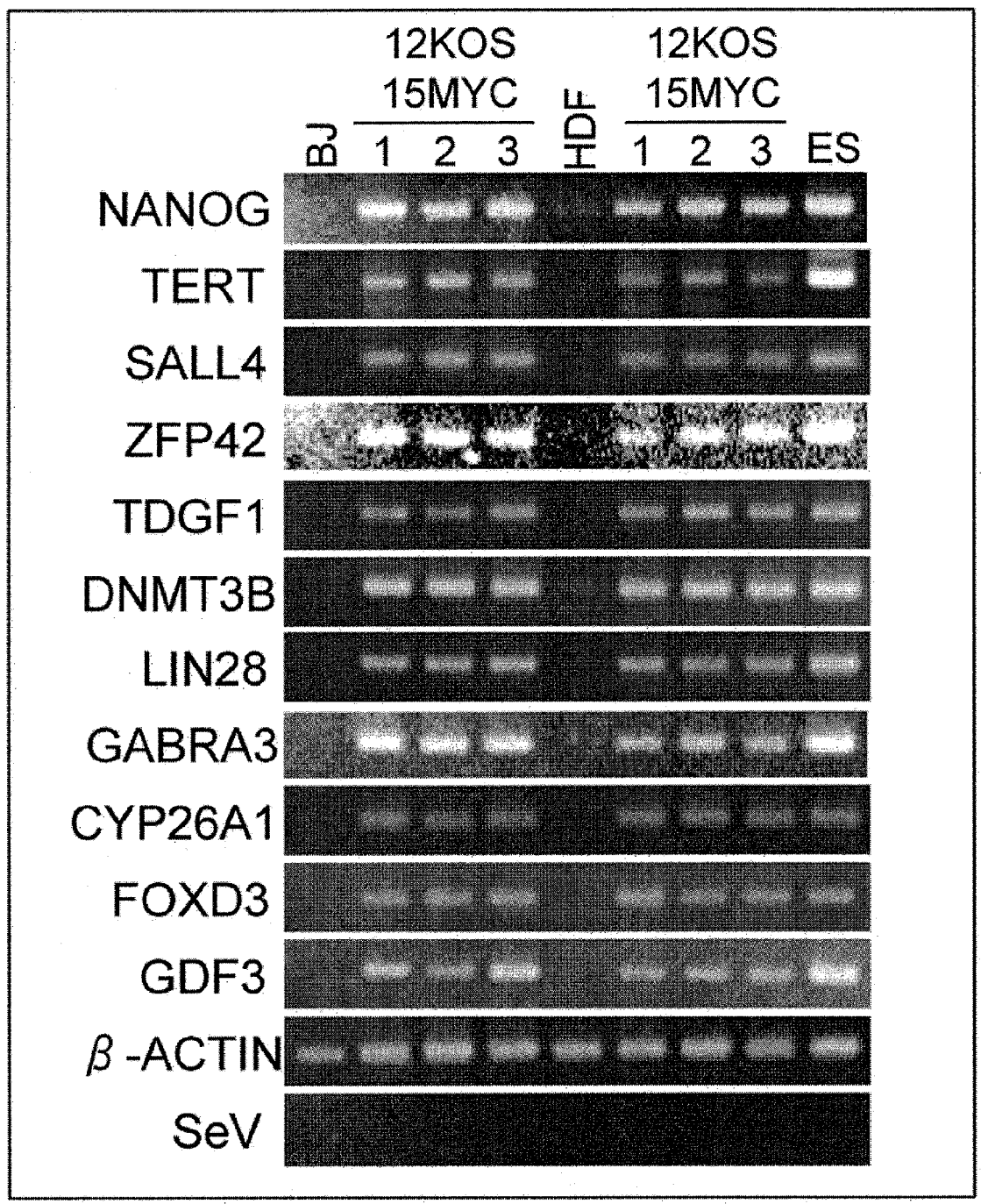
FIG. 10 shows the results of analyzing the expression of ES marker genes.

Similarly, expression of all the ES marker genes evaluated was also confirmed in iPS clones (derived from BJ cells and HDF cells) established by induction at 36° C. using SeV(PM)KOS/TS12ΔF and SeV(HNL)c-rMYC/TS15ΔF (FIG. 10).

Figure 11:
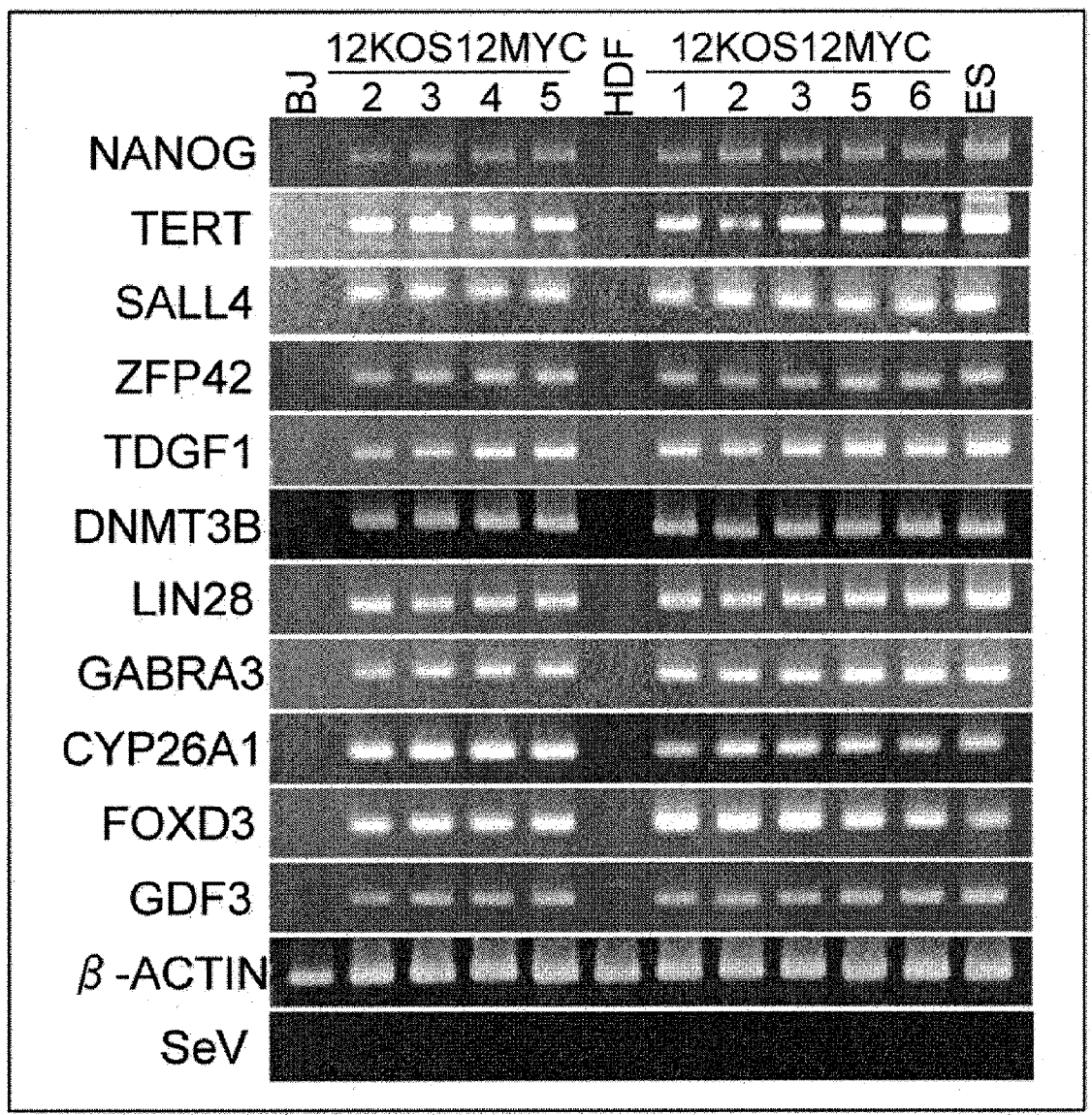
FIG. 11 shows the results of analyzing the expression of ES marker genes.

Expression of all the ES marker genes evaluated was also confirmed in iPS clones (derived from BJ cells and HDF cells) established by induction at 37° C. using SeV(PM)KOS/TS12ΔF and SeV(HNL)c-rMYC/TS12ΔF, and culturing for 7 days at 39° C. (FIG. 11). Meanwhile, Sendai virus vector RNAs were not detected.

The respective primers used are as shown below.

```
NANOG
                                     (SEQ ID NO: 31)
NANOG-F  (CCACCATGAGTGTGGATCCAGCTTGTCC);
and (SEQ ID NO: 32)
NANOG-R  (CTCACACGTCTTCAGGTTGCATGTTC)

TERT
                                     (SEQ ID NO: 33)
TERT F2847  (TGCCCGGACCTCCATCAGAGCCAG);
and (SEQ ID NO: 34)
TERT R3399  (TCAGTCCAGGATGGTCTTGAAGTCTG)

Sall4
                                     (SEQ ID NO: 35)
Sall4 F  (AAACCCCAGCACATCAACTC);
and (SEQ ID NO: 36)
Sall4 R  (GTCATTCCCTGGGTGGTTC)

Zfp42
                                     (SEQ ID NO: 37)
Zfp42-F1  (ATGAGCCAGCAACTGAAGAAACGGGCAAAG);
and (SEQ ID NO: 38)
Zfp42-R933  (CTACTTTCCCTCTTGTTCATTCTTGTTCG)

TDGF1
                                     (SEQ ID NO: 39)
TDGF1-F1  (ATGGACTGCAGGAAGATGGCCCGC);
and (SEQ ID NO: 40)
TDGF1-R567  (TTAATAGTAGCTTTGTATAGAAAGGC)

Dmmt3b
                                     (SEQ ID NO: 41)
Dnmt3b F  (GCAGCGACCAGTCCTCCGACT);
and (SEQ ID NO: 42)
Dnmt3b R  (AACGTGGGGAAGGCCTGTGC)

LIN28
                                     (SEQ ID NO: 43)
LIN28-F  (CCACCATGGGCTCCGTGTCCAACCAGC);
and (SEQ ID NO: 44)
LIN28-R  (GTCAATTCTGTGCCTCCGGGAGC)

GABRB3
                                     (SEQ ID NO: 45)
GABRB3 F  (CTTGACAATCGAGTGGCTGA);
and (SEQ ID NO: 46)
GABRB3 R  (TCATCCGTGGTGTAGCCATA)
```

-continued

```
CYP26A1
                                          (SEQ ID NO: 47)
CYP26A1 F (AACCTGCACGACTCCTCGCACA);
and (SEQ ID NO: 48)
CYP26A1 R (AGGATGCGCATGGCGATTCG)

FOXD3
                                          (SEQ ID NO: 49)
FoxD3-F418 (GTGAAGCCGCCTTACTCGTAC);
and (SEQ ID NO: 50)
FoxD3-R770 (CCGAAGCTCTGCATCATGAG)

GDF3
                                          (SEQ ID NO: 51)
GDF3 F (GGCGTCCGCGGGAATGTACTTC);
and (SEQ ID NO: 52)
GDF3 R (TGGCTTAGGGGTGGTCTGGCC)

β-ACTIN
                                          (SEQ ID NO: 53)
beta-actin-F (CAACCGCGAGAAGATGAC);
and (SEQ ID NO: 54)
beta-actin-R (AGGAAGGCTGGAAGAGTG)

Sendai virus vector
                                          (SEQ ID NO: 55)
F15204 (GGATCACTAGGTGATATCGAGC);
and (SEQ ID NO: 56)
R15397e (ACCAGACAAGAGTTTAAGAGATATGTATC)
```

Example 16

ES Marker Expression in iPS Cells by Immunostaining

Figure 12:
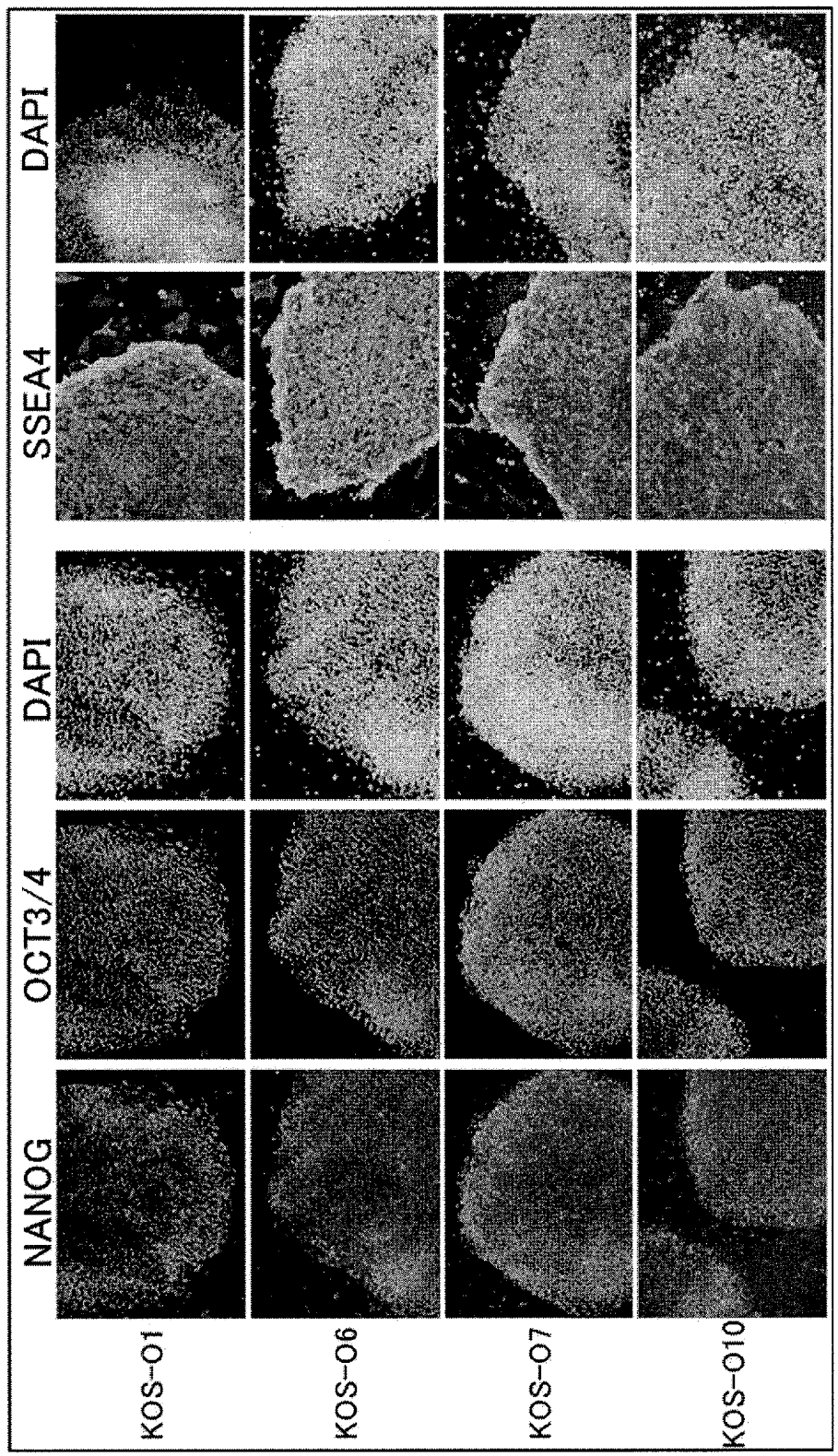
FIG. 12 shows the results of analyzing the expression of ES marker proteins in the iPS cell clones.

Cultured cells of BJ-derived iPS cell clones, KOS-O1, KOS-O6, KOS-O7, and KOS-O10, which were induced by Sendai virus vectors simultaneously carrying three reprogramming factors, were fixed using Mildform 10N (Wako Pure Chemical Industries, Ltd., catalog No. 133-10311). Immunostaining was carried out using an anti-Nanog antibody (ReproCELL, catalog No. RCAB0003P), anti-Oct3/4 antibody (Santa Cruz, catalog No. sc-5279), and anti-SSEA4 (Cell signaling, catalog No. 4755S) antibody. DAPI staining was performed simultaneously to stain the nucleus, and observation was made under a fluorescence microscope. As a result, for all of the evaluated Sendai virus vectors simultaneously carrying three reprogramming factors, expression of the ES marker proteins was confirmed in the induced BJ-derived iPS cell clones (FIG. 12).

Figure 13:
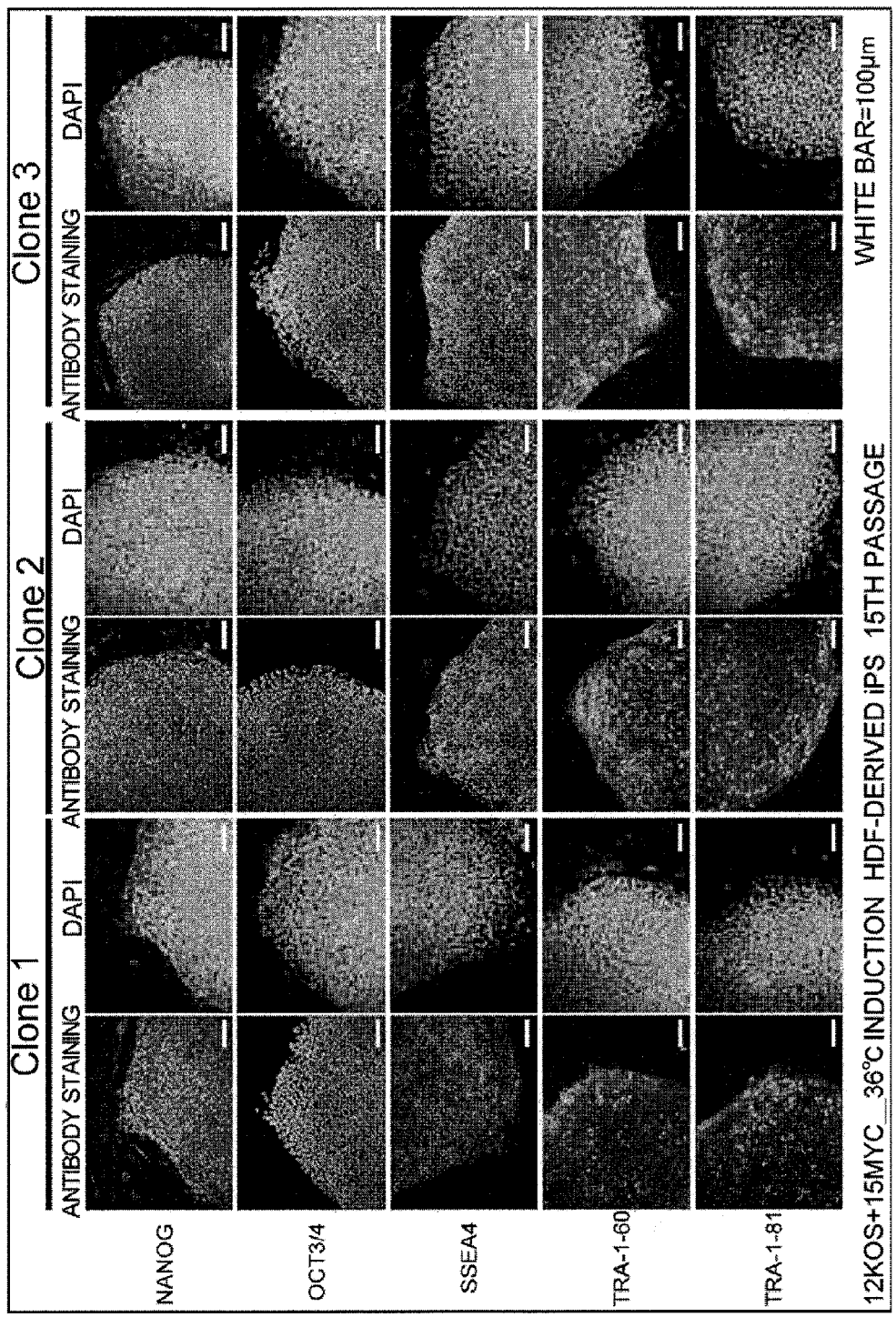
FIG. 13 shows the results of analyzing the expression of ES marker proteins in the iPS cell clones.
Figure 14:
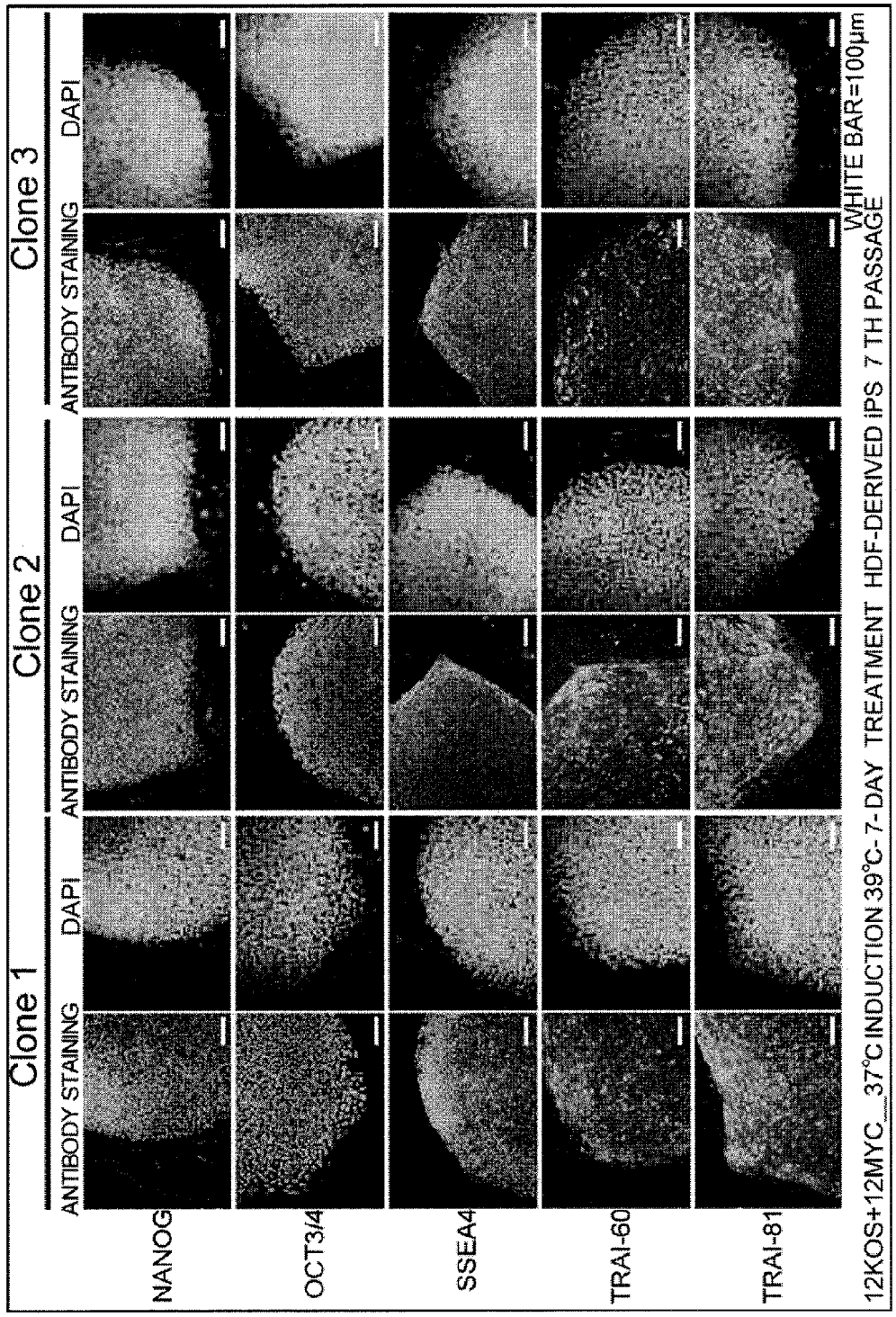
FIG. 14 shows the results of analyzing the expression of ES marker proteins in the iPS cell clones.

Immunostaining was performed using various antibodies on HDF cell-derived iPS clones induced and established at 36° C. using SeV(PM)KOS/TS12ΔF and SeV(HNL)c-rMYC/TS15ΔF (FIG. 13), and HDF cell-derived iPS clones established by induction at 37° C. using SeV(PM)KOS/TS12ΔF and SeV(HNL)c-rMYC/TS12ΔF and then culturing for 7 days at 39° C. (FIG. 14). DAPI staining was performed simultaneously, and observation was made under a fluorescence microscope. An anti-Nanog antibody (CST, Inc., catalog No. #4893S); anti-Oct3/4 antibody (Santa Cruz, catalog No. sc-5279); anti-SSEA4 (Cell signaling, catalog No. 4755S); anti-Tra-1-60 antibody (Stemgent, catalog No. 09-0068); and anti-Tra-1-81 antibody (Stemgent, catalog No. 09-0069) were used to confirm ES cell marker protein expression immunologically. As a result, for all the evaluated temperature-sensitive Sendai virus vectors simultaneously carrying three reprogramming factors, expression of the ES cell marker proteins was confirmed in the induced adult human (HDF)-derived iPS cell clones.

Example 17

Pluripotency of iPS Cells In Vitro

Figure 15:
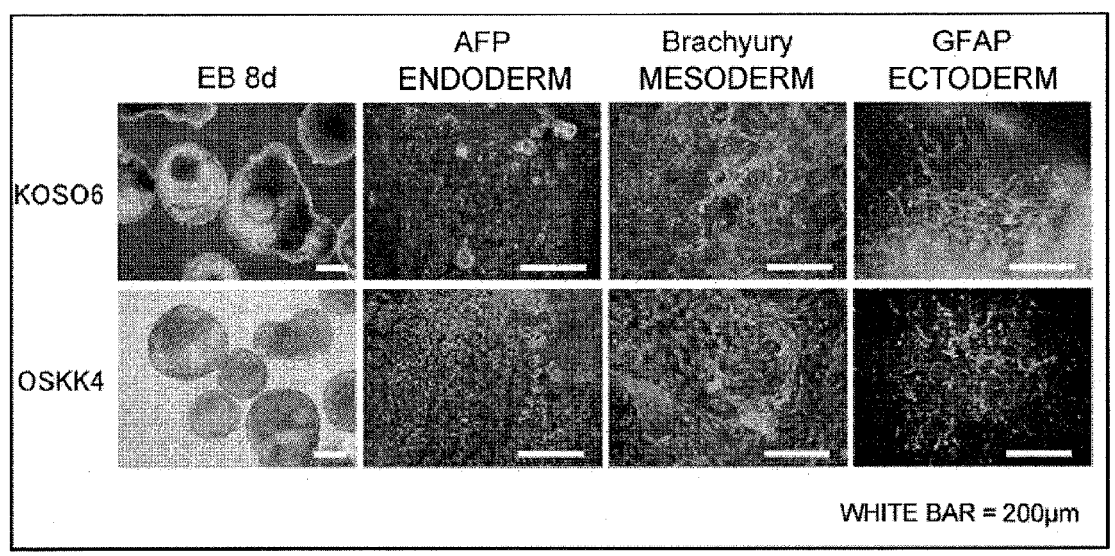
FIG. 15 shows the formation of embryoid bodies of an iPS cell clone.
Figure 16:
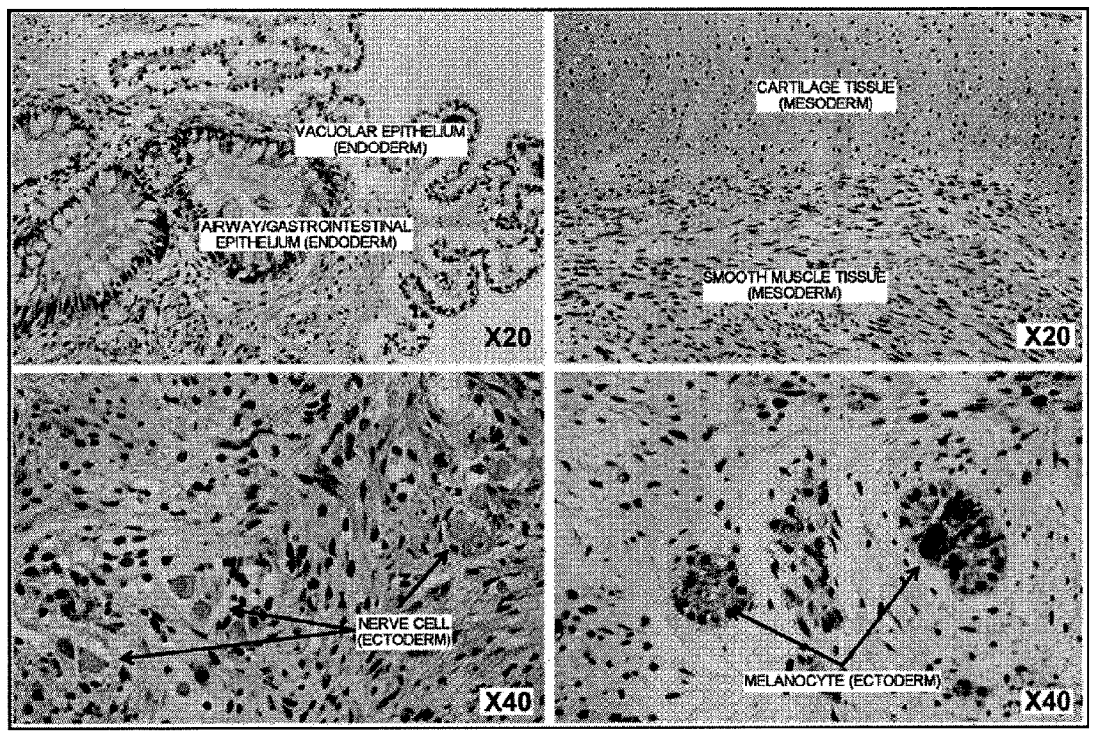
FIG. 16 shows the teratoma formation of an iPS cell clone.

An in vitro embryoid body formation experiment was conducted to assess the pluripotency of iPS cells induced with the Sendai virus vectors simultaneously carrying three reprogramming factors. Colonies of iPS clone KOS-O6 (derived from BJ) induced and established using SeV(PM)KOS/TSΔF and SeV(HNL)c-rMYC/TS15ΔF, and iPS clone OSKK4 (derived from BJ) induced and established using SeV(PM)OSK/TSΔF, SeV(HNL)c-rMYC/TS15ΔF, and SeV18+KLF4/TSΔF were detached from dishes using collagenase IV (Invitrogen, 17104-019). The cell masses were transferred into MPC-coated wells (Nunc, 145383), and incubated for eight days in suspension culture in D-MEM containing 10% FBS. Embryoid body formation was observed under a microscope. Sendai virus vector-induced iPS cells had the ability to differentiate, and all the iPS cells formed embryoid bodies. Many embryoid bodies including cystic embryoid bodies were observed (FIG. 15). Then, they were passaged onto gelatin-treated plates, and cultured for another eight days. Subsequently, antibody immunostaining was performed using an anti-α-fetoprotein (AFP) antibody (Sigma-Aldrich, catalog No. A8452), anti-Brachyury antibody (Sigma-Aldrich, catalog No. B8436), and anti-human glial fibrillary acidic protein (GFAP) antibody (Cosmo Bio, catalog No. ROI003), and observation under a fluorescence microscope confirmed that iPS cells induced by Sendai virus vectors simultaneously carrying three reprogramming factors can undergo triploblastic differentiation (FIG. 15).

Example 18

Pluripotency of iPS Cells In Vivo

Figure 17:
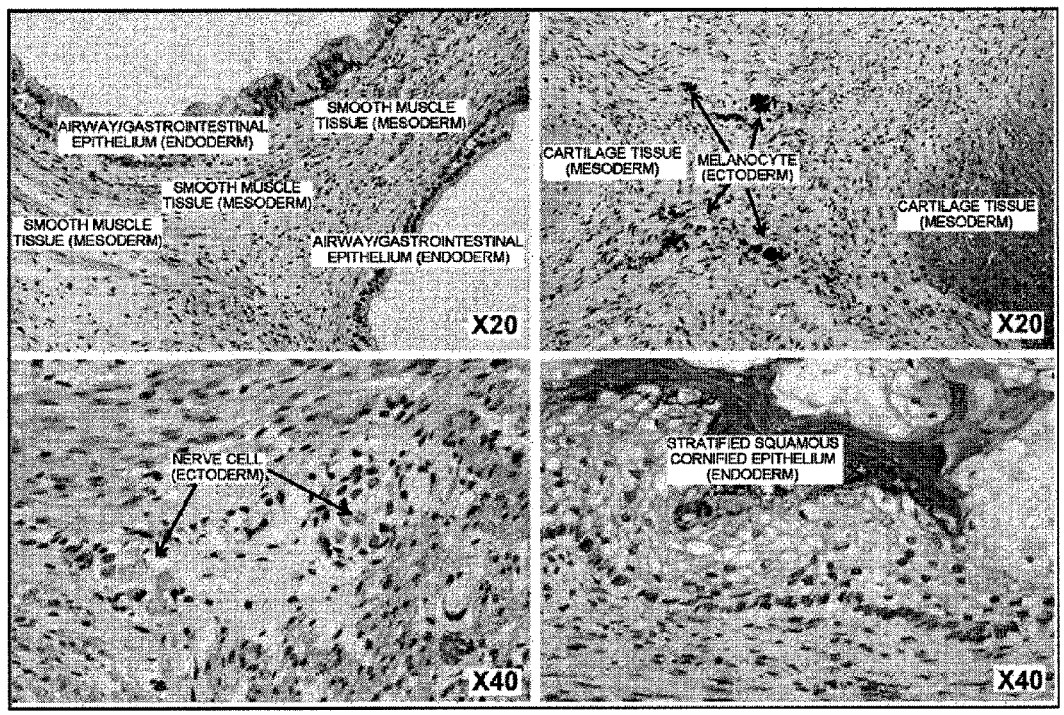
FIG. 17 shows the teratoma formation of an iPS cell clone.
Figure 18:
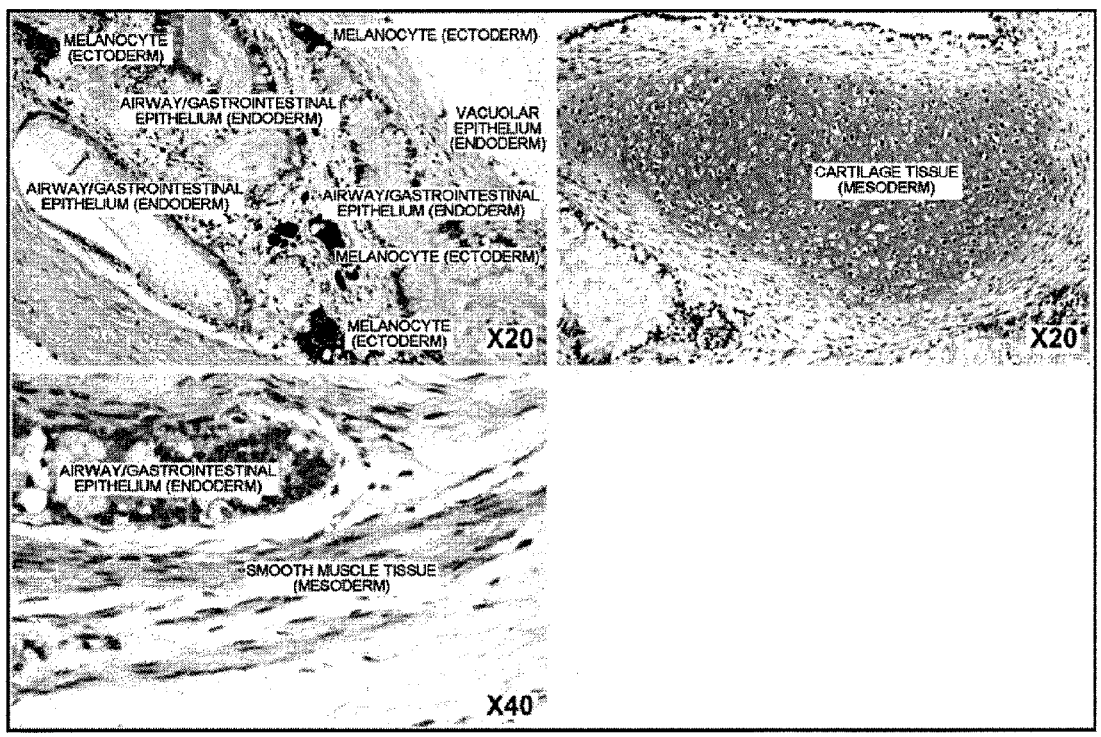
FIG. 18 shows the teratoma formation of an iPS cell clone.

The in vivo pluripotency of BJ cell-derived iPS clones, KOS-O6 and OSKK4, was assessed by teratoma formation in immunodeficient mice. KOS-O6 and OSKK4 clones were subcutaneously and intramuscularly inoculated into SCID mice, and samples were collected 105 days later and fixed in 10% formalin. Paraffin embedding, production of tissue sections, hematoxylin-eosin staining, and pathologic analyses were performed by request at Histochemical Laboratories Co., and triploblastic differentiation was confirmed (FIGS. 15, 17, and 18).

Example 19

Karyotype Analysis

Figure 19:
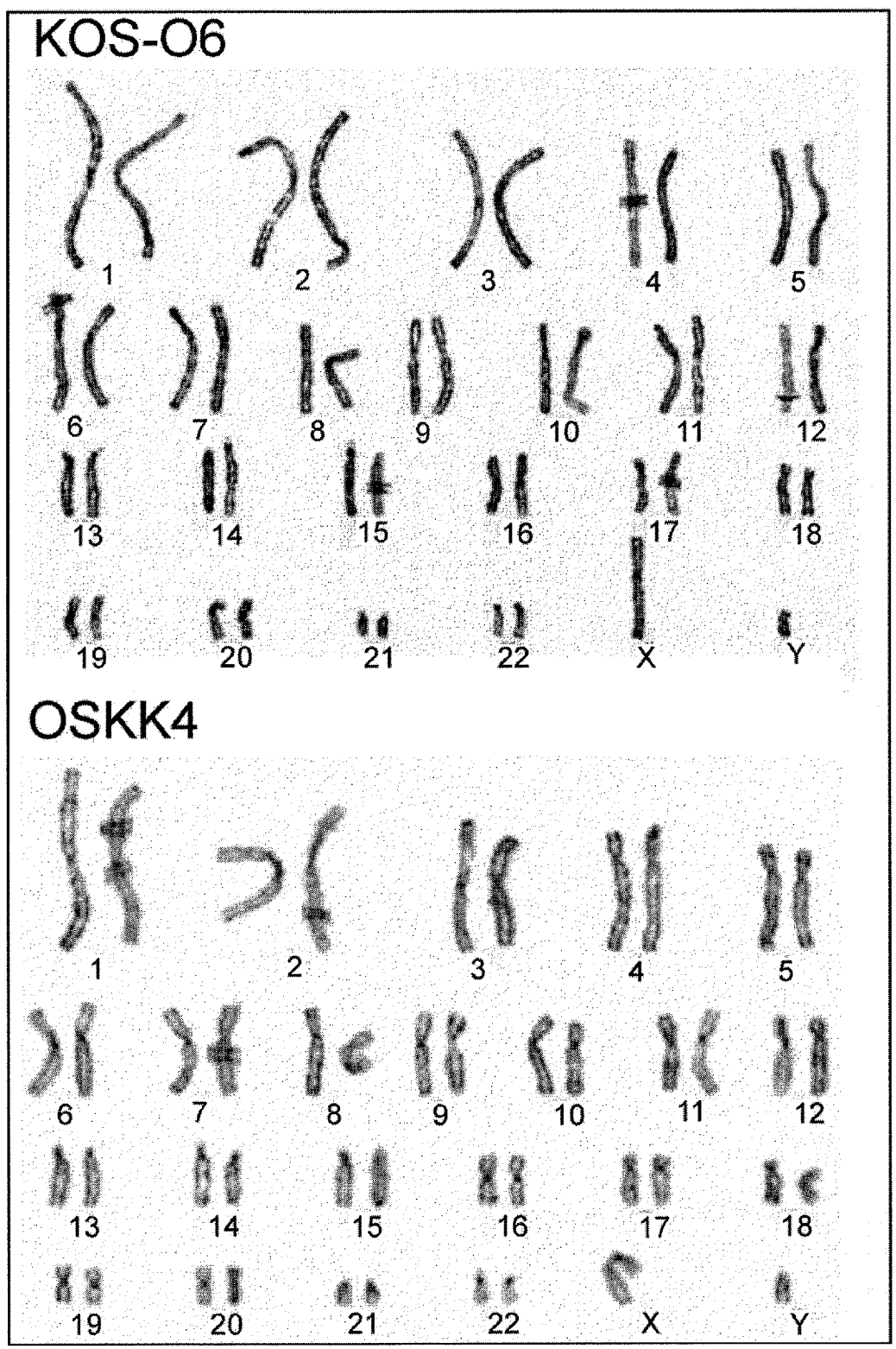
FIG. 19 shows the results of karyotype analyses of the iPS cell clones.

Karyotype analysis of BJ cell-derived iPS clones, KOS-O6 and OSKK4, was performed by request at Nihon Gene Research Laboratories Inc. The results showed that they both have 46 chromosomes, and that the karyotype is normal (FIG. 19).

Example 20

Promoter Analysis of iPS Cells

Figure 20:
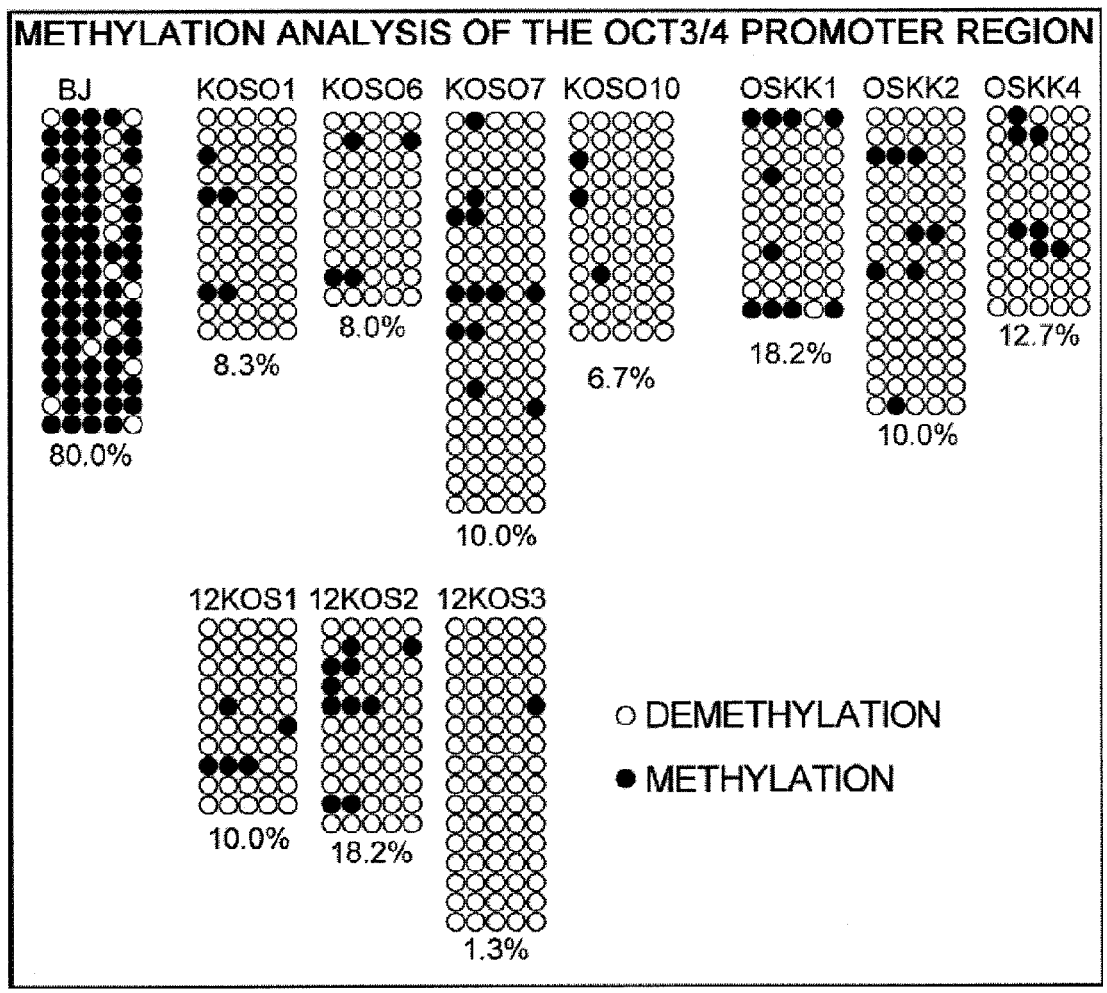
FIG. 20 shows the results of methylation analysis of the Oct3/4 promoter.

To assess whether the Oct3/4 gene promoter, which is expressed in ES cells, is activated in iPS cells, methylation analysis was performed by the bisulfite sequencing method described below. The result showed that the Oct3/4 promoter was highly methylated in the parental BJ and HDF (controls), which indicates that gene expression was suppressed. On the other hand, each of the clones of iPS cells induced by the Sendai virus vectors simultaneously carrying three reprogramming factors was found to be highly demethylated, and the Oct3/4 promoter region was found to be activated in SeV-iPS cells in a similar manner to ES cells (FIG. 20).

(Bisulfite Sequencing Method)

Genomic DNA was extracted from iPS cells using a DNAzol reagent (Invitrogen, catalog No. 10503027) or the Wizard Genomic DNA Purification Kit (Promega catalog No. A1120) according to the protocol attached to the kit. Then, the extracted genomic DNA was modified with bisulfite using the MethylEasy Xceed Rapid DNA Bisulphite Modification Kit (Takara, code number: GE004) according to the attached protocol. PCR was carried out using the bisulfite-modified genomic DNA as template, together with specific primers that target the promoter regions of the Oct3/4 gene. The PCR product was purified using the QIAquick PCR Purification Kit (QIAGEN, catalog No. 28106). The purified PCR product was TA-cloned using pGEM-T Easy Vector System I (Promega, catalog No. A1360) according to the attached protocol. Then, colony PCR was carried out using primers for colony PCR. Colony PCR was carried out using the GoTaq Green Master Mix (Promega, catalog No. M7123). The product was subject to agarose gel electrophoresis, and ten or more clones that gave a band of the correct size were selected. Colony PCR products of these clones were purified using the QIAquick PCR Purification Kit (QIAGEN, catalog No. 28106), and they were sequenced using the T7 and SP6 primers. The methylation status of the promoter regions was assessed by comparing the sequences with the target sequences after bisulfite modification.

Primers for amplification of the Oct3/4 gene promoter region and colony PCR (J. Biol. Chem., 2005, Vol. 280, 6257-6260):

```
                                        (SEQ ID NO: 57)
mOct4-3F: 5'-ATTTGTTTTTTGGGTAGTTAAAGGT-3'

(SEQ ID NO: 58)
mOct4-3R: 5'-CCAACTATCTTCATCTTAATAACATCC-3'
```

Primers for colony PCR:

```
                                        (SEQ ID NO: 59)
PGEMT-F: 5'-CACGACGTTGTAAAACGACGGCC-3'

(SEQ ID NO: 60)
PGEMT-R: 5'-CAGCTATGACCATGATTACGCC-3'
```

Primers for sequencing:

```
                                        (SEQ ID NO: 61)
T7: 5'-TAATACGACTCACTATAGGG-3'

(SEQ ID NO: 62)
SP6: 5'-CATACGATTTAGGTGACACTATAG-3'
```

Example 21

Vector Removal

Figure 21:
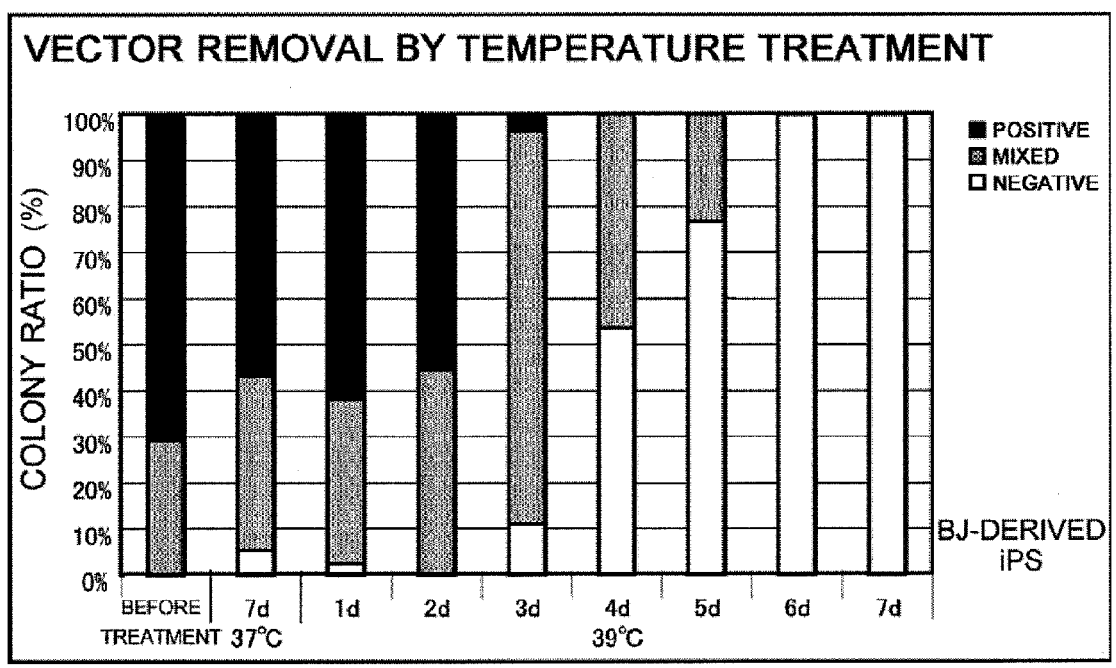
FIG. 21 shows the vector removal from iPS cells.

To assess vector removal from iPS cells induced by temperature-sensitive Sendai virus vectors simultaneously carrying three reprogramming genes, iPS cells induced by using SeV(PM)KOS/TS12ΔF and SeV(HNL)c-rMYC/TS12ΔF were passaged after culturing at 39° C. for 1, 2, 3, 4, 5, 6, and 7 days, and then cultured for another 7 days. The obtained iPS cells were immunologically stained using anti-Sendai virus antibodies to evaluate whether the vectors were removed. The results presented in FIG. 21 showed that from the third day of culturing at 39° C., the percentage of Sendai virus vector removal increased in a culturing time-dependent manner, and it was shown that the vectors can be removed almost completely by culturing for six to seven days.

Example 22

Natural Loss of Vectors

It has been shown that Sendai virus vectors are naturally removed from iPS cells induced using the conventional method, by passaging and culturing using common methods (Fusaki N. et al. (2009) Proc Jpn Acad Ser B Phys Biol Sci 85(8): 348-362). Natural removal was also observed for iPS cells induced using Sendai virus vectors simultaneously carrying three reprogramming factors and temperature-sensitive Sendai virus vectors simultaneously carrying three reprogramming factors. In particular, iPS cells induced at 36° C. using SeV(PM)KOS/TS12ΔF and SeV(HNL)c-rMYC/TS15ΔF were found to have very high efficiency in the natural loss of vectors, as compared to when induction was performed using the conventional method.

Figure 22:
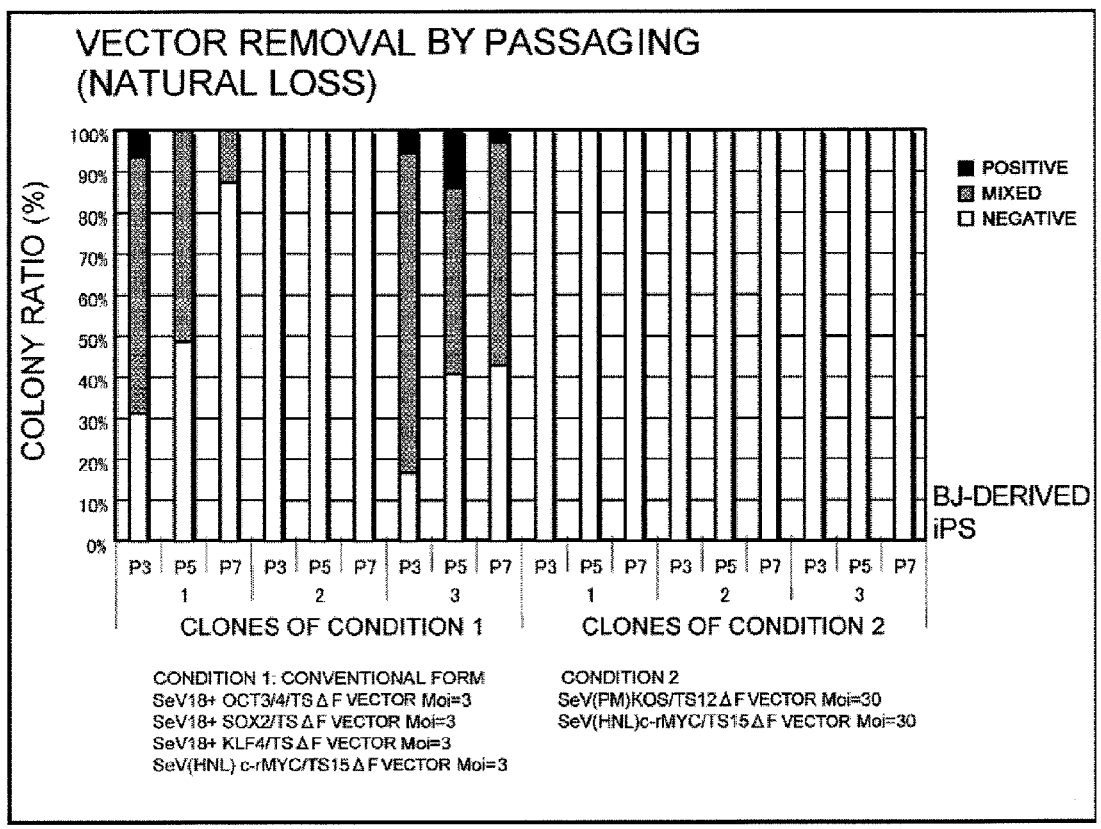
FIG. 22 shows the natural loss of the vectors from iPS cells.

Three clones each were selected from BJ-iPS cells induced by the conventional method and BJ-iPS cells induced at 36° C. using SeV(PM)KOS/TS12ΔF and SeV(HNL)c-rMYC/TS15ΔF, and they were passaged at 37° C. At the third, fifth and seventh passages, some of the cells were immunostained using anti-Sendai virus antibodies, and Sendai virus removal was examined. As a result, the BJ-iPS cells induced at 36° C. using SeV(PM)KOS/TS12ΔF and SeV(HNL)c-rMYC/TS15ΔF were negative for Sendai virus vectors in all three clones at the third passage. As for the conventional type, one of the three clones was negative for the vector, but the remaining two clones did not become completely vector-negative even at the seventh passage (FIG. 22).

Furthermore, vector removal was also confirmed at the third to fifth passages for iPS cells induced at 36° C. using SeV(PM)KOS/TS12ΔF and SeV(HNL)c-rMYC/TS15ΔF from cells other than BJ cells, for example, human adult skin-derived fibroblasts HDF (Applications, Inc. 106-05A-1388; derived from the cheek of a 36-year-old white adult female), and human fetal lung cell-derived fibroblast (MRC5; ATCC CCL-171).

Therefore, inducing iPS cells at 36° C. using SeV(PM)KOS/TS12ΔF and SeV(HNL)c-rMYC/TS15ΔF is an iPS induction method that has excellent efficiency in vector removal.

INDUSTRIAL APPLICABILITY

The present invention enables one to reduce the number of necessary Sendai virus vectors, as well as to remarkably increase the efficiency of reprogramming by loading multiple reprogramming factors onto a single vector. Since no foreign gene is integrated into the chromosome of the produced pluripotent stem cells, they are advantageous in tests and research. Furthermore, it is expected that immunological rejection and ethical problems in disease treatments, as well as the risk of tumorigenesis due to genetic toxicity can be avoided.

The invention claimed is:

1. A method for producing a transgenic cell in the induction of a pluripotent stem cell, which comprises introducing into a cell a Sendai virus vector into which the KLF gene, OCT gene, and SOX gene in this order are inserted immediately downstream, on the 5' side in the genome, of the Sendai virus P gene.

2. The method of claim 1, which further comprises introducing into the cell another Sendai virus vector inserted with the MYC gene or Glis1 gene.

3. The method of claim 2, wherein the MYC gene or Glis1 gene is inserted immediately upstream, on the 3' side in the genome, of the Sendai virus L gene.

4. The method of claim 1, which further comprises introducing into the cell another Sendai virus vector inserted with the KLF gene.

5. The method of claim 4, wherein the KLF gene is inserted upstream, on the 3' side in the genome, of the Sendai virus N gene.

6. A Sendai virus vector into which the KLF gene, OCT gene, and SOX gene in this order are inserted immediately downstream, on the 5' side in the genome, of the Sendai virus P gene.

7. A nucleic acid encoding a genome or an antigenome of the Sendai virus vector of claim 6.

8. A kit for use in gene delivery for induction of a pluripotent stem cell, which comprises the Sendai virus vector of claim 6 and a different Sendai virus vector inserted with the MYC gene or Glis1 gene.

9. The kit of claim 8, wherein the MYC gene or Glis1 gene is inserted immediately upstream, on the 3' side in the genome, of the Sendai virus L gene.

10. The kit of claim 8, which further comprises a different Sendai virus vector inserted with the KLF gene.

11. The kit of claim 10, wherein the KLF gene is inserted upstream, on the 3' side in the genome, of the Sendai virus N gene.

12. A composition for use in gene delivery for induction of a pluripotent stem cell, which comprises the Sendai virus vector of claim 6 and a pharmaceutically acceptable carrier and/or a medium.

13. The composition of claim 12, further comprising a different Sendai virus vector into which the MYC gene or Glis1 gene is inserted.

14. The composition of claim 13, wherein the MYC gene or Glis1 gene is inserted immediately upstream, on the 3' side in the genome, of the Sendai virus L gene.

15. The composition of claim 12, further comprising a different Sendai virus vector into which the KLF gene is inserted.

16. The composition of claim 15, wherein the KLF gene is inserted upstream, on the 3' side in the genome, of the Sendai virus N gene.

\* \* \* \* \*

UNITED STATES PATENT AND TRADEMARK OFFICE
CERTIFICATE OF CORRECTION

PATENT NO. : 9,090,909 B2
APPLICATION NO. : 13/819235
DATED : July 28, 2015
INVENTOR(S) : Hiroshi Ban et al.

It is certified that error appears in the above-identified patent and that said Letters Patent is hereby corrected as shown below:

On the Title Page, Item (57)

ABSTRACT, replace "reprograming" with –reprogramming–.

In the Specification

Column 1, Line 21, replace "reprograming" with –reprogramming–;

Line 31, replace "reprograming" with –reprogramming–;

Line 34, replace "reprograming" with –reprogramming–.

Column 7, Line 50, replace "FIN gene" with –HN gene–;

Line 66, replace "DMV 230087; HPIV-1, 538067"
with –DMV Z30087; HPIV-1, S38067–.

Column 8, Line 13, replace "576876" with –S76876–.

Column 10, Line 17, replace "FIN gene" with –HN gene–;

Line 32, replace "FIN gene" with –HN gene–;

Line 36, replace "FIN gene" with –HN gene–;

Line 40, "For example," should be the start of a new paragraph.

Column 12, Line 2, replace "an amino acids" with –amino acids–;

Line 8, replace "H is" with –His–;

Line 54, replace "/L15581" with –/L1558I–;

Line 56, replace "(L15581)" with –(L1558 I)–;

Signed and Sealed this
Ninth Day of February, 2016

Michelle K. Lee
*Director of the United States Patent and Trademark Office*

CERTIFICATE OF CORRECTION (continued)
U.S. Pat. No. 9,090,909 B2

Line 58, replace "/L15581)" with –/L1558 I)–.

Column 15, Line 56, replace "E-1-S-KLF" with –E- I -S-KLF–;

Line 60, replace "E-1-S-KLF" with –E- I -S-KLF–.

Column 16, Line 41, replace "FIN gene" with –HN gene–.

Column 24, Line 19, "MYC family" should be the start of a new paragraph.

Column 25, Line 21, replace "enhancer binding protein a" with –enhancer binding protein α–;

Column 27, Line 24, replace "pancreatic p" with –pancreatic β–.

Column 28, Line 55, replace "deTGFβ" with –deIGFP–;

Line 62, replace "DH5a" with –DH5α–.

Column 29, Line 45, "The SOX2" should be the start of a new paragraph.

Column 32, Line 14, replace "Non" with –NotI–;

Column 37, Line 1, replace "and cc at 4°C" with –and ∞ at 4°C–;

Line 19, replace "and cc at 4°C" with –and ∞ at 4°C–;

Line 22, replace "and Nod" with –and *Not*I–.

UNITED STATES PATENT AND TRADEMARK OFFICE
CERTIFICATE OF CORRECTION

PATENT NO. : 9,090,909 B2  
APPLICATION NO. : 13/819235  
DATED : July 28, 2015  
INVENTOR(S) : Hiroshi Ban et al.

Page 1 of 1

It is certified that error appears in the above-identified patent and that said Letters Patent is hereby corrected as shown below:

In The Specification

Column 2, Line 37, replace "reprograming" with -- reprogramming --.

Signed and Sealed this  
Third Day of May, 2016

Michelle K. Lee  
*Director of the United States Patent and Trademark Office*

```
                              SEQUENCE LISTING

<160> NUMBER OF SEQ ID NOS: 62

<210> SEQ ID NO 1
<211> LENGTH: 10
<212> TYPE: RNA
<213> ORGANISM: Artificial Sequence
<220> FEATURE:
<223> OTHER INFORMATION: Sendai virus start sequence (S sequence)

<400> SEQUENCE: 1 cmuuvmcccu                                                                10

<210> SEQ ID NO 2
<211> LENGTH: 10
<212> TYPE: RNA
<213> ORGANISM: Artificial Sequence
<220> FEATURE:
<223> OTHER INFORMATION: Sendai virus start sequence (S sequence)

<400> SEQUENCE: 2
cuuugacccu                                                                10

<210> SEQ ID NO 3
<211> LENGTH: 10
<212> TYPE: RNA
<213> ORGANISM: Artificial Sequence
<220> FEATURE:
<223> OTHER INFORMATION: Sendai virus start sequence (S sequence)

<400> SEQUENCE: 3
cauucacccu                                                                10

<210> SEQ ID NO 4
<211> LENGTH: 10
<212> TYPE: RNA
<213> ORGANISM: Artificial Sequence
<220> FEATURE:
<223> OTHER INFORMATION: Sendai virus start sequence (S sequence)

<400> SEQUENCE: 4
cuuucacccu                                                                10

<210> SEQ ID NO 5
<211> LENGTH: 10
<212> TYPE: DNA
<213> ORGANISM: Artificial Sequence
<220> FEATURE:
<223> OTHER INFORMATION: Sendai virus start sequence (S sequence)

<400> SEQUENCE: 5
agggtcaaag                                                                10

<210> SEQ ID NO 6
<211> LENGTH: 10
<212> TYPE: DNA
<213> ORGANISM: Artificial Sequence
<220> FEATURE:
<223> OTHER INFORMATION: Sendai virus start sequence (S sequence)

<400> SEQUENCE: 6
agggtgaatg                                                                10
```

<210> SEQ ID NO 7
<211> LENGTH: 10
<212> TYPE: DNA
<213> ORGANISM: Artificial Sequence
<220> FEATURE:
<223> OTHER INFORMATION: Sendai virus start sequence (S sequence)

<400> SEQUENCE: 7
agggtgaaag                                                                10

<210> SEQ ID NO 8
<211> LENGTH: 9
<212> TYPE: RNA
<213> ORGANISM: Artificial Sequence
<220> FEATURE:
<223> OTHER INFORMATION: Sendai virus end sequence (E sequence)

<400> SEQUENCE: 8 uuuuucuua                                                                 9

<210> SEQ ID NO 9
<211> LENGTH: 9
<212> TYPE: DNA
<213> ORGANISM: Artificial Sequence
<220> FEATURE:
<223> OTHER INFORMATION: Sendai virus end sequence (E sequence)

<400> SEQUENCE: 9 taagaaaaa                                                                 9

<210> SEQ ID NO 10
<211> LENGTH: 40
<212> TYPE: DNA
<213> ORGANISM: Artificial Sequence
<220> FEATURE:
<223> OTHER INFORMATION: Synthetic Construct

<400> SEQUENCE: 10
gaaatttcac ctaagcggcc gcaatggcag atatctatag                              40

<210> SEQ ID NO 11
<211> LENGTH: 40
<212> TYPE: DNA
<213> ORGANISM: Artificial Sequence
<220> FEATURE:
<223> OTHER INFORMATION: Synthetic Construct

<400> SEQUENCE: 11
ctatagatat ctgccattgc ggccgcttag gtgaaatttc                              40

<210> SEQ ID NO 12
<211> LENGTH: 35
<212> TYPE: DNA
<213> ORGANISM: Artificial Sequence
<220> FEATURE:
<223> OTHER INFORMATION: Synthetic Construct

<400> SEQUENCE: 12
attgcggccg cgacatggct gtcagcgacg cgctg                                   35

<210> SEQ ID NO 13
<211> LENGTH: 85
<212> TYPE: DNA
<213> ORGANISM: Artificial Sequence
<220> FEATURE:
<223> OTHER INFORMATION: Synthetic Construct -continued

<400> SEQUENCE: 13
tccgaagcca ggtgtcccgc catggcggct gttaggtgga tgaactttca ccctaagttt    60
ttcttactac ggttaaaaat gcctc    85

<210> SEQ ID NO 14
<211> LENGTH: 85
<212> TYPE: DNA
<213> ORGANISM: Artificial Sequence
<220> FEATURE:
<223> OTHER INFORMATION: Synthetic Construct

<400> SEQUENCE: 14
gaggcatttt taaccgtagt aagaaaaact tagggtgaaa gttcatccac ctaacagccg    60
ccatggcggg acacctggct tcgga    85

<210> SEQ ID NO 15
<211> LENGTH: 90
<212> TYPE: DNA
<213> ORGANISM: Artificial Sequence
<220> FEATURE:
<223> OTHER INFORMATION: Synthetic Construct

<400> SEQUENCE: 15
ccgtctccat catgttgtac atggcggcgt gttaggtgaa atctttcacc ctaagttttt    60
cttattctac ggtcagtttg aatgcatggg    90

<210> SEQ ID NO 16
<211> LENGTH: 90
<212> TYPE: DNA
<213> ORGANISM: Artificial Sequence
<220> FEATURE:
<223> OTHER INFORMATION: Synthetic Construct

<400> SEQUENCE: 16
cccatgcatt caaactgacc gtagaataag aaaaacttag ggtgaaagat ttcacctaac    60
acgccgccat gtacaacatg atggagacgg    90

<210> SEQ ID NO 17
<211> LENGTH: 85
<212> TYPE: DNA
<213> ORGANISM: Artificial Sequence
<220> FEATURE:
<223> OTHER INFORMATION: Synthetic Construct

<400> SEQUENCE: 17
attgcggccg cgatgaactt tcaccctaag ttttcttac tacggtcaca tgtgtgagag    60
gggcagtgtg ccgttaatgg ccgtg    85

<210> SEQ ID NO 18
<211> LENGTH: 22
<212> TYPE: DNA
<213> ORGANISM: Artificial Sequence
<220> FEATURE:
<223> OTHER INFORMATION: Synthetic Construct

<400> SEQUENCE: 18
acaagagaaa aaacatgtat gg    22

<210> SEQ ID NO 19
<211> LENGTH: 62
<212> TYPE: DNA

```
<213> ORGANISM: Artificial Sequence
<220> FEATURE:
<223> OTHER INFORMATION: Synthetic Construct

<400> SEQUENCE: 19
ggcggcgtgt taggtggatg actttcaccc taagttttc ttactacggt cagtttgaat      60
gc                                                                   62

<210> SEQ ID NO 20
<211> LENGTH: 64
<212> TYPE: DNA
<213> ORGANISM: Artificial Sequence
<220> FEATURE:
<223> OTHER INFORMATION: Synthetic Construct

<400> SEQUENCE: 20
tagtaagaaa aacttagggt gaaagtcatc cacctaacac gccgccatgt acaacatgat      60
ggag                                                                 64

<210> SEQ ID NO 21
<211> LENGTH: 60
<212> TYPE: DNA
<213> ORGANISM: Artificial Sequence
<220> FEATURE:
<223> OTHER INFORMATION: Synthetic Construct

<400> SEQUENCE: 21
tgttaggtgg atgaactttc acctaagtt tttcttacta cggtcacatg tgtgagaggg      60

<210> SEQ ID NO 22
<211> LENGTH: 64
<212> TYPE: DNA
<213> ORGANISM: Artificial Sequence
<220> FEATURE:
<223> OTHER INFORMATION: Synthetic Construct

<400> SEQUENCE: 22
tagtaagaaa aacttagggt gaaagttcat ccacctaaca cgccgccatg gctgtcagcg      60
acgc                                                                 64

<210> SEQ ID NO 23
<211> LENGTH: 23
<212> TYPE: DNA
<213> ORGANISM: Artificial Sequence
<220> FEATURE:
<223> OTHER INFORMATION: Synthetic Construct

<400> SEQUENCE: 23
gataacagca cctcctcccg act                                            23

<210> SEQ ID NO 24
<211> LENGTH: 27
<212> TYPE: DNA
<213> ORGANISM: Artificial Sequence
<220> FEATURE:
<223> OTHER INFORMATION: Synthetic Construct

<400> SEQUENCE: 24
atgcgctggt tcacgcccgc gcccagg                                        27

<210> SEQ ID NO 25
<211> LENGTH: 23
<212> TYPE: DNA
<213> ORGANISM: Artificial Sequence
```

```
<220> FEATURE:
<223> OTHER INFORMATION: Synthetic Construct

<400> SEQUENCE: 25
agcgctgcac atgaaggagc acc                                           23

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
aatgtatcga aggtgctcaa                                               20

<210> SEQ ID NO 27
<211> LENGTH: 22
<212> TYPE: DNA
<213> ORGANISM: Artificial Sequence
<220> FEATURE:
<223> OTHER INFORMATION: Synthetic Construct

<400> SEQUENCE: 27
agagaacaag actaaggcta cc                                            22

<210> SEQ ID NO 28
<211> LENGTH: 21
<212> TYPE: DNA
<213> ORGANISM: Artificial Sequence
<220> FEATURE:
<223> OTHER INFORMATION: Synthetic Construct

<400> SEQUENCE: 28
accttgacaa tcctgatgtg g                                             21

<210> SEQ ID NO 29
<211> LENGTH: 22
<212> TYPE: DNA
<213> ORGANISM: Artificial Sequence
<220> FEATURE:
<223> OTHER INFORMATION: Synthetic Construct

<400> SEQUENCE: 29
ccatcaacac tccccaagga cc                                            22

<210> SEQ ID NO 30
<211> LENGTH: 22
<212> TYPE: DNA
<213> ORGANISM: Artificial Sequence
<220> FEATURE:
<223> OTHER INFORMATION: Synthetic Construct

<400> SEQUENCE: 30
agacgtgatg cgtttgaggc cc                                            22

<210> SEQ ID NO 31
<211> LENGTH: 28
<212> TYPE: DNA
<213> ORGANISM: Artificial Sequence
<220> FEATURE:
<223> OTHER INFORMATION: Synthetic Construct

<400> SEQUENCE: 31
ccaccatgag tgtggatcca gcttgtcc                                      28
```

<210> SEQ ID NO 32
<211> LENGTH: 26
<212> TYPE: DNA
<213> ORGANISM: Artificial Sequence
<220> FEATURE:
<223> OTHER INFORMATION: Synthetic Construct

<400> SEQUENCE: 32
ctcacacgtc ttcaggttgc atgttc                                    26

<210> SEQ ID NO 33
<211> LENGTH: 24
<212> TYPE: DNA
<213> ORGANISM: Artificial Sequence
<220> FEATURE:
<223> OTHER INFORMATION: Synthetic Construct

<400> SEQUENCE: 33
tgcccggacc tccatcagag ccag                                      24

<210> SEQ ID NO 34
<211> LENGTH: 26
<212> TYPE: DNA
<213> ORGANISM: Artificial Sequence
<220> FEATURE:
<223> OTHER INFORMATION: Synthetic Construct

<400> SEQUENCE: 34
tcagtccagg atggtcttga agtctg                                    26

<210> SEQ ID NO 35
<211> LENGTH: 20
<212> TYPE: DNA
<213> ORGANISM: Artificial Sequence
<220> FEATURE:
<223> OTHER INFORMATION: Synthetic Construct

<400> SEQUENCE: 35 aaacccagc acatcaactc                                            20

<210> SEQ ID NO 36
<211> LENGTH: 19
<212> TYPE: DNA
<213> ORGANISM: Artificial Sequence
<220> FEATURE:
<223> OTHER INFORMATION: Synthetic Construct

<400> SEQUENCE: 36
gtcattccct gggtggttc                                            19

<210> SEQ ID NO 37
<211> LENGTH: 30
<212> TYPE: DNA
<213> ORGANISM: Artificial Sequence
<220> FEATURE:
<223> OTHER INFORMATION: Synthetic Construct

<400> SEQUENCE: 37
atgagccagc aactgaagaa acgggcaaag                                30

<210> SEQ ID NO 38
<211> LENGTH: 29
<212> TYPE: DNA
<213> ORGANISM: Artificial Sequence
<220> FEATURE:
<223> OTHER INFORMATION: Synthetic Construct

```
<400> SEQUENCE: 38
ctactttccc tcttgttcat tcttgttcg                                       29

<210> SEQ ID NO 39
<211> LENGTH: 24
<212> TYPE: DNA
<213> ORGANISM: Artificial Sequence
<220> FEATURE:
<223> OTHER INFORMATION: Synthetic Construct

<400> SEQUENCE: 39
atggactgca ggaagatggc ccgc                                            24

<210> SEQ ID NO 40
<211> LENGTH: 26
<212> TYPE: DNA
<213> ORGANISM: Artificial Sequence
<220> FEATURE:
<223> OTHER INFORMATION: Synthetic Construct

<400> SEQUENCE: 40
ttaatagtag ctttgtatag aaaggc                                          26

<210> SEQ ID NO 41
<211> LENGTH: 21
<212> TYPE: DNA
<213> ORGANISM: Artificial Sequence
<220> FEATURE:
<223> OTHER INFORMATION: Synthetic Construct

<400> SEQUENCE: 41
gcagcgacca gtcctccgac t                                               21

<210> SEQ ID NO 42
<211> LENGTH: 20
<212> TYPE: DNA
<213> ORGANISM: Artificial Sequence
<220> FEATURE:
<223> OTHER INFORMATION: Synthetic Construct

<400> SEQUENCE: 42
aacgtgggga aggcctgtgc                                                 20

<210> SEQ ID NO 43
<211> LENGTH: 27
<212> TYPE: DNA
<213> ORGANISM: Artificial Sequence
<220> FEATURE:
<223> OTHER INFORMATION: Synthetic Construct

<400> SEQUENCE: 43
ccaccatggg ctccgtgtcc aaccagc                                         27

<210> SEQ ID NO 44
<211> LENGTH: 23
<212> TYPE: DNA
<213> ORGANISM: Artificial Sequence
<220> FEATURE:
<223> OTHER INFORMATION: Synthetic Construct

<400> SEQUENCE: 44
gtcaattctg tgcctccggg agc                                             23

<210> SEQ ID NO 45
```

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 45
cttgacaatc gagtggctga                                                   20

<210> SEQ ID NO 46
<211> LENGTH: 20
<212> TYPE: DNA
<213> ORGANISM: Artificial Sequence
<220> FEATURE:
<223> OTHER INFORMATION: Synthetic Construct

<400> SEQUENCE: 46
tcatccgtgg tgtagccata                                                   20

<210> SEQ ID NO 47
<211> LENGTH: 22
<212> TYPE: DNA
<213> ORGANISM: Artificial Sequence
<220> FEATURE:
<223> OTHER INFORMATION: Synthetic Construct

<400> SEQUENCE: 47
aacctgcacg actcctcgca ca                                                22

<210> SEQ ID NO 48
<211> LENGTH: 20
<212> TYPE: DNA
<213> ORGANISM: Artificial Sequence
<220> FEATURE:
<223> OTHER INFORMATION: Synthetic Construct

<400> SEQUENCE: 48
aggatgcgca tggcgattcg                                                   20

<210> SEQ ID NO 49
<211> LENGTH: 21
<212> TYPE: DNA
<213> ORGANISM: Artificial Sequence
<220> FEATURE:
<223> OTHER INFORMATION: Synthetic Construct

<400> SEQUENCE: 49
gtgaagccgc cttactcgta c                                                 21

<210> SEQ ID NO 50
<211> LENGTH: 20
<212> TYPE: DNA
<213> ORGANISM: Artificial Sequence
<220> FEATURE:
<223> OTHER INFORMATION: Synthetic Construct

<400> SEQUENCE: 50
ccgaagctct gcatcatgag                                                   20

<210> SEQ ID NO 51
<211> LENGTH: 22
<212> TYPE: DNA
<213> ORGANISM: Artificial Sequence
<220> FEATURE:
<223> OTHER INFORMATION: Synthetic Construct

<400> SEQUENCE: 51
```
ggcgtccgcg ggaatgtact tc                                              22

<210> SEQ ID NO 52
<211> LENGTH: 21
<212> TYPE: DNA
<213> ORGANISM: Artificial Sequence
<220> FEATURE:
<223> OTHER INFORMATION: Synthetic Construct

<400> SEQUENCE: 52
tggcttaggg gtggtctggc c                                               21

<210> SEQ ID NO 53
<211> LENGTH: 18
<212> TYPE: DNA
<213> ORGANISM: Artificial Sequence
<220> FEATURE:
<223> OTHER INFORMATION: Synthetic Construct

<400> SEQUENCE: 53
caaccgcgag aagatgac                                                   18

<210> SEQ ID NO 54
<211> LENGTH: 18
<212> TYPE: DNA
<213> ORGANISM: Artificial Sequence
<220> FEATURE:
<223> OTHER INFORMATION: Synthetic Construct

<400> SEQUENCE: 54
aggaaggctg gaagagtg                                                   18

<210> SEQ ID NO 55
<211> LENGTH: 22
<212> TYPE: DNA
<213> ORGANISM: Artificial Sequence
<220> FEATURE:
<223> OTHER INFORMATION: Synthetic Construct

<400> SEQUENCE: 55
ggatcactag gtgatatcga gc                                              22

<210> SEQ ID NO 56
<211> LENGTH: 29
<212> TYPE: DNA
<213> ORGANISM: Artificial Sequence
<220> FEATURE:
<223> OTHER INFORMATION: Synthetic Construct

<400> SEQUENCE: 56
accagacaag agtttaagag atatgtatc                                       29

<210> SEQ ID NO 57
<211> LENGTH: 25
<212> TYPE: DNA
<213> ORGANISM: Artificial Sequence
<220> FEATURE:
<223> OTHER INFORMATION: Synthetic Construct

<400> SEQUENCE: 57
atttgttttt tgggtagtta aaggt                                           25

<210> SEQ ID NO 58
<211> LENGTH: 27
<212> TYPE: DNA

```
<213> ORGANISM: Artificial Sequence
<220> FEATURE:
<223> OTHER INFORMATION: Synthetic Construct

<400> SEQUENCE: 58
ccaactatct tcatcttaat aacatcc                                            27

<210> SEQ ID NO 59
<211> LENGTH: 23
<212> TYPE: DNA
<213> ORGANISM: Artificial Sequence
<220> FEATURE:
<223> OTHER INFORMATION: Synthetic Construct

<400> SEQUENCE: 59
cacgacgttg taaaacgacg gcc                                                23

<210> SEQ ID NO 60
<211> LENGTH: 22
<212> TYPE: DNA
<213> ORGANISM: Artificial Sequence
<220> FEATURE:
<223> OTHER INFORMATION: Synthetic Construct

<400> SEQUENCE: 60
cagctatgac catgattacg cc                                                 22

<210> SEQ ID NO 61
<211> LENGTH: 20
<212> TYPE: DNA
<213> ORGANISM: Artificial Sequence
<220> FEATURE:
<223> OTHER INFORMATION: Synthetic Construct

<400> SEQUENCE: 61
taatacgact cactataggg                                                    20

<210> SEQ ID NO 62
<211> LENGTH: 24
<212> TYPE: DNA
<213> ORGANISM: Artificial Sequence
<220> FEATURE:
<223> OTHER INFORMATION: Synthetic Construct

<400> SEQUENCE: 62
catacgattt aggtgacact atag                                               24
```